(12) United States Patent
Kurosaki et al.

(10) Patent No.: US 9,278,968 B2
(45) Date of Patent: Mar. 8, 2016

(54) IMIDAZOPYRIDINE COMPOUNDS

(71) Applicant: ASTELLAS PHARMA INC., Tokyo (JP)

(72) Inventors: Toshio Kurosaki, Tokyo (JP); Tsubasa Watanabe, Tokyo (JP); Kazuhiko Ohne, Tokyo (JP); Hiroki Ishioka, Tokyo (JP); Eisuke Nozawa, Tokyo (JP); Takeshi Hanazawa, Tokyo (JP); Shunichiro Hachiya, Tokyo (JP); Hiroshi Shibata, Tokyo (JP); Yuji Koga, Tokyo (JP); Ryo Mizoguchi, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 14/428,798

(22) PCT Filed: Nov. 28, 2013

(86) PCT No.: PCT/JP2013/082057
§ 371 (c)(1),
(2) Date: Mar. 17, 2015

(87) PCT Pub. No.: WO2014/084312
PCT Pub. Date: Jun. 5, 2014

(65) Prior Publication Data
US 2015/0232464 A1    Aug. 20, 2015

(30) Foreign Application Priority Data
Nov. 30, 2012 (JP) .................................. 2012-262962

(51) Int. Cl.
*A61K 31/437* (2006.01)
*C07D 471/04* (2006.01)

(52) U.S. Cl.
CPC .................................... *C07D 471/04* (2013.01)

(58) Field of Classification Search
USPC ........................................... 514/300; 546/121
See application file for complete search history.

(56) References Cited

U.S. PATENT DOCUMENTS

| 8,778,964 B2 | 7/2014 | Vakalopoulos et al. |
| 8,946,215 B2 | 2/2015 | Vakalopoulos et al. |
| 2014/0088080 A1 | 3/2014 | Koga et al. |

FOREIGN PATENT DOCUMENTS

WO    2012 165399    12/2012

OTHER PUBLICATIONS

International Search Report Issued Jan. 21, 2014 in PCT/JP13/082057 Filed Nov. 28, 2013.
H. Sanada et al., Atherosclerosis, vol. 178, pp. 179-185 (2005).
R. H. Boger et al., JACC, vol. 32, No. 5, pp. 1336-1344 (1998).

*Primary Examiner* — Charanjit Aulakh
(74) *Attorney, Agent, or Firm* — Oblon, McClelland, Maier & Neustadt, L.L.P.

(57) ABSTRACT

[Problem]
A pharmaceutical composition for treating or preventing various cardiovascular diseases, which have sGC activities based on improvement of cGMP signals, is provided.
[Means for Solution]
It was found that imidazo[1,2-a]pyridine compounds having a carbamoyl group at the 3-position and a particular cyclic group at the 8-position via a methyleneoxy group, or a salt thereof have sGC activation, and are useful as active ingredients of pharmaceutical compositions for treating or preventing various sGC-related cardiovascular diseases, in particular, peripheral arterial diseases, intermittent claudication, critical limb ischemia, hypertension, and pulmonary hypertension, thereby completing the present invention.

18 Claims, 5 Drawing Sheets

IMIDAZOPYRIDINE COMPOUNDS

CROSS REFERENCE TO RELATED APPLICATION

This application is a National Stage entry under 35 USC 371 of PCT/JP13/082057, filed on Nov. 28, 2013, and claims priority to Japanese Patent Application No. 2012-262962, filed on Nov. 30, 2012.

TECHNICAL FIELD

The present invention relates to imidazo[1,2-a]pyridine compounds useful as active ingredients of pharmaceutical compositions for treating or preventing various cardiovascular diseases, which have soluble guanylate cyclase (sGC) activation based on improvement of cyclic guanosine monophosphate (cGMP) signals.

BACKGROUND ART cGMP is an important intracellular messenger and is known to be involved in the regulation of various physiological phenomena such as relaxation and proliferation of smooth muscle cells, aggregation and adhesion of platelets, and signaling of nerve cells, through the control of a cGMP-dependent protein kinase, a phosphodiesterase, and ion channels. The cGMP is catalytically produced from guanosine triphosphate (GTP) by a guanylate cyclase in the response to various extracellular and intracellular stimulation. There have been reported two groups of guanylate cyclases to date, that is, particulate guanylate cyclases stimulated by peptidic messengers (for example, atrial natriuretic peptides, brain natriuretic peptides, and the like) and sGC stimulated by nitric oxide (NO).

With respect to the sGC, the following are known. That is, the sGC is one of the most important target molecules of NO that is a messenger which plays a very important role in maintaining homeostasis of the body, and forms an NO/sGC/cGMP pathway. It has been reported that this enzyme is constituted with two subunits, each of the heterodimer contains one heme, and the heme plays a central role in an activation mechanism. It is believed that when NO binds to the iron atom in the heme, the enzyme is changed to an active conformation. Therefore, there is no stimulation by NO with enzyme preparations containing no heme. Although carbon monoxide (CO) may also bind to the iron in the heme, but the stimulation by CO is significantly lower than that by NO.

The sGC is constituted with α and β subunits. Analysis of sGC from tissue-specific distributions and in different growth steps demonstrated multiple subtype with different subunit compositions. The distribution of the respective subunits have been studied with mammals including a human, and it has been widely known that α1 and β1 subunits are expressed in many tissues and the α1β1 forms have a pattern of a heterodimer that works functionally. α2 subunits have been also recognised, which exist fewer organs as compared to the α1. It has been reported that the α2 subunits are expressed more frequently than α1 in the brain, the lung, the colon, the heart, the spleen, the uterus, and the placenta. Subunits called α3 and β3 were isolated from the human brain, but are homologous to α1 and β1. In addition, according to recent studies, α2i subunits which contain an insert in the catalytic domain have been identified. All of these subunits exhibit high homology in catalytic domain regions.

Under pathophysiological conditions, such as hyperglycemia, hyperlipidemia, hypertension, or the like, it has been reported that there is inhibition of the production of or promotion of the degradation of sGC activating factors such as NO for the reasons of increased generation of free radicals, and the like. With a decrease in the sGC activating factors, NO/sGC/cGMP signals are attenuated, which causes, for example, increased blood pressure, platelet activation, or increased cell proliferation and cell adhesion. As a result, a variety of cardiovascular diseases, specifically, hypertension (including pulmonary hypertension), atherosclerosis, lumbar spinal canal stenosis, peripheral arterial diseases, intermittent claudication, critical limb ischemia, stable or unstable angina pectoris, heart failure, thrombosis, stroke, sexual dysfunction, and the like occur. Therefore, a new drug having a mechanism of activating sGC is expected to be useful for treating or preventing such diseases by normalizing cGMP production.

As the sGC activator, there have been known, for example, "heme-dependent activators" which activate sGC depending on heme groups, such as NO donors as described later and the like, and "heme-independent activators" which are independent on the heme groups (Non-Patent Document 1).

For the activation of sGC, a group of compounds called NO donors such as organic nitrates have been widely used so far. These compounds are heme-dependent activators which activate sGC by being metabolized in vivo to produce NO, which then binds to a central iron atom of a heme. However, the NO donors have critical disadvantages such as expression of a resistance, a decrease in the effects and the like is expressed in addition to side-effects, and therefore, there is a demand for a novel sGC activator that does not have these disadvantages.

For example, compounds of the following formulae (a) to (c) have been reported as compounds having sGC activating action (Patent Document 1).

[Chem. 1]

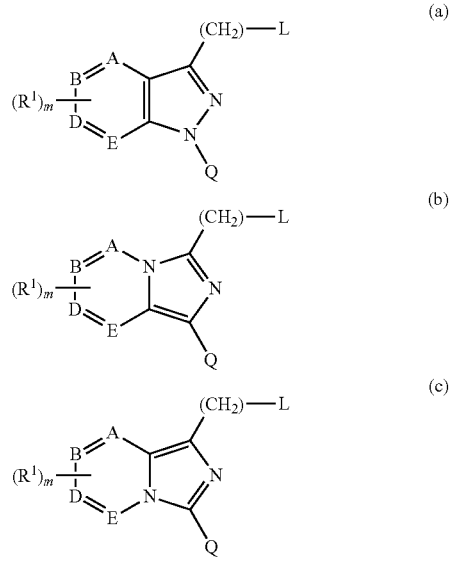

(Compounds of the formula (a) are pyrazolo[3,4]fused bicyclic compounds, and compounds of formulae (b) and (c) are imidazo[1,5]fused bicyclic compounds. Further, Q means substituted heterocycle in any one of the formulae (a) to (c). For details, refer to the document.)

In this document, there is no disclosure or suggestion of compounds having an imidazo[1,2-a]pyridine scaffold.

In addition, pyrazole derivatives or pyrazolo[3,4-b]pyridine derivatives are disclosed as the sGC activating compounds in International Publications WO 2000/06569, WO 2000/21954, WO 2001/83490, WO 2003/004503, WO 2003/095451, WO 2003/086407, WO 2003/097063, WO 2007/124854, WO 2007/128454, WO 2008/031513, WO 2008/061657, WO 2010/078900, WO 2010/079120, WO 2011/147809, WO 2012/004258, WO 2012/004259, WO 2012/010576, WO 2012/010577, WO 2012/010578, WO 2012/028647, WO 2012/059548, WO 2012/059549, WO 2012/143510, WO 2012/152629, WO 2012/152630, WO 2013/004785, WO 2013/030288, WO 2013/104597, WO 2013/104598, and WO 2013/104703. However, in any of these documents, there is no disclosure or suggestion of compounds having an imidazo[1,2-a]pyridine scaffold.

Furthermore, compounds of the following formula (d) have been reported as sGC activators (Patent Document 2).

[Chem. 2]

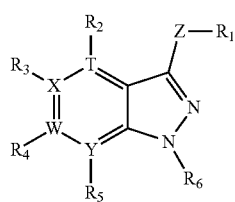

(d)

(wherein Z is O, S, or $N(R_7)$, $R_7$ is H or alkyl, and $R_6$ is aryl, arylalkenyl, heteroring, -(alkenyl)-(heteroring), or heterocycloalkyl. For details, refer to the document).

However, this document does not disclose or suggest compounds having an imidazo[1,2-a]pyridine scaffold.

As other sGC activators, 1H-pyrazole-5-carboxylic acid derivatives (Patent Document 3), biaryl derivatives (Patent Document 4), and benzylindazole derivatives (Non-Patent Document 2) have been reported.

Furthermore, compounds having an imidazo[1,2-a]pyridine scaffold, for example, compounds of the following formula (e) useful for the treatment of gastrointestinal ulcer as an H+/K+-ATPase inhibitors have been reported (Non-Patent Document 3).

[Chem. 3]

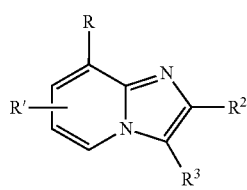

(e)

(wherein R means substituted alkoxy group, R' means H or phenethyl, $R^2$ means H or lower alkyl, and $R^3$ means substituted alkyl or the like. For details, refer to the document).

This document does not disclose or suggest sGC activators, and aminocarbonyl is not included in $R^3$ of the compound of the formula (e).

Moreover, compounds of the formula (f) useful for the treatment of allergy, inflammation, pain, or the like as bradykinin antagonists have been reported (Patent Document 5).

[Chem. 4]

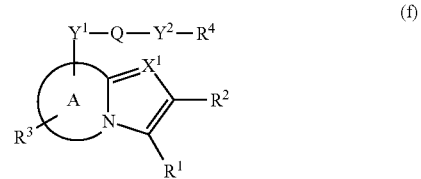

(f)

(wherein $R^1$ to $R^3$ each mean hydrogen, lower alkyl, or the like, $R^4$ means an aryl group which may have a suitable substituent, or the like, Q means O, NH, or the like, $X^1$ means N or C—$R^5$, $Y^1$ and $Y^2$ each mean a single bond or a lower alkylene group, and Ring A means 6-membered nitrogen-containing heterocycle. For details, refer to the document).

This document does not disclose or suggest sGC activators, and aminocarbonyl is not included in $R^1$ of the compound of the formula (f).

Furthermore, compounds of formula (g) with H+/K+-ATPase enzyme inhibitory activities and useful for the inhibition of gastric acid secretion have been reported (Patent Document 6).

[Chem. 5]

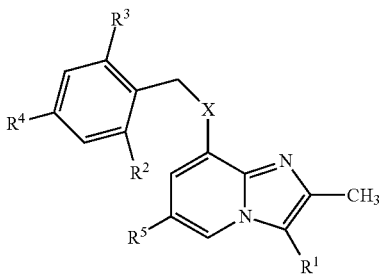

(g)

(wherein $R^1$ is $CH_3$ or $CH_2OH$, $R^2$ and $R^3$ are each lower alkyl, $R^4$ is H or halogen, $R^5$ is H, halogen, or lower alkyl, and X is NH or O. For details, refer to the document).

This document does not disclose or suggest sGC activators, and aminocarbonyl is not included in $R^1$ of the compound of the formula (g).

Moreover, compounds of formula (h) have been reported as cardiac ion channel modulators and as antiarrhythmic agents (Patent Document 7).

[Chem. 6]

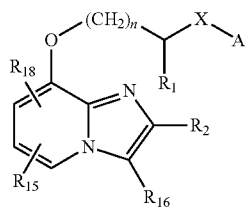

(h)

(wherein $R_2$, $R_{15}$, $R_{16}$, and $R_{18}$ are each Br, Cl, F, carboxy, H, —OH, hydroxymethyl, or the like, and $R_1$ is H, $C_{1-6}$ alkyl, aryl, benzyl, or the like. For details, refer to the document).

This document does not disclose or suggest sGC activators, and aminocarbonyl is not included in $R^{16}$ of the compound of the formula (h).

In addition, compounds of formula (i) useful as a drug for treating bacterial infection, particularly tuberculosis, have been reported (Patent Document 8).

[Chem. 7]

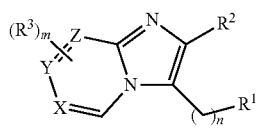

(wherein X, Y, and Z are each CH or the like, n is 0 to 3, m is 0 to 4, $R^1$ is —C(O)N($R^4$)$_2$ or the like, $R^2$ is $C_{1-10}$ alkyl or the like, $R^3$ is —$OR^6$ or the like, and $R^6$ is $C_{1-10}$ alkyl optionally substituted, or the like. For details, refer to the document).

This document specifically discloses a compound, in which X, Y, and Z are each CH, n is 0, $R^1$ is —C(O)N($R^4$)$_2$, $R^2$ is $C_{1-10}$ alkyl, m is 1, $R^3$ is —$OR^6$, and $R^6$ is H, methyl, or difluoromethyl. However, this document does not disclose or suggest sGC activators.

In addition, compounds of formula (j) with sGC activity and useful for cardiovascular diseases, in particular intermittent claudication and critical limb ischemia accompanied with peripheral arterial diseases as well as hypertension, and the like, have been reported (Patent Document 9).

[Chem. 8]

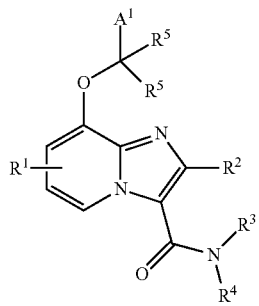

(wherein $A^1$ is cycloalkyl which may be substituted, aryl which may be substituted or the like, $R^1$ is H or the like, $R^2$ is $R^0$ or the like, $R^0$ is lower alkyl, $R^3$ is H or the like, $R^4$ is —Y-$A^2$ or the like, Y is $C_{1-10}$ alkylene which may be substituted or the like, and $A^2$ is heteroaryl which may be substituted. For details, refer to the document).

RELATED ART

Patent Document

[Patent Document 1] Pamphlet of International Publication WO 2008/031513
[Patent Document 2] Pamphlet of International Publication WO 2003/076408
[Patent Document 3] Pamphlet of International Publication WO 2000/027394
[Patent Document 4] Pamphlet of International Publication WO 2001/032604
[Patent Document 5] JP-A-H7-242666
[Patent Document 6] Pamphlet of International Publication WO 1998/37080
[Patent Document 7] Pamphlet of International Publication WO 2001/096335
[Patent Document 8] Pamphlet of International Publication WO 2011/113606
[Patent Document 9] Pamphlet of International Publication WO 2012/165399
[Non-Patent Document 1] Journal of Cardiovascular Pharmacology (2010), Vol. 56, p. 229
[Non-Patent Document 2] Blood (1994), Vol. 84, p. 4226
[Non-Patent Document 3] Journal of Medicinal Chemistry (1985), Vol. 28, p. 876

DISCLOSURE OF INVENTION

Problems to be Solved by the Invention

A pharmaceutical composition comprising imidazo[1,2-a]pyridine compounds, useful as active ingredients of pharmaceutical compositions for treating or preventing various cardiovascular diseases, which have sGC activities based on improvement of cGMP signals, is provided.

Means for Solving the Problems

The present inventors have made extensive studies on compounds having sGC activation, and as a result, they have found that imidazo[1,2-a]pyridine compounds having a carbamoyl group at the 3-position and a particular cyclic group at the 8-position via a methyleneoxy group, or a salt thereof have sGC activation, and are useful as active ingredients of pharmaceutical compositions for treating or preventing various sGC-related cardiovascular diseases, in particular, peripheral arterial diseases, intermittent claudication, critical limb ischemia, hypertension, and pulmonary hypertension, thereby completing the present invention.

The compounds represented by the formula (I) has a different structure from specific compounds disclosed in the above Patent Document 8 in that the substituent $A^1$ is a ring group.

Further, the basic application to which this application claims a priority was filed before the publication of the above Patent Document 9.

That is, the present invention relates to a compound of formula (I) or a salt thereof, and pharmaceutical compositions comprising the compound of formula (I) or a salt thereof and a pharmaceutically acceptable excipient.

[Chem. 9]

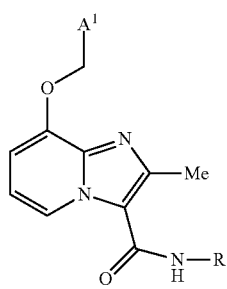

(wherein
$A^1$ is cyclohexyl, phenyl substituted with 1 to 3 F(s), or 3-fluoropyridin-2-yl, R is a group represented by any one of the following formulae (i) to (vii):

[Chem. 10]

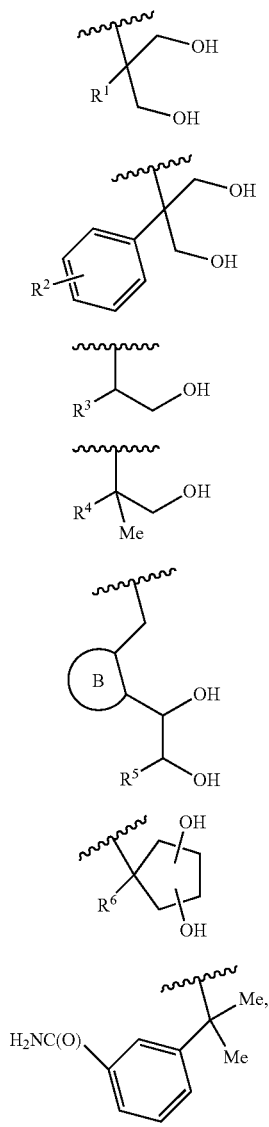

$R^1$ is 5- or 6-membered heteroaryl containing 1 to 4 heteroatoms selected from oxygen, sulfur, and nitrogen, which is unsubstituted or substituted with the same or different 1 to 4 substituent(s) selected from Group D, provided that there is no case where $R^1$ is unsubstituted pyridine, Group D consists of lower alkyl substituted with the same or different 1 to 3 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen; —O-(lower alkyl substituted with the same or different 1 to 3 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen); $R^0$; OH; $OR^0$; $COOH$; $COOR^0$; $CONH_2$; $CONHR^0$; $CON(R^0)_2$; $NH_2$; $NHR^0$; $N(R^0)_2$; CN; cycloalkyl having 3 to 8 carbon atoms; halogen and (tetrazolyl which is unsubstituted or substituted with lower alkyl), $R^0$s are the same or different from each other and lower alkyl, $R^2$ is lower alkyl substituted with the same or different 1 to 3 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen; —O-(lower alkyl substituted with the same or different 1 or 2 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen); OH; $OR^0$; $COOR^0$; $CONH_2$; $CONHR^0$; $CON(R^0)_2$; $NH_2$; $NHR^0$; $N(R^0)_2$; CN; cycloalkyl having 3 to 8 carbon atoms; halogen or tetrazolyl, $R^3$ is 5- or 6-membered heteroaryl containing 1 to 4 heteroatoms selected from oxygen, sulfur, and nitrogen, which is unsubstituted or substituted with the same or different 1 to 4 substituent(s) selected from Group D, provided that there is no case where $R^3$ is pyridyl, furyl, thienyl, or 4,6-diamino-1,3,5-triazin-2-yl, which is unsubstituted, $R^4$ is 5- or 6-membered heteroaryl containing 1 to 4 heteroatoms selected from oxygen, sulfur, and nitrogen, which is unsubstituted or substituted with the same or different 1 to 4 substituent(s) selected from Group D; or phenyl substituted with the same or different 1 to 4 substituent(s) selected from the group consisting of lower alkyl substituted with the same or different 1 to 3 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen; —O-(lower alkyl substituted with the same or different 1 to 3 substituent(s) selected from the group consisting of OH, $OR^0$, COOH, $COOR^0$, $CONH_2$, $CONHR^0$, $CON(R^0)_2$, $NH_2$, $NHR^0$, $N(R^0)_2$, CN, cycloalkyl having 3 to 8 carbon atoms, and halogen); OH; $OR^0$; $COOR^0$; $CONH_2$; $CONHR^0$; $CON(R^0)_2$; $NH_2$; $NHR^0$; $N(R^0)_2$; CN; cycloalkyl having 3 to 8 carbon atoms; halogen and (tetrazolyl which is unsubstituted or substituted with lower alkyl), provided that there is no case where $R^4$ is unsubstituted pyridyl, $R^5$ is H or $R^0$, B is a benzene ring or a pyridine ring, $R^6$ is 5- or 6-membered heteroaryl containing 1 to 4 heteroatoms selected from oxygen, sulfur, and nitrogen, which is unsubstituted or substituted with the same or different 1 to 4 substituent(s) selected from Group D, and Me is methyl).

Furthermore, unless specifically described otherwise, when symbols in one formula in the present specification are also used in other formulae, same symbols denote same meanings.

Moreover, the present invention relates to pharmaceutical compositions for treating or preventing sGC-related cardiovascular diseases, which include compound of formula (I) or a salt thereof. Further, said pharmaceutical compositions include agents for treating or preventing sGC-related cardiovascular diseases, which include compounds of the formula (I) or a salt thereof.

The present invention further relates to use of compound of formula (I) or a salt thereof for preparation of pharmaceutical compositions for treating or preventing sGC-related cardiovascular diseases, use of compound of formula (I) or a salt thereof for treating or preventing sGC-related cardiovascular diseases, compound of the formula (I) or a salt thereof for treating or preventing sGC-related cardiovascular diseases, and methods for treating or preventing sGC-related cardiovascular diseases, comprising administering to a subject an effective amount of compound of formula (I) or a salt thereof. In this regard, the "subjects" refer to humans or other animals in need of the prevention or treatment, and in a certain embodiment, humans in need of the prevention or treatment.

Effects of the Invention

Compound of formula (I) or a salt thereof has an sGC activation and can be used as active ingredients of pharmaceutical compositions for treating or preventing sGC-related cardiovascular diseases, for example, hypertension, atherosclerosis, lumbar spinal canal stenosis, peripheral arterial diseases, intermittent claudication, critical limb ischemia, stable or unstable angina pectoris, heart failure, thrombosis, stroke, sexual dysfunction, pulmonary hypertension, or the like.

EMBODIMENTS FOR CARRYING OUT THE INVENTION

Figure 1:
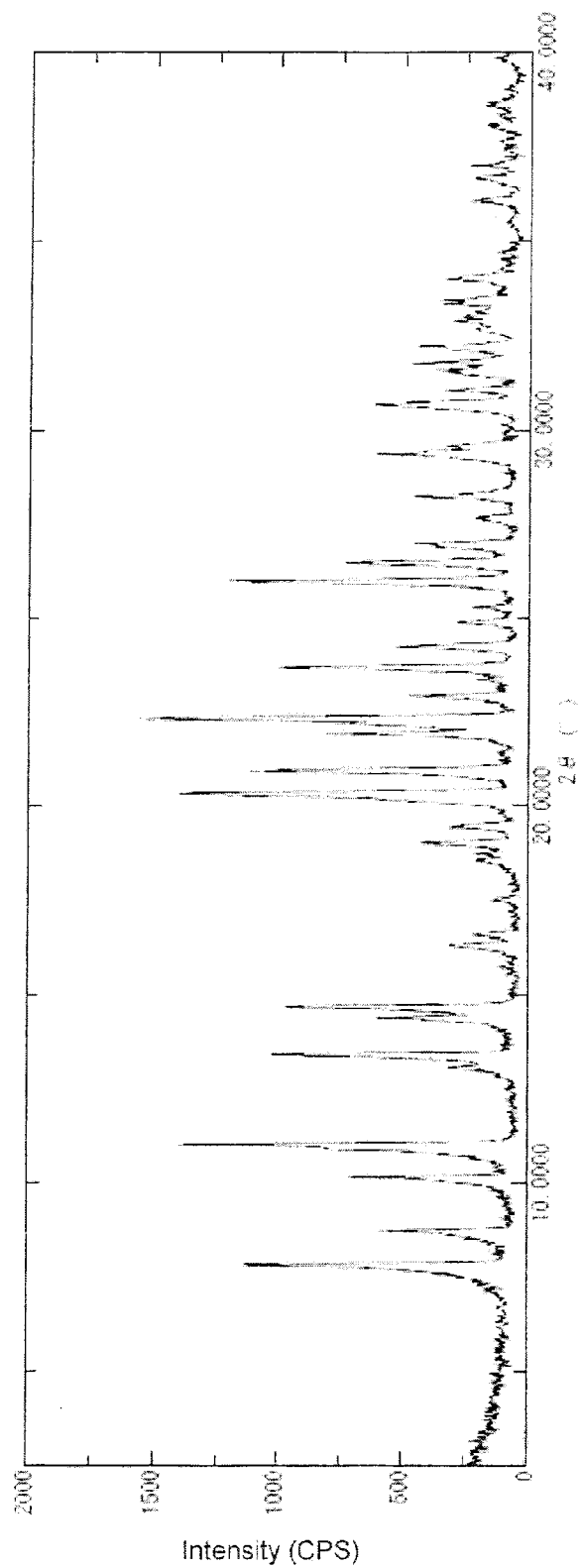
FIG. 1 shows a powder X-ray diffraction pattern of the compound of Example 113.
Figure 2:
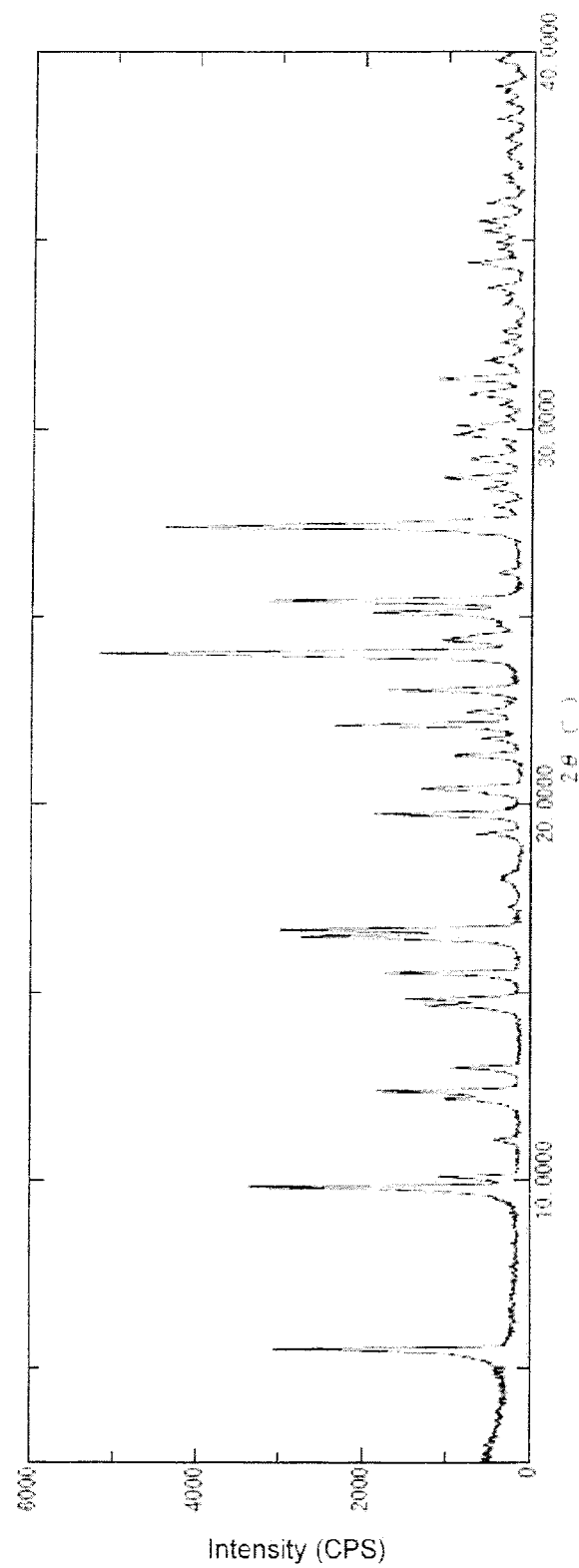
FIG. 2 shows a powder X-ray diffraction pattern of the compound of Example 115.
Figure 3:
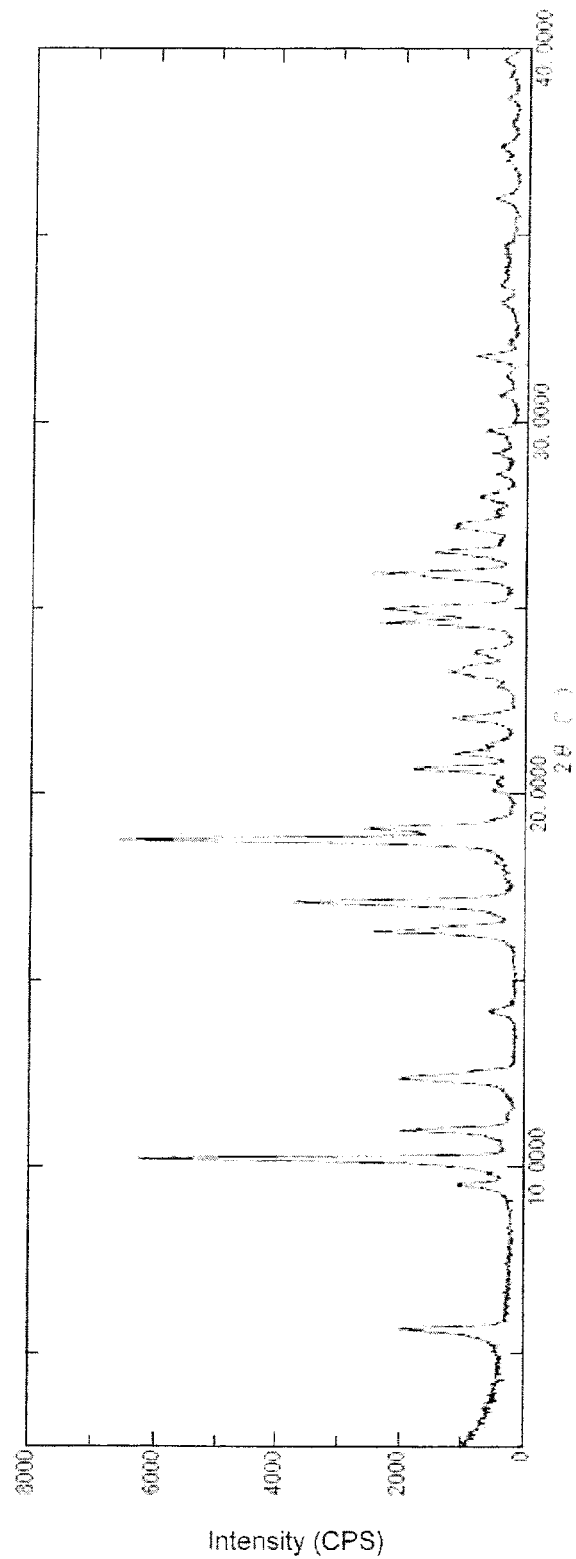
FIG. 3 shows a powder X-ray diffraction pattern of the compound of Example 116.
Figure 4:
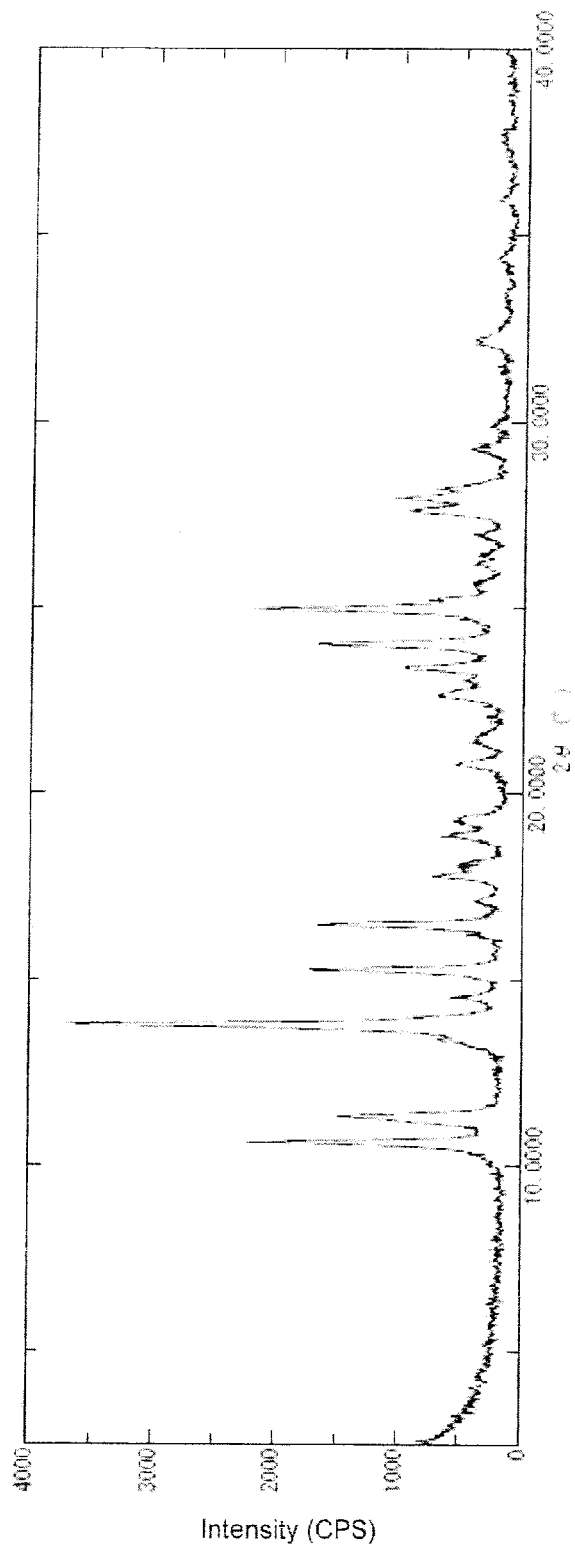
FIG. 4 shows a powder X-ray diffraction pattern of the compound of Example 117.
Figure 5:
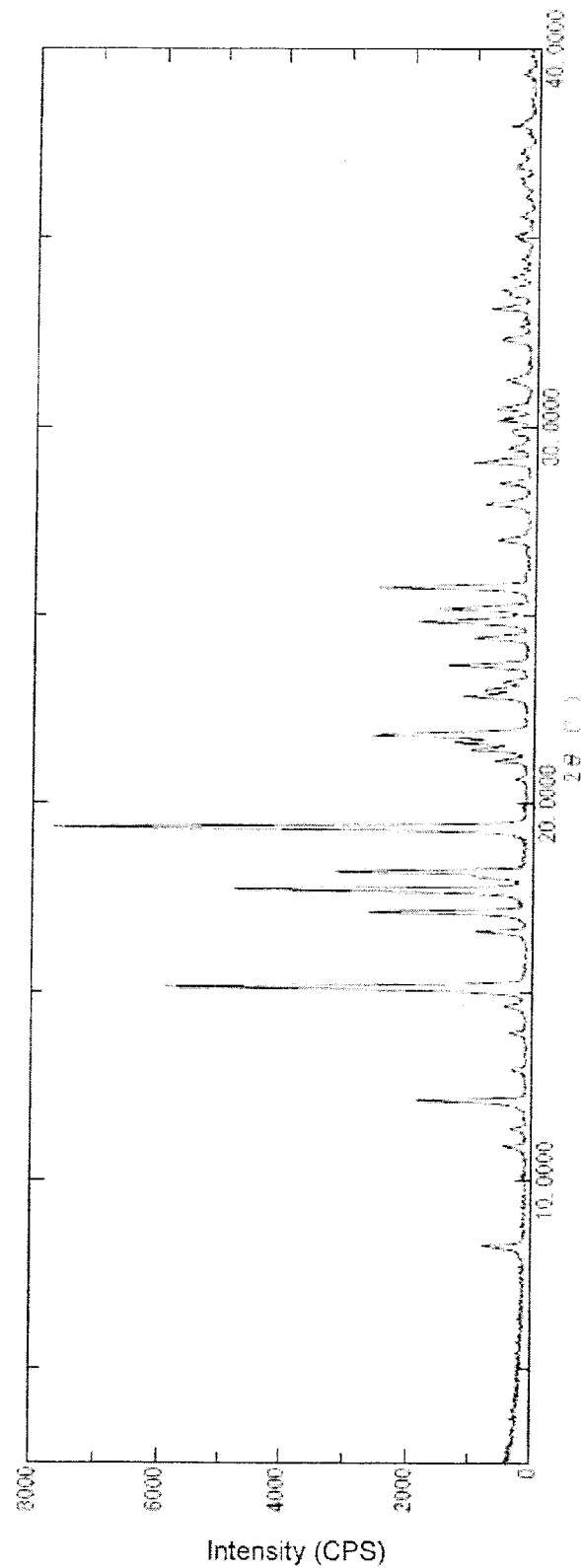
FIG. 5 shows a powder X-ray diffraction pattern of the compound of Example 118.

Hereinbelow, the present invention will be described in detail.

In the present specification, the "cardiovascular disease" refers to a disease based on the abnormal symptoms of circulatory organs such as heart, blood vessels, and the like. Among these, the "sGC-related cardiovascular disease" is known to be involved in an NO/sGC/cGMP system, and is a cardiovascular disease that can be treated or prevented by sGC activation. Examples thereof include hypertension, pulmonary hypertension, atherosclerosis, lumbar spinal canal stenosis, peripheral arterial disease, intermittent claudication, critical limb ischemia, stable or unstable angina pectoris, heart failure, thrombosis, stroke, sexual dysfunction, and the like. Here, examples of the peripheral arterial diseases include occlusive thrombotic vasculitis, peripheral arterial occlusive disease, Raynaud's disease, and Raynaud's syndrome.

The "peripheral arterial disease" is a disorder in which stenosis and occlusions caused by atherosclerosis, thrombosis and other impairments produce deficient blood flow, especially in the lower limbs. The symptoms are cold leg or feet, intermittent claudication, lower limb pain and critical limb ischemia (lower limb ulcers and necrosis). Diagnosis and treatment guidelines for peripheral arterial disease can be found in the following reference.
Eur. J. Vasc. Endovasc. Surg, 2007, 33(1), S1

"Intermittent claudication" means in one embodiment, intermittent claudication caused by peripheral arterial diseases, and in another embodiment intermittent claudication caused by peripheral arterial occlusive disease.

"Critical limb ischemia" means in one embodiment, critical limb ischemia caused by peripheral arterial diseases, and in another embodiment critical limb ischemia caused by peripheral arterial occlusive disease.

Further, the "sGC-related cardiovascular disease" means in one embodiment, hypertension or pulmonary hypertension.

The "hypertension" means, in one embodiment, essential hypertension, abnormal circadian blood pressure variability, renal parenchymal hypertension, renovascular hypertension, primary aldosteronism, Cushing's syndrome, hibernoma, or hypertension associated with endocrine diseases.

The "pulmonary hypertension" is, in one embodiment, pulmonary arterial pulmonary hypertension, pulmonary hypertension associated with heart diseases, pulmonary hypertension associated with lung diseases such as chronic obstructive pulmonary diseases or interstitial lung diseases, or pulmonary hypertension associated with chronic thrombotic or obstructive diseases.

Examples of the conditions for which the pharmaceutical composition of the present invention may be used include occlusive thrombotic vasculitis, peripheral arterial occlusive disease, intermittent claudication, critical limb ischemia, Raynaud's disease, Raynaud's syndrome, hypertension or pulmonary hypertension; in another embodiment, intermittent claudication associated with peripheral arterial diseases or critical limb ischemia; in still another embodiment, intermittent claudication associated with peripheral arterial diseases; and in still another embodiment, critical limb ischemia associated with peripheral arterial disease.

The "lower alkyl" is a monovalent group formed by the removal of any one hydrogen atom from a linear or branched saturated hydrocarbon having 1 to 6 carbon atoms (hereinafter simply referred to as $C_{1-6}$), and it is specifically methyl, ethyl, n-propyl, isopropyl, n-butyl, isobutyl, sec-butyl, tert-butyl, n-pentyl, n-hexyl, or the like; in another embodiment, $C_{1-4}$ alkyl; and in still another embodiment, methyl, ethyl, n-propyl, or isopropyl.

The "cycloalkyl having 3 to 8 carbon atoms" is a 3- to 8-membered monocyclic saturated hydrocarbon ring group, and specific examples thereof include cyclopropyl, cyclobutyl, cyclopentyl, cyclohexyl, cycloheptyl, and cyclooctyl, in a certain embodiment, cycloalkyl having 3 to 6 carbon atoms; and in another embodiment, cyclopropyl.

The "halogen" is F, Cl, Br, or I, in a certain embodiment, F or Cl; and in another embodiment, F.

The "halogeno-lower alkyl" is $C_{1-6}$ alkyl substituted with one or more halogen atom(s); in another embodiment, lower alkyl substituted with 1 to 5 halogen atom(s); in still another embodiment, trifluoromethyl; and in still another embodiment, difluoromethyl.

The "5- or 6-membered heteroaryl containing 1 to 4 heteroatoms selected from oxygen, sulfur, and nitrogen" is specifically pyridyl, pyrimidinyl, pyrazinyl, pyrrolyl, thienyl, furyl, thiazolyl, oxazolyl, pyrazolyl, imidazolyl, isoxazolyl, isothiazolyl, triazolyl, tetrazolyl, 1,2,4-oxadiazolyl, 1,2,4-thiadiazolyl, 1,3,4-thiadiazolyl, or 1,3,4-oxadiazolyl; in another embodiment, pyridyl, pyrimidinyl, thiazolyl, oxazolyl, pyrazolyl, tetrazolyl, 1,2,4-thiadiazolyl, 1,2,4-oxadiazolyl, 1,3,4-thiadiazolyl, or 1,3,4-oxadiazolyl; in another embodiment, thiazolyl, tetrazolyl, 1,2,4-oxadiazolyl, 1,3,4-oxadiazolyl, 1,3,4-thiadiazolyl, or tetrazolyl; in still another embodiment, tetrazolyl, 1,3,4-oxadiazolyl, or 1,3,4-thiadiazolyl; in still another embodiment, tetrazolyl; in still another embodiment, 1,3,4-oxadiazolyl; and in still another embodiment, 1,3,4-thiadiazolyl.

The "phenyl substituted with 1 to 3 F(s)" in $A^1$ is, for example, 2-fluorophenyl, 2,3-difluorophenyl, 2,6-difluorophenyl, 2,3,6-trifluorophenyl, or the like, in a certain embodiment, 2-fluorophenyl, 2,3-difluorophenyl, or 2,6-difluorophenyl; in another embodiment, 2,3-difluorophenyl; and in still another embodiment, 2,6-difluorophenyl.

Certain embodiments in the compound of the formula (I) or a salt thereof of the present invention are shown below.

(1) The compound or a salt thereof, in which $A^1$ is cyclohexyl, 2-fluorophenyl, 2,3-difluorophenyl, 2,6-difluorophenyl, or 3-fluoropyridin-2-yl; in another embodiment, the compound or a salt thereof, in which $A^1$ is cyclohexyl or 2,6-difluorophenyl; and in still another embodiment, the compound or a salt thereof, in which $A^1$ is 2,6-difluorophenyl.

(2) The compound or a salt thereof, in which R is a group represented by any one of (i), (ii), and (iv); in another embodiment, the compound or a salt thereof, in which R is a group represented by any one of (i), (iii), and (iv); in still another embodiment, the compound or a salt thereof, in which R is a group represented by (i) or (iv); and in still another embodiment, the compound or a salt thereof, in which R is a group represented by (iv).

(3) The compound or a salt thereof, in which $R^1$ is pyridyl, thiazolyl, oxazolyl, pyrazolyl, tetrazolyl, 1,3,4-thiadiazolyl, or 1,3,4-oxadiazolyl, each of which is substituted with the same or different 1 to 3 substituent(s) selected from the group consisting of $R^0$, $OR^0$, halogen-lower alkyl, cycloalkyl having 3 to 8 carbon atoms, and halogen; in still another embodiment, the compound or a salt thereof, in which $R^1$ is pyridyl, thiazolyl, oxazolyl, pyrazolyl, tetrazolyl, 1,3,4-thiadiazolyl, or 1,3,4-oxadiazolyl, each of which is substituted with the same or different 1 to 3 substituent(s) selected from the group consisting of methyl, ethyl, methoxy, cyclopropyl, difluoromethyl, and halogen; in still another embodiment, the compound or a salt thereof, in which $R^1$ is pyridyl, thiazolyl, or tetrazolyl, each of which is substituted with the same or different 1 or 2 substituent(s) selected from the group consisting of methyl, difluoromethyl, and halogen; and in still another embodiment, the compound or a salt thereof, in which $R^1$ is tetrazolyl substituted with difluoromethyl.

(4) The compound or a salt thereof, in which $R^2$ is F, $CH_2OH$, CONHMe, or $CON(Me)_2$; in still another embodiment, the compound or a salt thereof, in which $R^2$ is F or $CH_2OH$; and in still another embodiment, the compound or a salt thereof, in which $R^2$ is F.

(5) The compound or a salt thereof, in which
$R^3$ is pyridyl, thiazolyl, pyrazolyl, 1,2,4-triazolyl, 1,3,4-oxadiazolyl, or tetrazolyl, each of which is substituted with the same or different 1 to 3 substituent(s) selected from the group consisting of lower alkyl substituted with the same or different 1 to 3 substituent(s) selected from the group consisting of OH, $OR^0$ and halogen, cycloalkyl having 3 to 8 carbon atoms, $R^0$, and $OR^0$; in still another embodiment, the compound or a salt thereof, in which $R^3$ is pyridyl, thiazolyl, pyrazolyl, 1,3,4-oxadiazolyl, or tetrazolyl, each of which is substituted with the same or different 1 to 3 substituent(s) selected from the group consisting of methyl, ethyl, isopropyl, cyclopropyl, difluoromethyl, methoxy, hydroxyethyl, and methoxyethyl; and in still another embodiment, the compound or a salt thereof, in which $R^3$ is tetrazolyl substituted with ethyl or difluoromethyl.

(6) The compound or a salt thereof, in which $R^4$ is pyrimidinyl, pyrazinyl, thienyl, thiazolyl, oxazolyl, pyrazolyl, 1,2,3-triazolyl, 1,2,4-triazolyl, tetrazolyl, 1,2,4-oxadiazolyl, 1,3,4-thiadiazolyl, or 1,3,4-oxadiazolyl, each of which is unsubstituted or substituted with the same or different 1 to 3 substituent(s) selected from Group $D^1$;
pyridyl substituted with the same or different 1 to 3 substituent(s) selected from Group $D^1$; or
phenyl substituted with the same or different 1 to 4 substituent(s) selected from the group consisting of lower alkyl substituted with the same or different 1 to 3 substituent(s) selected from the group consisting of OH, $NH_2$, and $N(R^0)_2$, —O-(lower alkyl substituted with OH), $OR^0$, $CONH_2$, $CONHR^0$, $CON(R^0)_2$, CN, halogen, and (tetrazolyl which is unsubstituted or substituted with lower alkyl), in which
Group $D^1$ consists of lower alkyl substituted with the same or different 1 to 3 substituent(s) selected from the group consisting of OH, $OR^0$ and halogen, $R^0$, and cycloalkyl having 3 to 6 carbon atoms,
in still another embodiment, the compound or a salt thereof, in which $R^4$ is pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is unsubstituted;
pyridyl, pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, hydroxyethyl, 2-hydroxypropyl, 2-hydroxy-2-methylpropyl, methoxyethyl, difluoromethyl, trifluoromethyl, cyclopropyl, and cyclopropylmethyl; or
phenyl substituted with the same or different 1 or 2 substituent(s) selected from the group consisting of CN, $CH_2OH$, $CONH_2$, F, and (tetrazolyl which is unsubstituted or substituted with lower alkyl),
in still another embodiment, the compound or a salt thereof, in which $R^4$ is pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is unsubstituted; or
pyridyl, pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, hydroxyethyl, 2-hydroxypropyl, 2-hydroxy-2-methylpropyl, methoxyethyl, difluoromethyl, trifluoromethyl, cyclopropyl, and cyclopropylmethyl,
in still another embodiment, the compound or a salt thereof, in which $R^4$ is thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, difluoromethyl, and trifluoromethyl; or
phenyl substituted with 1 or 2 F(s),
in still another embodiment, the compound or a salt thereof, in which $R^4$ is thiazolyl, tetrazolyl, 1,3,4-thiadiazolyl, or 1,3,4-oxadiazolyl, each of which is substituted with the same or different 1 or 2 substituent(s) selected from the group consisting of methyl, ethyl, and difluoromethyl,
in still another embodiment, the compound or a salt thereof, in which $R^4$ is tetrazolyl, 1,3,4-thiadiazolyl, or 1,3,4-oxadiazolyl, each of which substituted with the same or different 1 or 2 substituent(s) selected from the group consisting of methyl and difluoromethyl,
in still another embodiment, the compound or a salt thereof, in which $R^4$ is 1,3,4-thiadiazolyl substituted with methyl,
in still another embodiment, the compound or a salt thereof, in which $R^4$ is 1,3,4-oxadiazolyl substituted with methyl, and
in still another embodiment, the compound or a salt thereof, in which $R^4$ is tetrazolyl substituted with difluoromethyl.

(7) The compound or a salt thereof, in which $R^5$ is H or methyl, and B is a benzene ring or a pyridine ring.

(8) The compound or a salt thereof, in which $R^6$ is pyridyl or thiazolyl, each of which is unsubstituted or substituted with the same or different 1 or 2 $R^0$(s); and in still another embodiment, the compound or a salt thereof, in which $R^6$ is pyridyl or thiazolyl, each of which is unsubstituted or substituted with 1 or 2 methyl group(s).

(9) A compound or a salt thereof, formed by combination of two or more groups as described in (1) to (8).

The present invention includes the compounds or salts thereof, formed by combination of any two or more in the embodiments described in (1) to (8), as described in (9), and specific examples thereof include the following embodiments.

(10) The compound represented by the formula (I) or a salt thereof, in which
$A^1$ is cyclohexyl, 2-fluorophenyl, 2,3-difluorophenyl, 2,6-difluorophenyl, or 3-fluoropyridin-2-yl,
$R^1$ is pyridyl, thiazolyl, oxazolyl, pyrazolyl, tetrazolyl, 1,3,4-thiadiazolyl, or 1,3,4-oxadiazolyl, each of which is substituted with the same or different 1 to 3 substituent(s) selected from the group consisting of $R^0$, $OR^0$, halogen-lower alkyl, cycloalkyl having 3 to 8 carbon atoms, and halogen,
$R^2$ is F, $CH_2OH$, CONHMe, or $CON(Me)_2$,
$R^3$ is pyridyl, thiazolyl, pyrazolyl, 1,2,4-triazolyl, 1,3,4-oxadiazolyl, or tetrazolyl, each of which is substituted with the same or different 1 to 3 substituent(s) selected from the group consisting of lower alkyl substituted with the same or different 1 to 3 substituent(s) selected from the group consisting of OH, $OR^0$ and halogen, cycloalkyl having 3 to 8 carbon atoms, $R^0$, and $OR^0$,
$R^4$ is pyrimidinyl, pyrazinyl, thienyl, thiazolyl, oxazolyl, pyrazolyl, 1,2,3-triazolyl, 1,2,4-triazolyl, tetrazolyl, 1,2,4-oxadiazolyl, 1,3,4-thiadiazolyl, or 1,3,4-oxadiazolyl, each of which is unsubstituted or substituted with the same or different 1 to 3 substituent(s) selected from Group $D^1$;
pyridyl substituted with the same or different 1 to 3 substituent(s) selected from Group $D^1$; or
phenyl substituted with the same or different 1 to 4 substituent(s) selected from the group consisting of lower alkyl substituted with the same or different 1 to 3 substituent(s) selected from the group consisting of OH, $NH_2$ and $N(R^0)_2$, —O-(lower alkyl substituted with OH), $OR^0$, $CONH_2$, $CONHR^0$, $CON(R^0)_2$, CN, halogen, and (tetrazolyl which is unsubstituted or substituted with lower alkyl),
Group $D^1$ consists of lower alkyl substituted with the same or different 1 to 3 substituent(s) selected from the group consisting of OH, $OR^0$ and halogen, $R^0$, and cycloalkyl having 3 to 6 carbon atoms,
$R^5$ is H or methyl, and
$R^6$ is pyridyl or thiazolyl, each of which is unsubstituted or substituted with the same or different 1 or 2 $R^0$(s).

(11) The compound or a salt thereof as described in (10), in which $R^1$ is pyridyl, thiazolyl, oxazolyl, pyrazolyl, tetrazolyl, 1,3,4-thiadiazolyl, or 1,3,4-oxadiazolyl, each of which is substituted with the same or different 1 to 3 substituent(s) selected from the group consisting of methyl, ethyl, methoxy, cyclopropyl, difluoromethyl, and halogen,
$R^2$ is F or $CH_2OH$,
$R^3$ is pyridyl, thiazolyl, pyrazolyl, 1,3,4-oxadiazolyl, or tetrazolyl, each of which is substituted with the same or different 1 to 3 substituent(s) selected from the group consisting of methyl, ethyl, isopropyl, cyclopropyl, difluoromethyl, methoxy, hydroxyethyl, and methoxyethyl,
$R^4$ is pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is unsubstituted;
pyridyl, pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, hydroxyethyl, 2-hydroxypropyl, 2-hydroxy-2-methylpropyl, methoxyethyl, difluoromethyl, trifluoromethyl, cyclopropyl, and cyclopropylmethyl; or
phenyl substituted with the same or different 1 or 2 substituent(s) selected from the group consisting of CN, $CH_2OH$, $CONH_2$, F, and (tetrazolyl which is unsubstituted or substituted with lower alkyl),
$R^6$ is pyridyl or thiazolyl, each of which is unsubstituted or substituted with 1 or 2 methyl group(s).

(12) The compound or a salt thereof as described in (11), in which R is represented by the formula (iv),
$R^4$ is pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is unsubstituted; or
pyridyl, pyrimidinyl, thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, hydroxyethyl, 2-hydroxypropyl, 2-hydroxy-2-methylpropyl, methoxyethyl, difluoromethyl, trifluoromethyl, cyclopropyl, and cyclopropylmethyl.

(13) The compound or a salt thereof as described in (11), in which $A^1$ is 2,6-difluorophenyl,
R is a group represented by any one of the formulae (i), (iii), and (iv),
$R^1$ is pyridyl, thiazolyl, or tetrazolyl, each of which is substituted with the same or different 1 or 2 substituent(s) selected from the group consisting of methyl, difluoromethyl, and halogen,
$R^3$ is tetrazolyl substituted with ethyl or difluoromethyl, and
$R^4$ is thiazolyl, oxazolyl, pyrazolyl, tetrazolyl, 1,2,4-oxadiazolyl, 1,3,4-thiadiazolyl, or 1,3,4-oxadiazolyl, each of which is substituted with the same or different 1 or 2 substituent(s) selected from the group consisting of methyl, ethyl, hydroxymethyl, difluoromethyl, and trifluoromethyl; or
phenyl substituted with 1 or 2 F(s).

(14) The compound or a salt thereof as described in (11), in which
$A^1$ is 2,6-difluorophenyl,
R is a group represented by any one of the formulae (i), (ii), and (iv),
$R^1$ is tetrazolyl substituted with difluoromethyl,
$R^2$ is F, and
$R^4$ is thiazolyl, tetrazolyl, 1,3,4-thiadiazolyl, or 1,3,4-oxadiazolyl, each of which is substituted with the same or different 1 or 2 substituent(s) selected from the group consisting of methyl, ethyl and difluoromethyl.

(15) The compound or a salt thereof as described in (11), in which
$A^1$ is 2,6-difluorophenyl,
R is a group represented by any one of the formulae (i) and (iv),
$R^1$ is tetrazolyl substituted with difluoromethyl, and
$R^4$ is tetrazolyl, 1,3,4-thiadiazolyl, or 1,3,4-oxadiazolyl, each of which is substituted with the same or different 1 or 2 substituent(s) selected from the group consisting of methyl and difluoromethyl.

(16) The compound or a salt thereof as described in (15), in which
R is a group represented by the formula (i), and
$R^1$ is tetrazolyl substituted with difluoromethyl.

(17) The compound or a salt thereof as described in (15), in which R is a group represented by the formula (iv), and
$R^4$ is 1,3,4-thiadiazolyl substituted with methyl.

(18) The compound or a salt thereof as described in (15), in which
R is a group represented by the formula (iv), and
R⁴ is 1,3,4-oxadiazolyl substituted with methyl.
(19) The compound or a salt thereof as described in (15), in which
R is a group represented by the formula (iv), and
R⁴ is tetrazolyl substituted with difluoromethyl.

The compound of the formula (I) may exist in the form of tautomers or geometrical isomers depending on the kind of substituents. In the present specification, the compound of the formula (I) shall be described in only one isomer form, yet the present invention includes any other isomers, in their isolated form, or as mixtures thereof.

Furthermore, the compound of the formula (I) may have asymmetric carbon and optical isomers exist based on the chiral carbon. In addition, the compound of the formula (I) may have chiral carbon atoms or axis chirality in some cases, depending on the kind of the substituent, and therefore, optical isomers may exist based thereon. The present invention includes both isolated forms of each of the optical isomers of the compound of the formula (I) or a mixture thereof, including racemic compounds thereof, at an arbitrary ratio. Here, the racemic compound is a mixture of an optically active substance and its enantiomer (mirror image isomer) at a ratio of 1:1, and means an optically inactive compound. However, in the context, a compound starting with "rac-" in the chemical name denotes that it is a racemic compound.

Other embodiments of the present invention are shown below.

In a certain embodiment, the present invention includes the compounds selected from the following group consisting of:
8-[(2,6-difluorobenzyl)oxy]-N-[1-hydroxy-2-(5-methyl-1,2,4-oxadiazol-3-yl)propan-2-yl]-2-methylimidazo[1,2-a]pyridine-3-carboxamide,
8-[(2,6-difluorobenzyl)oxy]-N-[(2S)-1-hydroxy-2-(5-methyl-1,3-thiazol-2-yl)propan-2-yl]-2-methylimidazo[1,2-a]pyridine-3-carboxamide,
8-[(2,6-difluorobenzyl)oxy]-N-{1-hydroxy-2-[5-(trifluoromethyl)-1,3,4-oxadiazol-2-yl]propan-2-yl}-2-methylimidazo[1,2-a]pyridine-3-carboxamide, and
8-[(2,6-difluorobenzyl)oxy]-N-[(2R)-1-hydroxy-2-(2-methyl-2H-tetrazol-5-yl)propan-2-yl]-2-methylimidazo[1,2-a]pyridine-3-carboxamide,
or a salt thereof.

In another embodiment, the present invention includes the compounds selected from the following group consisting of:
8-[(2,6-difluorobenzyl)oxy]-N-[1-hydroxy-2-(2-methyl-1,3-thiazol-5-yl)propan-2-yl]-2-methylimidazo[1,2-a]pyridine-3-carboxamide,
8-[(2,6-difluorobenzyl)oxy]-N-[2-(2-ethyl-2H-tetrazol-5-yl)-1-hydroxypropan-2-yl]-2-methylimidazo[1,2-a]pyridine-3-carboxamide, and
8-[(2,6-difluorobenzyl)oxy]-N-[2-(4-fluorophenyl)-1,3-dihydroxypropan-2-yl]-2-methylimidazo[1,2-a]pyridine-3-carboxamide,
or a salt thereof In still another embodiment, the present invention includes the compounds selected from the following group consisting of:
8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide,
8-[(2,6-difluorobenzyl)oxy]-N-[(2S)-1-hydroxy-2-(5-methyl-1,3,4-oxadiazol-2-yl)propan-2-yl]-2-methylimidazo[1,2-a]pyridine-3-carboxamide,
8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide, and
8-[(2,6-difluorobenzyl)oxy]-N-[(2S)-1-hydroxy-2-(5-methyl-1,3,4-thiadiazol-2-yl)propan-2-yl]-2-methylimidazo[1,2-a]pyridine-3-carboxamide,
or a salt thereof.

Moreover, the present invention also includes a pharmaceutically acceptable prodrugs of the compound of formula (I). Pharmaceutically acceptable prodrugs are compounds having groups that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Drug Design, 163-198.

Furthermore, salts of the compound of formula (I) are pharmaceutically acceptable salts of the compound of formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, phosphoric acid, and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, glutamic acid, and the like, and salts with inorganic bases such as sodium, potassium, magnesium, calcium, aluminum, and the like or organic bases such as methylamine, ethylamine, ethanolamine, lysine, ornithine, and the like, salts with various amino acids or amino acid derivatives such as acetylleucine and the like, ammonium salts, etc.

In addition, the present invention also includes various hydrates or solvates, co-crystal and polymorphic crystal polymorph of the compound of formula (I) or a salt thereof. In addition, the present invention also includes compounds labeled with various radioactive or non-radioactive isotopes.

(Preparation Methods)

The compound of the formula (I) and a salt thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage of starting materials or intermediates may be effective depending on the type of the functional group in the production technology in some cases. The protective group for such a functional group may include, for example, the protective groups described in "Greene's Protective Groups in Organic Synthesis (4$^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, prodrugs of the compound of the formula (I) can be prepared by introducing a specific group at the stage from a starting material to an intermediate or by carrying out the reaction using the obtained compound of the formula (I), just as in the case of the above-mentioned protective group. The reaction can be carried out using methods known to a person skilled in the art, such as ordinary esterification, amidation, dehydration, and the like.

Hereinbelow, representative preparation methods for the compound of the formula (I) will be described. Each production process may also be carried out with reference to the References appended in the present description. Further, the preparation methods of the present invention are not limited to the examples as shown below.
(General Production Processes)
(Production Process 1)

[Chem. 11]

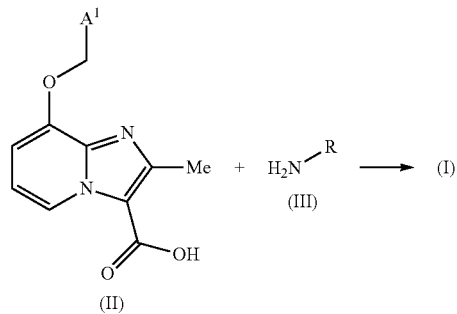

The compound of the formula (I) can be prepared by reacting a carboxylic acid compound (II) with an amine compound (III). Further, in this production process, the compounds (II) and (III) may have their functional groups protected with a protective group as desired, and may be subjected to a deprotection reaction after the reaction and/or a modification reaction of a group known to a person skilled in the art, thus to prepare the compound of the formula (I).

In this production process, the compound of the formula (II) and the compound of the formula (III) are used in equivalent amounts, or either thereof in an excess amount, and their mixture is stirred in a range of from cooling to heating, preferably at a temperature from −20° C. to 60° C., usually for about 0.1 hours to 5 days, in a solvent which is inert to the reaction, in the presence of a condensing agent. The solvent as used herein is not particularly limited, but examples thereof include aromatic hydrocarbons such as benzene, toluene, xylene, and the like, halogenated hydrocarbons such as dichloromethane, 1,2-dichloroethane, chloroform, and the like, ethers such as diethyl ether, tetrahydrofuran (THF), dioxane, dimethoxyethane, and the like, N,N-dimethylformamide (DMF), N,N-dimethylacetamide (DMAc), dimethylsulfoxide (DMSO), ethyl acetate, acetonitrile, water, and any mixture thereof. Examples of the condensing agent include, but are not limited to, 1-(3-dimethylaminopropyl)-3-ethylcarbodiimide (WSC), dicyclohexylcarbodiimide (DCC), 1,1'-carbonyldiimidazole (CDI), diphenylphosphoryl azide (DPPA), and phosphorous oxychloride. In some cases, it may be preferable for the reaction to use an additive (for example, 1-hydroxybenzotriazole (HOBt)). It may be advantageous for a smooth progression of the reaction in some cases to carry out the reaction in the presence of organic bases such as triethylamine (TEA), N,N-diisopropylethylamine (DIPEA), 4-dimethyaminolpyridine, N-methylmorpholine (NMM), and the like or inorganic bases such as potassium carbonate, sodium carbonate, potassium hydroxide and the like.

Furthermore, it is also possible to use a method in which the compound of the formula (II) is converted to a reactive derivative thereof and then reacted with the compound of the formula (III). Examples of reactive derivatives of the compound of the formula (II) include acid halides that can be obtained by the reaction with a halogenating agent such as phosphorus oxychloride, thionyl chloride, oxalyl chloride, or the like, mixed acid anhydrides obtained by the reaction with isobutyl chloroformate or the like, and active esters obtained by condensation with 1-hydroxybenzotriazole or the like. The reaction of these reactive derivatives with the compound of the formula (III) can be carried out in a range of from cooling to heating, and preferably at a temperature from −20° C. to 60° C., in a solvent which is inert to the reaction, such as halogenated hydrocarbons, aromatic hydrocarbons, ethers, and the like. For this reaction, for example, the following references may be referred to.

"Organic Functional Group Preparations", S. R. Sandler and W. Karo, $2^{nd}$ edition, Vol. 1, Academic Press Inc., 1991

The Chemical Society of Japan, "Courses in Experimental Chemistry ($5^{th}$ edition)" Vol. 16 (2005) (Maruzen)

In addition, another compound of the formula (I) can also be prepared, using the compound of the formula (I) prepared by this Production Process as a staring material, by subjecting the compound to a modification reaction of a functional group, which is well-known or apparent to a person skilled in the art.

(Production Process 2)

[Chem. 12]

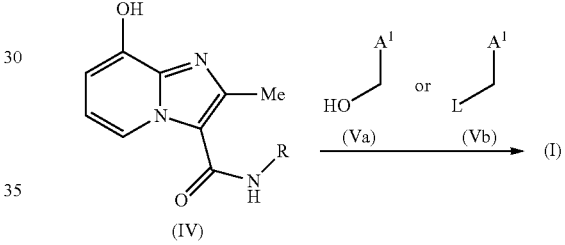

(wherein L represents a leaving group, for example, halogen).

Furthermore, the compound of the formula (I) can be prepared by reacting a compound of the formula (IV) with a compound of the formula (Va) or a compound of the formula (Vb).

In the case of using the compound of the formula (Va), a so-called Mitsunobu reaction such as a method in which known azodicarboxylic esters or azodicarboxylic amides as a reagent are used in combination with known phosphines, and a method in which (tributylphosphoraniliden) acetonitrile (Tsunoda reagent) or the like is used, or a modified method thereof may be used and these are reactions known to those skilled in the art.

In this reaction, the compound of the formula (IV) and the compound of the formula (Va) are used in equivalent amounts, or either thereof in an excess amount, and their mixture is stirred in a range of from cooling to heating to refluxing, preferably at a temperature from 0° C. to 150° C., usually for about 0.1 hours to 5 days, in a solvent which is inert to the reaction. The solvent as used herein is not particularly limited, but examples thereof include aromatic hydrocarbons, ethers, halogenated hydrocarbons, DMF, DMSO, ethyl acetate, acetonitrile, and a mixture thereof.

For this reaction, for example, the following references may be referred to.

Mitsunobu, O.; Synthesis (1981), 1

Tsunoda, T. et al., Tetrahedron Letters (1995) 36, 2529, ibid, (1996) 37, 2463

On the other hand, in the production process in which the compound of the formula (Vb) is used, the compound of the formula (IV) and the compound of the formula (Vb) are used in equivalent amounts, or either thereof in an excess amount, and their mixture is stirred in a range of from cooling to heating to refluxing, preferably at a temperature from 0° C. to 80° C., usually for about 0.1 hours to 5 days, in a solvent which is inert to the reaction, in the presence of a base. The solvent as used herein is not particularly limited, but examples thereof include aromatic hydrocarbons, ethers, halogenated hydrocarbons, DMF, DMSO, ethyl acetate, acetonitrile, and a mixture thereof. Examples of the base include organic bases such as triethylamine, diisopropylethylamine, 1,8-diazabicyclo[5.4.0]-7-undecene, n-butyllithium, and the like, and inorganic bases such as sodium carbonate, potassium carbonate, sodium hydride, potassium tert-butoxide, and the like. It may be advantageous in some cases to carry out the reaction in the presence of a phase transfer catalyst such as tetra-n-butylammonium chloride.

For this reaction, for example, the following references may be referred to.

"Organic Functional Group Preparations", S. R. Sandler and W. Karo, 2$^{nd}$ edition, Vol. 1, Academic Press Inc., 1991

The Chemical Society of Japan, "Courses in Experimental Chemistry (5$^{th}$ edition)" Vol. 14 (2005) (Maruzen)

In the preparation method above, the starting compound can be prepared by using, for example, the methods below, the methods described in Preparation Examples, which will be described later, known methods, or modified methods thereof.

(Starting Material Synthesis 1)

[Chem. 13]

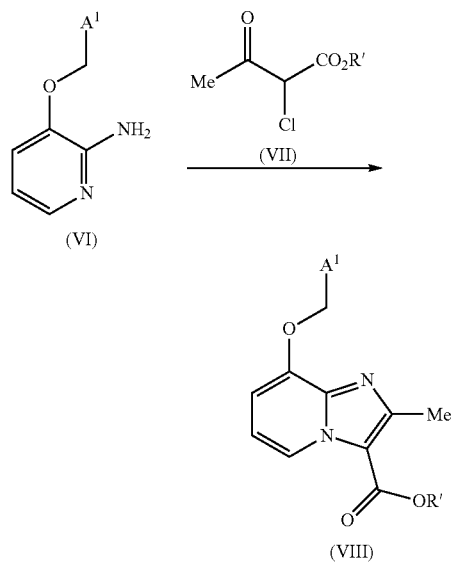

(wherein R' is lower alkyl or the like, for example, methyl or ethyl).

The compound of the formula (II) which is a starting material can be prepared by reacting a compound of the formula (VI) with a compound of the formula (VII) to prepare a compound of the formula (VIII), which is then subjected to hydrolysis.

For the reaction for preparing the compound of the formula (VIII), the compound of the formula (VI) and the compound of the formula (VII) are used in equivalent amounts, or either thereof in an excess amount, and their mixture is stirred in a range of from room temperature to heating, preferably at a temperature from 60° C. to 150° C., usually for about 0.1 hours to 5 days, in a solvent which is inert to the reaction. The solvent as used herein is not particularly limited, but examples thereof include aromatic hydrocarbons such as benzene, toluene, xylene, and the like, halogenated hydrocarbons such as 1,2-dichloroethane, chloroform, and the like, ethers such as dioxane, dimethoxyethane, and the like, N,N-dimethylformamide (DMF), N,N-dimethylacetamide, dimethylsulfoxide, ethyl acetate, acetonitrile, water, and any mixture thereof. Further, it may be advantageous for a smooth progression of the reaction in some cases to carry out the reaction in the presence of organic bases such as triethylamine, N,N-diisopropylethylamine, 4-dimethylaminopyridine, pyridine, 2,6-lutidine, N-methylmorpholine (NMM), and the like, or inorganic bases such as potassium carbonate, sodium carbonate, potassium hydroxide, and the like.

The hydrolysis reaction for preparing the compound of the formula (II) from the compound of the formula (VIII) can be carried out by a known method or a method apparent to a person skilled in the art.

(Starting Material Synthesis 2)

[Chem. 14]

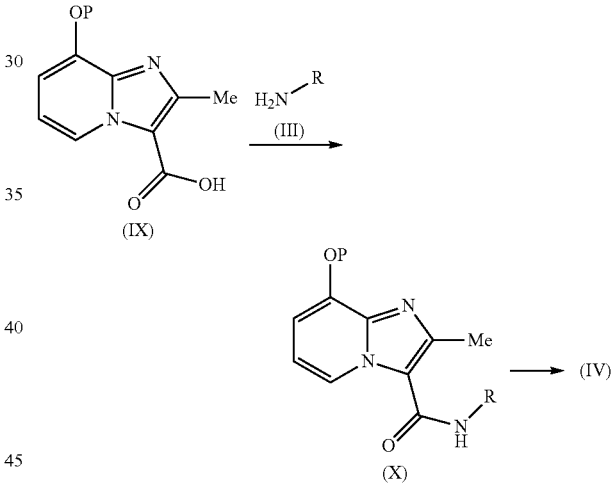

(wherein P is a protective group, for example, benzyl).

The starting compound (IV) can be prepared by reacting a compound (IX) and a compound (III) to prepare a compound (X), which is then subjected to deprotection. The reaction of the compound (IX) with the compound (III) can be carried out in the same way as in Production Process 1 as described above. Further, the deprotection can be carried out by a known method or a method apparent to a person skilled in the art.

The compounds of the formula (I) are isolated and purified as free compounds, salts, hydrates, solvates, or polymorphic crystal polymorph thereof. Salts of the compound of the formula (I) can be prepared by conventional salt forming reactions.

Isolation and purification are carried out by employing ordinary chemical operations such as extraction, fractional crystallization, and fractional chromatography, and the like.

The compound of the formula (I) may exist in some cases as optical isomers based on the asymmetric carbon, depending on the kind of the substituent. Various isomers in the present invention can be prepared by selecting appropriate starting compounds or by separation using the difference in physicochemical properties between the isomers. For example, optical isomers can be obtained by means of a general optical resolution method for racemic products (for example, fractional crystallization for inducing diastereomer salts with optically active bases or acids, chromatography using a chiral column or the like, and others), and further, the isomers can also be prepared from an appropriate optically active starting compound.

Test Examples

Pharmacological activities of the compound of the formula (I) were confirmed in the following tests.

Further, for the sake of convenience, a concentration mol/l is expressed as M. For example, a 1 M aqueous sodium hydroxide solution means a 1 mol/l aqueous sodium hydroxide solution.

Test Example 1 sGC Activation Test

The activity of sGC was evaluated by measuring the amount of cGMP produced by human purified sGC.

Using an sGCα1 gene (NCBI accession No. BC028384.2) and an sGCβ1 gene (NCBI accession No. BC047620.1), an N-terminal FLAG tag-fused sGCα1 and an sGCβ1 expression baculovirus were prepared. These viruses were transfected into insect cells Sf9 (Cat. No. 11496-015, Gibco) to express a protein. From the cell lysates of the insect cells, heterodimers of the N-terminal FLAG tag-fused sGCα1 and sGCβ1 were purified with an M2 Affinity Gel (Sigma-Aldrich, Inc.) to obtain a human sGC.

An Example compound was dissolved in DMSO and diluted 20-fold with ultrapure water. 2 μL of the diluted Example compound solution (maximum concentration of 100 μM), 2 μL of a substrate solution [0.5 μM triethanolamine buffer solution, 0.03 μM dithiothreitol, 0.01 μM GTP, 0.04 μM $MgCl_2$, and 0.03 μM sodium nitroprusside (SNP)], and 6 μL of a human enzyme suspension were added to 384-well plates (manufactured by Greiner Bio-One), and incubated at room temperature for one hour. The measurement of the amount of cGMP was carried out, using an HTRF reagent (Cisbio).

The sGC activation action of the Example compound was calculated as an Example compound concentration which gives 50% of a maximum activity ($EC_{50}$), in which the maximum activity by the addition of a compound shown in Preparation Example 200, 8-(cyclohexylmethoxy)-N-[(1R)-2-hydroxy-1-phenylethyl]-2-methylimidazo[1,2-a]pyridine-3-carboxamide hydrochloride (maximum 100 μM), is taken as 100%. Further, the maximum activity of sGC with the addition of 8-(cyclohexylmethoxy)-N-[(1R)-2-hydroxy-1-phenylethyl]-2-methylimidazo[1,2-a]pyridine-3-carboxamide hydrochloride is 10-fold or more relative to the sGC activation without the addition of the compound, and it is recognized that the compound has a good sGC activating action. In addition, the maximum activity with the addition of a known sGC activator YC-1 (lificiguat, [5-(1-benzyl-1H-indazol-3-yl)-2-furyl]methanol) was 52% of the maximum activity with the addition of 8-(cyclohexylmethoxy)-N-[(1R)-2-hydroxy-1-phenylethyl]-2-methylimidazo[1,2-a]pyridine-3-carboxamide hydrochloride, and the $EC_{50}$ value of the YC-1 was 50 μM. The test results of some Example compounds that are the compounds of the formula (I) of the present invention are shown below. Further, in Tables, Ex. represents Example number.

TABLE 1

| Ex. | $EC_{50}$ (μM) |
|---|---|
| 1 | 5.5 |
| 2 | 2.6 |
| 3 | 0.72 |
| 4 | 1.4 |
| 5 | 6.4 |
| 6 | 1.7 |
| 7a | 9.6 |
| 8 | 5.7 |
| 9 | 0.72 |
| 11 | 1.3 |
| 12 | 0.78 |
| 13 | 0.84 |
| 14 | 4.4 |
| 15 | 2.8 |
| 16 | 2.1 |
| 18 | 1.6 |
| 19 | 3.6 |
| 21 | 4.0 |
| 23 | 9.8 |
| 24 | 3.6 |
| 26 | 24 |
| 27 | 12 |
| 28 | 13 |
| 29 | 17 |
| 30 | 5.6 |
| 31 | 4.9 |
| 32 | 8.2 |
| 33 | 7.4 |
| 34 | 11 |
| 35 | 6.4 |
| 36 | 11 |
| 37 | 7.1 |
| 38 | 2.5 |
| 39 | 4.6 |
| 40 | 3.8 |
| 41 | 5.3 |
| 42 | 33 |
| 43 | 14 |
| 44 | 16 |
| 45 | 9.1 |
| 46 | 20 |
| 47 | 13 |
| 48 | 2.7 |
| 49 | 25 |
| 50 | 7.9 |
| 51 | 12 |
| 52 | 2.2 |
| 53 | 1.7 |
| 54 | 2.7 |
| 55 | 2.0 |
| 56 | 8.5 |
| 57 | 3.7 |
| 58 | 3.3 |
| 59 | 1.9 |
| 60 | 12 |
| 61 | 6.4 |
| 62 | 6.5 |
| 64 | 30 |
| 66 | 16 |
| 67 | 24 |
| 68 | 14 |
| 69 | 4.6 |
| 70 | 3.8 |
| 71 | 21 |
| 72 | 2.7 |
| 73a | 6.4 |
| 74 | 12 |
| 75 | 9.1 |
| 76 | 5.8 |
| 77 | 1.3 |

TABLE 2

| Ex. | EC$_{50}$ (μM) |
|---|---|
| 78 | 5.1 |
| 80 | 7.1 |
| 83 | 2.7 |
| 84 | 7.1 |
| 85 | 2.9 |
| 86 | 5.6 |
| 87 | 5.9 |
| 88 | 5.3 |
| 89 | 11 |
| 90 | 9.8 |
| 91 | 1.5 |
| 92 | 1.4 |
| 93 | 21 |
| 94 | 14 |
| 95 | 18 |
| 96 | 3.4 |
| 97 | 3.5 |
| 98 | 24 |
| 99 | 17 |
| 100 | 20 |
| 101 | 26 |
| 102 | 2.6 |
| 103 | 6.1 |
| 104 | 7.5 |
| 105 | 11 |
| 106 | 9.1 |
| 107a | 1.5 |
| 108a | 4.6 |
| 109 | 23 |
| 110 | 12 |
| 111 | 0.56 |
| 81 | 16 |
| 82 | 21 |
| 114 | 0.73 |
| 117 | 5.5 |
| 118 | 1.1 |

Test Example 2

Blood Flow Increasing Action In Vivo

The hind limb blood flow increasing action in rats anesthetized with pentobarbital was confirmed by the following test method.

Wistar male rats, 11- to 14-week (Japan SLC, Inc.) were used. An administration liquid was prepared by adding N,N-dimethyl formamide, Polyethylene Glycol 400, TWEEN 80, a 0.5% methyl cellulose aqueous solution, a 0.5 M aqueous sodium hydrogen carbonate solution, and 0.1 M hydrochloric acid to the test compound and dissolving the Example compound in an appropriate manner depending on the compound. The prepared administration liquid was orally administered, and 2 hours later, the hind limb blood flow increasing action was evaluated under anesthesia with intraperitoneally administration of 60 mg/kg of pentobarbital The hind limb blood flow was measured using a laser blood flow imaging device (PIM II Integral). By taking the average blood flow rate of a group with the administration of a solvent as 100%, the compound was evaluated to be effective when the blood flow rate was 130% or more by the administration of the compound.

The compounds of Examples 2, 7a, 8, 31, 40, 52, 54, 67, 69, 76, and 107a of the present invention exhibited a blood flow increasing action at a dose of 3 mg/kg. Further, the compounds of Examples 1, 11, 18, 19, 36, 37, 38, 39, 70, 72, 81, 83, and 118 exhibited a blood flow increasing action at a dose of 1 mg/kg. Further, the compounds of Examples 9, 35, 41, 77, 91, 96, and 108a exhibited a blood flow increasing action at a dose of 0.3 mg/kg. In addition, the compounds of Examples 6 and 117 exhibited a blood flow increasing action at a dose of 0.1 mg/kg, and the compound of Example 114 exhibited a blood flow increasing action at a dose of 0.03 mg/kg.

Test Example 3

Measurement of Antihypertensive Effect In Vivo

As the animals, Wistar male rats, 13- to 18-week (Japan SLC, Inc.) were used. Three days prior to administration of a test compound, a cannula (PE-50, Becton, Dickinson and Company, Japan) filled with heparin physiological saline (200 U/mL, Ajinomoto Pharmaceuticals Co., Ltd.) was inserted and placed in the common carotid artery under anesthesia with intraperitoneal administration of 60 mg/kg of pentobarbital. The other end of the cannula was subcutaneously exposed to the back of the neck. After the recovery period, the placed cannula was connected to a pressure transducer (Life Kit DTS DX-100, Nihon Kohden Corporation) to record the blood pressure waveform through an amplifier (AP-641G, Nihon Kohden Co., Ltd.) and PowerLab (ML870 PowerLab8/30 (AD Instruments Japan)). The heart rate was calculated using a heart rate measuring unit (AT-601G, Nihon Kohden Co., Ltd.). After stabilization of the blood pressure, the test compound was orally administered one time to measure the blood pressure and the heart rate over time. The test compounds were administered by appropriately adding N,N-dimethylformamide, Polyethylene Glycol 400, TWEEN 80, a 0.5% aqueous methylcellulose solution, and a 0.5 M aqueous sodium hydrogen carbonate solution, and 0.1 M hydrochloric acid therein according to the compounds and dissolving it.

The test results are shown below. Further, the administration doses in Tables represent the administration doses for oral administration, and for example, 3 means 3 mg/kg. Further, the blood pressure reduction represents a maximum change value from the value before administration in the average blood pressure, and for example, −63 indicates reduction by 63 mmHg.

TABLE 3

| Ex. | Administration dose | Blood pressure reduction |
|---|---|---|
| 2 | 3 | −56 |
| 8 | 3 | −29 |
| 9 | 3 | −63 |
| 54 | 3 | −56 |
| 96 | 1 | −21 |
| 114 | 0.3 | −35 |
| 117 | 1 | −35 |
| 118 | 3 | −61 |

From the results of Test Example 1 above, the sGC activation action of the compounds of the present invention was confirmed. Further, it was confirmed that several compounds have a blood flow increasing action, and thus have an increasing action as shown in Test Example 2. Since the blood flow improving action is effective for the treatment of peripheral arterial diseases, it is expected that the compound of the formula (I) can be used for treating sGC-related cardiovascular diseases, in particular, peripheral arterial diseases, as well as intermittent claudication and critical limb ischemia accompanied with peripheral arterial diseases, or the like.

In addition, the antihypertensive action was confirmed for the several Example compounds, and thus, it was confirmed that a plurality of the Example compounds of the present invention have an antihypertensive action as shown in Test Example 3 above. Accordingly, it is expected that the compound of the formula (I) can be used for treating hypertension, or the like.

Pharmaceutical compositions containing one or more kinds of compound of formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredient(s) are mixed with at least one inactive excipient. In a conventional method, the composition may contain inactive additives, such as lubricants, disintegrating agents, stabilizers, or solubilization assisting agents. If necessary, tablets or pills may be coated with sugar or s gastric- or enteric-soluble substances films.

Liquid compositions for oral administration comprises pharmaceutically acceptable emulsions, solutions, suspensions, syrups, elixirs, or the like, and also comprises generally used inert diluents, for example, purified water or ethanol (EtOH). In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to its use.

Agents for external use includes ointments, plasters, creams, jellies, poultices, sprays, lotions, eye drops, eye ointments, and the like. The agents contain generally used ointment bases, lotion bases, aqueous or non-aqueous solutions, suspensions, emulsions, and the like.

As transmucosal agents such as inhalers, transnasal agents, and the like, those in the form of a solid, liquid, or semi-solid state are used, and can be prepared in accordance with conventionally known methods. For example, known excipients, and furthermore pH adjusting agents, antiseptics, surfactants, lubricants, stabilizers, thickening agents, or the like may be appropriately added thereto. For their administration, appropriate devices for inhalation or blowing can be used. For example, a compound may be administered alone or as a powder of formulated mixture, or as a solution or suspension in combination with pharmaceutically acceptable carriers, using a known device or sprayer, such as a measured administration inhalation device, and the like. Dry powder inhalers or the like may be for single or multiple administration use, and dry powder or powder-containing capsules may be used. Alternatively, these may be pressurized aerosol spray which uses appropriate ejection agents, for example, a suitable gas such as chlorofluoroalkane, hydrofluoroalkane, carbon dioxide, and the like.

For oral administration, daily dose is generally from about 0.001 to 100 mg/kg, preferably from 0.1 to 30 mg/kg, and more preferably from 0.1 to 10 mg/kg, per body weight, administered in one portion or in 2 to 4 separate portions. In the case of intravenous administration, daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. Doses are appropriately determined according to the individual according to the symptoms, age, gender, and the like.

Although varying depending on administration routes, dosage forms, administration sites, or the types of excipients and additives, the pharmaceutical composition of the present invention contains 0.01 to 100% by weight, and in a certain embodiment, 0.01 to 50% by weight of one or more kinds of the compound of formula (I) or a salt thereof, as the active ingredient.

The compound of formula (I) can be used in combination with various therapeutic or prophylactic agents for the diseases for which the compound of formula (I) is considered to be effective, as described above. The combined preparation may be administered simultaneously, or separately and continuously, or at a desired time interval. The preparations to be administered simultaneously may be a mixture, or may be prepared individually.

EXAMPLES

Hereinbelow, the preparation methods for the compound of formula (I) will be described in more detail with reference to Examples. The present invention is not limited to the compounds described in Examples as described below. Further, the production processes for the starting compounds will be described in Preparation Examples. The compound of formula (I) is prepared by using a combination of the preparation methods or a method apparent to a person skilled in the art, in addition to Production Processes described in Examples.

Moreover, the following abbreviations may be used in some cases in Examples, Preparation Examples, and Tables as described later.

PEx: Preparation Example number, Ex: Example number, No.: Compound number, Str: Structural formula, DATA: Physicochemical data (ESI+: ESI-MS [M+H]$^+$ or ESI-MS [M]$^+$; ESI−: ESI-MS [M−H]$^−$; CI+: CI-MS [M+H]$^+$; EI: EI [M]$^+$; APCI/ESI+: APCI/ESI-MS [M+H]$^+$ or APCI/ESI-MS [M]$^+$ (APCI/ESI means simultaneous measurement of APCI and ESI); NMR: δ (ppm) of a peak in $^1$H-NMR, and unless otherwise described, 400 MHz), Me: methyl, Et: ethyl, tBu: tert-butyl, cPr: cyclopropyl, iPr: isopropyl, cHex: cyclohexyl, Ph: phenyl, Bn: benzyl, Ac: acetyl, Boc: tert-butoxycarbonyl, Z: benzyloxycarbonyl, TMS: trimethylsilyl, TBS: tert-butyldimethylsilyl, TBDPS: tert-butyldiphenylsilyl, Syn: Preparation method (in which the number in the column of Syn indicates that the compound is prepared by the same method as for the compound having the Preparation Example compound number or Example compound number, using the corresponding starting material. For example, the compound of Ex2 in the column of Syn is prepared by the same method as for the compound of Example 2; the compound of PEx2 in the column of Syn is prepared by the same method as for the compound of Preparation Example 2; the compounds of PEx1, PEx 16 in the column of Syn are prepared by the same method as for the compound of Preparation Example 1, followed by the same method as for the compound of Preparation Example 16), and (rac) denotes that the compound is a racemic compound.

Furthermore, in the case where the compounds represented by two structural formulae are described in combination for one Example compound or Preparation Example compound, the description of the structural formulae with "and" indicates that the compounds are obtained as a mixture of the compounds represented by such structural formulae, and a description of the structural formulae with "or" indicates that any one of the compounds represented by such structural formulae is obtained. Further, Examples 107a and 107b described below indicate a structure of any one of the respective two structural formulae. Similarly, Examples 108a and 108b described below indicate a structure of any one of the respective two structural formulae. Further, a compound having double bonds crossing in the structural formula represents a mixture of the double bonds in the E and Z configurations. Further, HCl in the structural formula indicates that the compound is hydrochloride, TFA in the structural formula indicates that the compound is trifluoroacetate, $PhSO_3H$ in the structural formula indicates that the compound is benzenesulfonate, and HBr in the structural formula indicates that the compound is hydrobromide.

In addition, in the context of the present specification, regarding to compounds with chiral centers, when a substituent bonded to a chiral center has no notation regarding to its configuration, then it means that the configuration of the substituent is not mentioned, but in the structural formulae in Compound Tables described below, when the substituent bonded to a chiral center is illustrated in the planar structure and has no notation regarding to its configuration of the substituent, then it means that the compound is a racemic compound.

The preparative separation and analysis of optical isomers may be carried out in some cases under the following conditions, using an supercritical fluid chromatography device manufactured by Waters. Rt in Tables below represents a retention time of a compound.

(Preparative Separation Condition A) Column: CHIRALPAK IA from Daicel Chemical Industries, Ltd., 5 µm, 10 mm×250 mm; Mobile Phase: carbon dioxide 65%/methanol 35%; Flow Rate: 10 ml/min; Pressure: 100 bar; Detection Wavelength: 220-300 nm; Temperature: 40° C.; Inject Volume; 50 µl; Sample Concentration:10 mg/ml (methanol:acetonitrile=3:2)

(Analysis Condition A, hereinafter referred to as AC-A) Column: CHIRALPAK IA from Daicel Chemical Industries, Ltd., 5 µm, 4.6 mm×250 mm; Mobile Phase: carbon dioxide 65%/methanol 35%; Flow Rate: 3 ml/min; Pressure: 100 bar; Detection Wavelength: 220-300 nm; Temperature: 40° C.

(Preparative Separation Condition B) Column: CHIRALCEL OD-H from Daicel Chemical Industries, Ltd., 5 µm, 10 mm×250 mm; Mobile Phase: carbon dioxide 75%/methanol 25%; Flow Rate: 15 ml/min; Pressure: 100 bar; Detection Wavelength: 220-300 nm; Temperature: 40° C.; Inject Volume; 170 µl; Sample Concentration:10 mg/ml (methanol: acetonitrile=3:2)

(Analysis Condition B, hereinafter referred to as AC-B) Column: CHIRALCEL OD-H from Daicel Chemical Industries, Ltd., 5 µm, 4.6 mm×250 mm; Mobile Phase: carbon dioxide 70%/methanol 30%; Flow Rate: 3 ml/min; Pressure: 100 bar; Detection Wavelength: 220-300 nm; Temperature: 40° C.

The Specific optical rotation $[\alpha]_D$ was measured using SEPA-300 manufactured by Horiba, Ltd. under the conditions of a solvent: methanol and an optical path: 50 mm. In Tables below, the unit of the concentration c is g/100 ml.

Furthermore, the powder X-ray diffraction was measured using RINT-TTRII under the conditions of a tube: Cu, a tube current: 300 mA, a tube voltage: 50 kV, a sampling width: 0.020°, a scan speed: 4°/min, a wavelength: 1.54056 Angstrom, a measurement diffraction angle range (2θ): 2.5 to 40°.

Further, with powder X-ray diffraction spectrum, due to the properties of the data, the crystal lattice spacing and the overall pattern are important for the certification of the crystal identity, and the diffraction angle and the diffraction strength may vary slightly depending on the direction of the crystal growth, the particle size, and the measurement condition, and thus, should not be interpreted strictly.

Furthermore, since the compounds of Preparation Examples 61 to 78, 81 to 199, 201 to 213, 215 to 262, 268 to 287, 290 and 308 to 310 were prepared in the same manner as in the methods described in Preparation Examples 1 to 60, 79, 80, 200, 214, 263 to 267, 288 and 289, which will be described later, and Examples 1, 3, and 6 to 8, which will be described later, they are only described in Tables, which will be described later.

Preparation Example 1

A suspension of 500 mg of ethyl 8-hydroxy-2-methylimidazo[1,2-a]pyridine-3-carboxylate, 0.35 ml of 2,3-difluorobenzylbromide, and 650 mg of potassium carbonate in 8.6 ml of N,N-dimethylformamide (DMF) was stirred at 60° C. for 1 hour. The reaction mixture was left to be cooled to room temperature and water was then added thereto. The resulting solid was collected by filtration and washed with water. The solid was washed with diisopropyl ether to obtain 650 mg of ethyl 8-[(2,3-difluorobenzyl)oxy]-2-methylimidazo[1,2-a]pyridine-3-carboxylate.

Preparation Example 2

To a solution of 5.8 g of 3-(cyclohexylmethoxy)pyridin-2-amine in 100 ml of toluene were added 4.3 ml of ethyl 2-chloro-3-oxobutanoate and 4.3 ml of triethylamine, followed by stirring overnight under heating to reflux. To the reaction mixture were added 1 ml of ethyl 2-chloro-3-oxobutanoate and 1 ml of triethylamine, followed by stirring for 6.5 hours under heating to reflux. To the reaction mixture was added water, followed by extraction with ethyl acetate. The organic layer was dried over anhydrous sodium sulfate and the solvent was then evaporated under reduced pressure. The obtained residue was purified by silica gel column chromatography. To the purified product thus obtained were added ethyl acetate and hexane, followed by heating and stirring, and then stirring under ice-cooling. The resulting solid was collected by filtration to obtain 4.0 g of ethyl 8-(cyclohexylmethoxy)-2-methylimidazo[1,2-a]pyridine-3-carboxylate.

Preparation Example 3

A mixture of 2 g of ethyl 8-hydroxy-2-methylimidazo[1,2-a]pyridine-3-carboxylate, 2 g of (3-fluoropyridin-2-yl)methanol, 4 g of (tributylphosphoranyliden)acetonitrile, and 40 ml of toluene was stirred at 110° C. for 2 hours. The reaction mixture was concentrated under reduced pressure, water was added thereto, and the precipitated solid was collected by filtration. The obtained residue was purified by silica gel column chromatography to obtain 2.15 g of ethyl 8-[(3-fluoropyridin-2-yl)methoxy]-2-methylimidazo[1,2-a]pyridine-3-carboxylate.

Preparation Example 4

To a solution of 2.54 g of ethyl N-(diphenylmethylene)glycinate in 15 ml of toluene were added 1.52 g of 4-bromo-1-methyl-1H-pyrazole, 522 mg of bis(tri-tert-butylphosphine)palladium(0), and 6 g of tripotassium phosphate, followed by stirring at 100° C. for 12 hours. The reaction mixture was left to be cooled to room temperature and then filtered over Celite, and the filtrate was concentrated under reduced pressure. To the obtained residue was added water, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 328 mg of ethyl [(diphenylmethylene)amino](1-methyl-1H-pyrazol-4-yl)acetate.

Preparation Example 5

A mixed liquid of 1.50 g of tert-butyl(2-bromobenzyl)carbamate, 3.90 g of tripotassium phosphate, 348 mg of dicyclohexyl(2',6'-dimethoxybiphenyl-2-yl)phosphine, 195 mg of tris(dibenzylideneacetone)dipalladium(0), 905 mg of (1Z)-prop-1-en-1-yl boronic acid, 30 ml of 1,4-dioxane, and 7.5 ml of water was stirred at 90° C. for 15 hours. The reaction mixture was left to be cooled to room temperature and then filtrated over Celite. The filtrate was concentrated under reduced pressure, and then to the reaction mixture was added water, followed by extraction with ethyl acetate. The organic layer was washed with water and a saturated aqueous sodium chloride solution, and then dried over anhydrous magnesium sulfate and the solvent was then evaporated under reduced pressure. The obtained residue was purified by silica gel chromatography to obtain 1.36 g of tert-butyl {2-[(1Z)-prop-1-en-1-yl]benzyl}carbamate.

Preparation Example 6

A mixture of 2.0 g of methyl 4-bromobenzoate, 1.3 ml of nitroethane, 172 mg of tris(dibenzylideneacetone)dipalladium(0), 232 mg of 2-(di-tert-butylphosphino)-2'-methylbiphenyl, 3.33 g of cesium carbonate, and 44 ml of 1,2-dimethoxyethane (DME) was stirred at 60° C. for 18 hours. The reaction mixture was left to be cooled to room temperature, followed by adding a saturated aqueous ammonium chloride solution and extracting with ethyl acetate. The organic layer was washed with a saturated aqueous sodium chloride solution and then dried over anhydrous magnesium sulfate, and the solvent was then evaporated under reduced pressure. The obtained residue was purified by silica gel column chromatography to obtain 1.44 g of methyl 4-(1-nitroethyl)benzoate.

Preparation Example 7

To a solution of 228 mg of ethyl [(diphenylmethylene)amino](1-methyl-1H-pyrazol-4-yl)acetate in 2.8 ml of 1,4-dioxane was added 1.9 ml of 1 M hydrochloric acid, followed by stirring at room temperature for 2.5 hours. The reaction mixture was concentrated under reduced pressure, the obtained residue was washed with diethyl ether, and to the aqueous layer was added a saturated aqueous sodium hydrogen carbonate solution, followed by extraction with chloroform. The organic layer was dried over anhydrous magnesium sulfate and the solvent was then evaporated under reduced pressure to obtain 91 mg of ethyl amino(1-methyl-1H-pyrazol-4-yl)acetate.

Preparation Example 8

To a solution of 184 mg of (R)—N-[(1S)-2-{[tert-butyl(dimethyl)silyl]oxy}-1-(5-methyl-1,3-thiazol-2-yl)ethyl]-2-methylpropane-2-sulfinamide in 2 ml of methanol was added 2 ml of a 4 M hydrogen chloride/1,4-dioxane solution, followed by stirring at room temperature for 2 hours. The reaction mixture was concentrated under reduced pressure and 1 M hydrochloric acid was added thereto, followed by washing with ethyl acetate. The aqueous layer was concentrated under reduced pressure to obtain 112 mg of (2S)-2-amino-2-(5-methyl-1,3-thiazol-2-yl)ethanol hydrochloride.

Preparation Example 9

To a solution of 400 mg of tert-butyl {(1R)-2-(benzyloxy)-1-[1-(2-cyanoethyl)-1H-tetrazol-5-yl]ethyl}carbamate in 10 ml of dichloromethane was added 0.9 ml of 1,8-diazabicyclo[5.4.0]undeca-7-ene, followed by stirring at room temperature for 2 hours. The reaction mixture was added to a mixture of ice and 1 M hydrochloric acid, followed by extraction with dichloromethane. The organic layer was dried over anhydrous sodium sulfate and the solvent was then evaporated under reduced pressure to obtain 343 mg of tert-butyl [(1R)-2-(benzyloxy)-1-(2H-tetrazol-5-yl)ethyl]carbamate.

Preparation Example 10

A mixture of 166 mg of tert-butyl [(1R)-2-(benzyloxy)-1-(2-methyl-2H-tetrazol-5-yl)ethyl]carbamate, 40 mg of 10% palladium-carbon (hydrous), and 8 ml of ethanol was stirred at room temperature for 18 hours under a hydrogen atmosphere of 4 atm. The reaction mixture was filtered over Celite and the filtrate was concentrated under reduced pressure to obtain 106 mg of tert-butyl [(1R)-2-hydroxy-1-(2-methyl-2H-tetrazol-5-yl)ethyl]carbamate.

Preparation Example 11

A solution of 106 mg of tert-butyl [(1R)-2-hydroxy-1-(2-methyl-2H-tetrazol-5-yl)ethyl]carbamate in 3 ml of methanol was added to 1.5 ml of a 4 M hydrogen chloride/1,4-dioxane solution, followed by stirring at room temperature for 2 hours. The reaction mixture was concentrated under reduced pressure to obtain 78 mg of (2R)-2-amino-2-(2-methyl-2H-tetrazol-5-yl)ethanol hydrochloride.

Preparation Example 12

To a mixture of 2.19 g of N-[2-(2,2-dimethyl-1,3-dioxolan-4-yl)benzyl]-2,2,2-trifluoroacetamide and 22 ml of methanol was added 5.0 ml of a 2 M aqueous sodium hydroxide solution, followed by stirring at 50° C. for 24 hours. The reaction mixture was left to be cooled to room temperature and then concentrated under reduced pressure, and water was added thereto, followed by extraction with chloroform. The organic layer was dried over anhydrous magnesium sulfate and the solvent was then evaporated under reduced pressure to obtain 1.52 g of 1-[2-(2,2-dimethyl-1,3-dioxolan-4-yl)phenyl]methanamine.

Preparation Example 13

To a solution of 254 mg of (S)—N-[(2S)-1-{[tert-butyl(dimethyl)silyl]oxy}-2-(5-methyl-1,3-thiazol-2-yl)propan-2-yl]-2-methylpropane-2-sulfinamide in 6.9 ml of tetrahydrofuran (THF) was added 1.1 ml of a 4 M hydrogen chloride/1,4-dioxane solution, followed by stirring at room temperature for 4 hours. To the reaction mixture was added 0.62 ml of triethylamine, and water was then added thereto, followed by extraction with chloroform. The organic layer was dried over anhydrous magnesium sulfate and the solvent was then evaporated under reduced pressure. To the obtained residue was added ethyl acetate and the insoluble materials were separated by filtration. The filtrate was concentrated under reduced pressure to obtain 185 mg of (2S)-1-{[tert-butyl (dimethyl)silyl]oxy}-2-(5-methyl-1,3-thiazol-2-yl)propan-2-amine.

Preparation Example 14

To a solution of 84 mg of tert-butyl 2,2,4-trimethyl-4-(5-methyl-1,3,4-oxadiazol-2-yl)-1,3-oxazolidine-3-carboxylate in 1.5 ml of dichloromethane was added 500 µl of trifluoroacetic acid, followed by stirring at room temperature for 2 hours. The reaction mixture was concentrated under reduced pressure, methanol was added thereto, and the solvent was evaporated again to obtain 76 mg of 2-amino-2-(5-methyl-1,3,4-oxadiazol-2-yl)propan-1-ol trifluoroacetate.

Preparation Example 15

To a mixture of 167 mg of 8-[(2,6-difluorobenzyl)oxy]-2-methylimidazo[1,2-a]pyridine-3-carboxylic acid and 1.5 ml of dichloromethane was added 90 µl of 1-chloro-N,N,2-trimethylprop-1-en-1-amine under ice-cooling, followed by stirring at room temperature for 30 minutes. A solution of 93 mg of ethyl 2-amino-2-(pyrimidin-5-yl)propanoate in 1.5 ml of dichloromethane and 0.15 ml of triethylamine were added thereto under ice-cooling, followed by stirring at room temperature for 2 hours. To the reaction mixture was added water, followed by extraction with chloroform. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 56 mg of ethyl 2-[({8-[(2,6-difluorobenzyl)oxy]-2-methylimidazo[1,2-a]pyridin-3-yl}carbonyl)amino]-2-(pyrimidin-5-yl)propanoate.

Preparation Example 16

To a mixture of 200 mg of 8-[(2,6-difluorobenzyl)oxy]-2-methylimidazo[1,2-a]pyridine-3-carboxylic acid, 6 ml of dichloromethane, and one droplet of DMF was added 110 µl of oxalyl chloride under ice-cooling, followed by stirring at room temperature for 30 minutes. The reaction mixture was concentrated under reduced pressure, and to the obtained residue were added 10 ml of THF, 300 µl of diisopropylethylamine, and a solution of 170 mg of 1-[2-(2,2-dimethyl-1,3-dioxolan-4-yl)phenyl]methanamine in 5 ml of THF under ice-cooling, followed by stirring at room temperature for 24 hours. To the reaction mixture was added water, followed by extraction with ethyl acetate. The organic layer was washed with a 10% aqueous citric acid solution, a saturated aqueous sodium hydrogen carbonate solution, water, and a saturated aqueous sodium chloride solution, and dried over anhydrous magnesium sulfate, and the solvent was then evaporated under reduced pressure. The obtained residue was purified by silica gel column chromatography to obtain 278 mg of 8-[(2,6-difluorobenzyl)oxy]-N-[2-(2,2-dimethyl-1,3-dioxolan-4-yl)benzyl]-2-methylimidazo[1,2-a]pyridine-3-carboxamide.

Preparation Example 17

To a solution of 330 mg of 5-methyl-1,3-thiazole in 3.4 ml of THF were added 1.2 ml of a 2.69 M n-butyllithium/hexane solution at −78° C., followed by stirring for 45 minutes. To the reaction mixture was added dropwise a solution of 509 mg of (R)—N-[(1E)-2-{[tert-butyl (dimethyl)silyl]oxy}ethylidene]propane-2-sulfinamide in 3.4 ml of toluene, followed by warming to 0° C. and stirring for 2 hours. To the reaction mixture was added a saturated aqueous ammonium chloride solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 584 mg of a low-polarity compound, (R)—N-[(1S)-2-{[tert-butyl (dimethyl)silyl]oxy}-1-(5-methyl-1,3-thiazol-2-yl)ethyl]-2-methylpropane-2-sulfinamide, and 130 mg of a high-polarity compound, (R)—N-[(1R)-2-{[tert-butyl (dimethyl)silyl]oxy}-1-(5-methyl-1,3-thiazol-2-yl)ethyl]-2-methylpropane-2-sulfinamide, respectively.

The absolute configurations of the Preparation Example compounds and the compound synthesized with reference to the Preparation Examples were presumed from the information of the chemical shift values of 1H-NMR, the Rf values of thin layer chromatography, and the yields of main products/side products of the reaction, according to a literature [J. Org. Chem., (2001) 66, 8772-8778].

Preparation Example 18

To a solution of 398 mg of (S)—N-[(2E)-1-{[tert-butyl (dimethyl)silyl]oxy}propan-2-ylidene]-2-methylpropane-2-sulfinamide in 5.4 ml of toluene were added 0.77 ml of a 2.0 M trimethylaluminum/toluene solution at −78° C., followed by stirring for 30 minutes. To this reaction mixture was added 2 ml of a 1 M phenyllithium/cyclohexane-diethyl ether solution at −78° C., followed by stirring for 1 hour, then warming to 0° C., and stirring for 1 hour. To the reaction mixture was added a saturated aqueous ammonium chloride solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 191 mg of a high-polarity compound, (S)—N-[(2R)-1-{[tert-butyl (dimethyl)silyl]oxy}-2-phenylpropan-2-yl]-2-methylpropane-2-sulfinamide, and 88 mg of a low-polarity compound, (S)—N-[(2S)-1-{[tert-butyl (dimethyl)silyl]oxy}-2-phenylpropan-2-yl]-2-methylpropane-2-sulfinamide. The absolute configuration was determined by comparison of 1H-NMR with the optical isomers described in a literature [J. Org. Chem., (2001) 66, 8772-8778].

Furthermore, the absolute configurations of the compounds synthesized with reference to the Preparation Examples were presumed from the information of the chemical shift values of 1H-NMR, the Rf values of thin layer chromatography, and the yields of main products/side products of the reaction, with reference to the literature above.

Preparation Example 19

To a solution of 403 mg of (S)—N-[(2R)-2-(3-bromophenyl)-1-{[tert-butyl(dimethyl)silyl]oxy}propan-2-yl]-2-methylpropane-2-sulfinamide in 4 ml of THF was added 1.4 ml of a 1.63 M n-butyllithium/hexane solution at −78° C., followed by stirring for 30 minutes, and then 283 µl of methyl chloroformate was added dropwise thereto, followed by stirring for 1 hour. To the reaction mixture was added a saturated aqueous ammonium chloride solution, followed by extraction with ethyl acetate. The organic layer was washed with a saturated aqueous sodium chloride solution and dried over anhydrous magnesium sulfate, and the solvent was then evaporated under reduced pressure. The residue was purified by silica gel column chromatography to obtain 280 mg of methyl 3-[(6R,8S)-2,2,3,3,6,9,9-heptamethyl-8-oxo-4-oxa-8$\lambda^4$-thia-7-aza-3-siladecan-6-yl]benzoate.

Preparation Example 20

To a solution of 1.5 g of 2-methyl-1,3-thiazole in 20 ml of THF was added 5.5 ml of a 2.76 M n-butyllithium/hexane solution at −78° C., followed by stirring for 30 minutes. To the reaction mixture was added dropwise a solution of 2 ml of ethyl 2-oxopropanoate in 10 ml of THF, followed by stirring at −78° C. for 1 hour. To the reaction mixture was added a saturated aqueous ammonium chloride solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 1.05 g of ethyl 2-hydroxy-2-(2-methyl-1,3-thiazol-5-yl)propanoate.

Preparation Example 21

To a solution of 2.01 g of 2-bromo-4-methylpyridine in 10 ml of THF were added 4.3 ml of a 2.69 M n-butyllithium/ hexane solution at −78° C., followed by stirring for 30 minutes. To the reaction mixture was added dropwise a solution of 1 g of 2,2-dimethyl-1,3-dioxan-5-one in 5 ml of THF, followed by stirring at −78° C. for 2 hours. To the reaction mixture was added a saturated aqueous ammonium chloride solution, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 700 mg of 2,2-dimethyl-5-(4-methylpyridin-2-yl)-1,3-dioxan-5-ol.

Preparation Example 22

To a solution of 226 mg of 1-phenylcyclopent-3-en-1-amine in 10 ml of dichloromethane were added 0.4 ml of triethylamine and 620 mg of di-tert-butyl dicarbonate, followed by stirring at room temperature for 6 hours. The reaction mixture was concentrated under reduced pressure and the obtained residue was purified by silica gel column chromatography to obtain 52 mg of tert-butyl (1-phenylcyclopent-3-en-1-yl)carbamate.

Preparation Example 23

To a solution of 2.12 g of 1,3-thiazol-5-ylmethanol in 48 ml of dichloromethane were added 5.2 ml of tert-butyl (chloro)diphenylsilane and 2.5 g of imidazole at 0° C., followed by stirring at room temperature for 15 hours. To the reaction mixture was added water, and the organic layer was dried over anhydrous magnesium sulfate. The solvent was then evaporated under reduced pressure. The obtained residue was purified by silica gel column chromatography to obtain 6.47 g of 5-({[tert-butyl (diphenyl)silyl]oxy}methyl)-1,3-thiazole.

Preparation Example 24

To a solution of 5.0 g of ethyl 2,2-dimethyl-5-nitro-1,3-dioxane-5-carboxylate in 50 ml of acetic acid was added 7 g of zinc powder in four divided portions at room temperature, followed by stirring at 45° C. for 4 hours. The insoluble materials of the reaction mixture were separated by filtration and washed with chloroform. The filtrate was concentrated under reduced pressure and neutralized by the addition of a saturated aqueous sodium hydrogen carbonate solution. To a mixture formed by adding 100 ml of chloroform thereto were added 2.7 g of sodium hydrogen carbonate and 3.7 ml of benzyl chloroformate at 0° C., followed by stirring at room temperature for 2 hours. The obtained organic layer was dried over anhydrous sodium sulfate and the solvent was then evaporated under reduced pressure. The obtained residue was purified by silica gel column chromatography to obtain 6.6 g of ethyl 5-{[(benzyloxy)carbonyl]amino}-2,2-dimethyl-1,3-dioxane-5-carboxylate.

Preparation Example 25

To a mixture of 1.18 g of sodium 2,2-dimethyl-5-(5-methylpyridin-2-yl)-1,3-dioxane-5-carboxylate, 12 ml of 1,4-dioxane, and 2.4 ml of water were added 730 mg of sodium hydrogen carbonate and 0.85 ml of isobutyl chloroformate under ice-cooling, followed by stirring for 1 hour. 12 ml of 1,4-dioxane and 2.4 ml of water were added thereto, followed by warming to room temperature and stirring for 1 hour. The reaction mixture was ice-cooled again, and 730 mg of sodium hydrogen carbonate and 0.85 ml of isobutyl chloroformate were added thereto, followed by stirring at room temperature for 30 minutes. To the reaction mixture was added a solution of 2.82 g of sodium azide in 9.6 ml of water under ice-cooling, followed by stirring at the same temperature for 10 minutes and at room temperature for 30 minutes. To the reaction mixture was added water under ice-cooling, followed by extraction with diethyl ether. The organic layer was washed with a saturated aqueous sodium chloride solution and dried over anhydrous magnesium sulfate, and the solvent was then evaporated under reduced pressure. To the obtained residue was added 12 ml of toluene, followed by stirring at 100° C. for 20 minutes. The reaction mixture was left to be cooled to room temperature and 2.3 ml of benzyl alcohol was added thereto, followed by further stirring at 100° C. for 16 hours. The reaction mixture was left to be cooled to room temperature, and then concentrated under reduced pressure. The obtained residue was purified by silica gel column chromatography to obtain 1.19 g of benzyl [2,2-dimethyl-5-(5-methylpyridin-2-yl)-1,3-dioxan-5-yl]carbamate.

Preparation Example 26

To a mixture of 398 mg of sodium 5-(5-chloropyridin-2-yl)-2,2-dimethyl-1,3-dioxane-5-carboxylate, 7.7 ml of 1,4-dioxane, and 1.6 ml of water were added 462 mg of sodium hydrogen carbonate and 0.54 ml of isobutyl chloroformate under ice-cooling, followed by stirring for 2 hours. To the reaction mixture was added a solution of 893 mg of sodium azide in 3.4 ml of water under ice-cooling, followed by stirring at room temperature for 1 hour. To the reaction mixture was added water under ice-cooling, followed by extraction with diethyl ether. The organic layer was washed with a saturated aqueous sodium chloride solution and dried over anhydrous magnesium sulfate, and the solvent was then evaporated under reduced pressure. To the obtained residue was added 3.4 ml of toluene, followed by stirring at 100° C. for 1 hour. The reaction mixture was left to be cooled to room temperature and 1 ml of 2-(trimethylsilyl)ethanol was added thereto, followed by stirring again at 100° C. for 20 hours. The reaction mixture was left to be cooled to room temperature and then concentrated under reduced pressure. The obtained residue was purified by silica gel column chromatography to obtain 156 mg of 2-(trimethylsilyl)ethyl [5-(5-chloropyridin-2-yl)-2,2-dimethyl-1,3-dioxan-5-yl]carbamate.

Preparation Example 27

To a mixture of 4 mg of lithium aluminum hydride and 0.2 ml of THF was added dropwise a solution of 20 mg of ethyl 2-amino-2-(pyrimidin-2-yl)propanoate in 0.2 ml of THF at 0° C. solution, followed by stirring at the same temperature for 7 hours. 2.5 mg of lithium aluminum hydride was added thereto, followed by stirring at 0° C. for 1 hour. 32 µl of water, 32 µl of a 15% aqueous sodium hydroxide solution, and 96 µl of water were sequentially added thereto at 0° C. The insoluble materials of the reaction mixture were filtered over Celite and washed with ethyl acetate, and the filtrate was then concentrated under reduced pressure. The obtained residue was purified by silica gel column chromatography to obtain 7 mg of 2-amino-2-(pyrimidin-2-yl)propan-1-ol.

Preparation Example 28

To a solution of 490 mg of 5-(4-fluorophenyl)-2,2-dimethyl-5-nitro-1,3-dioxane in 7.4 ml of acetic acid was added 628 mg of zinc powder, followed by stirring at room temperature for 2 hours. The insoluble materials were separated by filtration and washed with chloroform, and the filtrate was then concentrated under reduced pressure. To the obtained residue was added a 1 M aqueous sodium hydroxide solution, followed by extraction with chloroform. The organic layer was dried over anhydrous magnesium sulfate and the solvent was then evaporated under reduced pressure. The obtained residue was purified by silica gel column chromatography to obtain 325 mg of 5-(4-fluorophenyl)-2,2-dimethyl-1,3-dioxan-5-amine.

Preparation Example 29

A mixture of 250 mg of ethyl 2-azide-2-(1-methyl-1H-pyrazol-4-yl)propanoate, 50 mg of a palladium-carbon-ethylene diamine complex, and 2.5 ml of ethanol was stirred for 16 hours under a hydrogen atmosphere of 1 atm. The reaction mixture was filtered over Celite and the liquid was concentrated under reduced pressure. To the obtained residue were added 2.5 ml of ethanol and 50 mg of a palladium-carbon-ethylene diamine complex 50 mg, followed by stirring for 4 hours under a hydrogen atmosphere of 1 atm. The reaction mixture was filtered over Celite and the filtrate was concentrated under reduced pressure. The obtained residue was purified by silica gel column chromatography to obtain 95 mg of ethyl 2-amino-2-(1-methyl-1H-pyrazol-4-yl)propanoate.

Preparation Example 30

Under an argon atmosphere, to a solution of 2.18 g of methyl 3-(2,2-dimethyl-5-nitro-1,3-dioxan-5-yl)benzoate in 26 ml of ethanol and 7 ml of THF was added a suspension of Raney nickel (manufactured by Aldrich, 1.2 ml of a suspension was washed with water and ethanol) in 5 ml of ethanol, followed by stirring at room temperature for 7 hours under a hydrogen atmosphere of 4 atm. The reaction mixture was filtered over Celite and the liquid was concentrated under reduced pressure. To a solution of the obtained residue in 26 ml of ethanol and 7 ml of THF was added a suspension of Raney nickel (manufactured by Aldrich, 1.2 ml of a suspension was washed with water and ethanol) in 5 ml of ethanol under an argon atmosphere, followed by stirring at room temperature for 16 hours under a hydrogen atmosphere of 4 atm. The reaction mixture was filtered over Celite and the filtrate was concentrated under reduced pressure to obtain 2.09 g of methyl 3-(5-amino-2,2-dimethyl-1,3-dioxan-5-yl)benzoate.

Preparation Example 31

To a solution of 456 mg of ethyl [(diphenylmethylene)amino](pyrimidin-5-yl)acetate in 4.5 ml of DMF was added 69 mg of sodium hydride (55% mineral oil included) under ice-cooling, followed by stirring for 30 minutes. To the reaction mixture was added 0.1 ml of methyl iodide, followed by stirring at room temperature for 1.5 hours. To the reaction mixture was added water, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 224 mg of ethyl 2-[(diphenylmethylene)amino]-2-(pyrimidin-5-yl)propanoate.

Preparation Example 32

To a mixture of 1.44 g of methyl 4-(1-nitroethyl)benzoate and 29 ml of DMF were added 612 mg of paraformaldehyde and 150 mg of sodium methoxide, followed by stirring at room temperature for 18 hours. To the reaction mixture was added a saturated aqueous ammonium chloride solution, followed by extraction with ethyl acetate. The organic layer was dried over anhydrous magnesium sulfate and the solvent was then evaporated. The obtained residue was purified by silica gel column chromatography to obtain 730 mg of methyl 4-(1-hydroxy-2-nitropropan-2-yl)benzoate.

Preparation Example 33

To a mixture of 575 mg of methyl (5-methylpyridin-2-yl)acetate and 11.5 ml of DMF were added 314 mg of paraformaldehyde and 38 mg of sodium methoxide under ice-cooling, followed by stirring at room temperature for 24 hours. The reaction mixture was ice-cooled and 50 µl of acetic acid was added thereto, followed by concentrating under reduced pressure. The obtained residue was purified by silica gel column chromatography to obtain 462 mg of methyl 3-hydroxy-2-(hydroxymethyl)-2-(5-methylpyridin-2-yl)propanoate.

Preparation Example 34

Under an argon atmosphere, to a solution of 500 mg of ethyl (1-methyl-1H-pyrazol-4-yl)(oxo)acetate that had been cooled in a dry ice-acetone bath in 7.5 ml of THF was added 1.56 ml of a 3.0 M methyl magnesium bromide/diethyl ether solution, followed by stirring for 1 hour. To the reaction mixture was added a saturated aqueous ammonium chloride solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 302 mg of ethyl 2-hydroxy-2-(1-methyl-1H-pyrazol-4-yl)propanoate.

Preparation Example 35

To a solution of 1.73 g of di-tert-butyl imidodicarbonate in DMF 16 ml was added 894 mg of potassium tert-butoxide under ice-cooling, followed by stirring at room temperature for 1 hour. To the reaction mixture was added a solution of 1.37 g of 3-bromo-4-(chloromethyl)pyridine in 3 ml of DMF under ice-cooling, followed by stirring at room temperature for 2 hours. To the reaction mixture was added water, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 2.32 g of di-tert-butyl [(3-bromopyridin-4-yl)methyl]imidodicarbonate.

Preparation Example 36

To a solution of 724 mg of phenoxydiphenylphosphine in 3.5 ml of toluene was added 0.39 ml of trimethylsilylmethyl azide, followed by stirring at 80° C. for 20 minutes. Then, a solution of 172 mg of ethyl 2-hydroxy-2-(1-methyl-1H-pyrazol-4-yl)propanoate in 3.5 ml of toluene solution and 0.35 ml of azide(trimethyl)silane were added thereto, followed by stirring at room temperature for 24 hours. The reaction mixture was concentrated under reduced pressure and the obtained residue was purified by silica gel column chromatography to obtain 250 mg of ethyl 2-azide-2-(1-methyl-1H-pyrazol-4-yl)propanoate as a mixture with impurities.

Preparation Example 37

To a mixture of 4.16 g of silver nitrite and 22 ml of diethyl ether was added dropwise a solution of 4.06 g of methyl 3-(bromomethyl)benzoate in 15 ml of diethyl ether over 30 minutes under ice-cooling, followed by stirring for 3 hours. The insoluble materials were separated by filtration and the filtrate was concentrated under reduced pressure. The obtained residue was purified by silica gel column chromatography to obtain 2.58 g of methyl 3-(nitromethyl)benzoate.

Preparation Example 38

To a solution of 5 g of 6-methoxynicotinealdehyde in 100 ml of ethanol were added 10 g of potassium carbonate and 4.0 g of hydroxylamine hydrochloride, followed by stirring for 3 hours under heating to reflux. The reaction mixture was left to be cooled to room temperature, the insoluble materials were then separated by filtration, and the filtrate was concentrated. To the obtained residue was added water, followed by extraction with ethyl acetate. The organic layer was washed with a saturated aqueous sodium chloride solution and dried over anhydrous magnesium sulfate. The solvent was evaporated under reduced pressure to obtain 5.42 g of N-hydroxy-1-(6-methoxypyridin-3-yl)methanimine.

Preparation Example 39

To a mixture of 2 g of N-hydroxy-1-(6-methoxypyridin-3-yl)methanimine, 50 ml of acetonitrile, and 50 ml of an aqueous phosphate buffer solution (pH 6.9) was added a mixed liquid of 20 g of potassium peroxymonosulfate (Oxone: $2KHSO_5.KHSO_4.K_2SO_4$) in 50 ml water and 50 ml of acetone at room temperature, followed by stirring at 45° C. for 4 hours. The insoluble materials were separated by filtration and washed with diethyl ether. The organic layer was washed with a saturated aqueous sodium sulfite solution and a saturated aqueous sodium chloride solution, and dried over anhydrous magnesium sulfate, and the solvent was then evaporated under reduced pressure. The obtained residue was purified by silica gel column chromatography to obtain 251 mg of 2-methoxy-5-(nitromethyl)pyridine.

Preparation Example 40

To a solution of 610 mg of tert-butyl (1-phenylcyclopent-3-en-1-yl)carbamate in 18 ml of dichloromethane were added 398 mg of sodium hydrogen carbonate and 812 mg of m-chloroperbenzoic acid (hydrous) under ice-cooling, followed by stirring at room temperature for 16 hours. To the reaction mixture was added a saturated aqueous sodium thiosulfate solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 393 mg of tert-butyl [(1R,3r,5S)-3-phenyl-6-oxabicyclo[3.1.0]hexa-3-yl]carbamate or tert-butyl [(1R,3s,5S)-3-phenyl-6-oxabicyclo[3.1.0]hex-3-yl]carbamate.

Preparation Example 41

To a solution of 130 mg of tert-butyl [(1R,3r,5S)-3-phenyl-6-oxabicyclo[3.1.0]hex-3-yl]carbamate or tert-butyl [(1R,3s,5S)-3-phenyl-6-oxabicyclo[3.1.0]hex-3-yl]carbamate in 0.65 ml of THF and 0.65 ml of water was added 32.5 mg of tetra-n-butylammonium hydrogen sulfate, followed by stirring at 70° C. for 2 days. To the reaction mixture was added water, followed by extraction with chloroform. The organic layer was washed with a saturated aqueous sodium chloride solution and dried over anhydrous magnesium sulfate, and the solvent was then evaporated under reduced pressure. The residue was purified by silica gel column chromatography to obtain 31 mg of tert-butyl rac-[(3R,4R)-3,4-dihydroxy-1-phenylcyclopentyl]carbamate.

Preparation Example 42

A mixture of 4.98 g of a mixture of 1,3-dimethyl-1H-pyrazole and 1,5-dimethyl-1H-pyrazole, and 17.3 ml of ethyl chloro(oxo)acetate was stirred at 90° C. for 18 hours. The reaction mixture was left to be cooled to room temperature and then diluted with ethyl acetate, and ice water was slowly added thereto. To this reaction mixture was added a saturated aqueous sodium hydrogen carbonate solution and the organic layer was washed with a saturated aqueous sodium chloride solution. The obtained mixture was dried over anhydrous magnesium sulfate and the solvent was then evaporated under reduced pressure to obtain 3.74 g of a mixture of ethyl (1,3-dimethyl-1H-pyrazol-4-yl)(oxo)acetate and ethyl (1,5-dimethyl-1H-pyrazol-4-yl)(oxo)acetate.

Preparation Example 43

To a solution of 370 mg of rac-(1R,2R,5R)-5-phenyl-6-oxabicyclo[3.1.0]hexan-2-ol in 22 ml of acetonitrile were added 1.34 g of lithium perchlorate and 410 mg of sodium azide, followed by warming to 65° C. and stirring for 3 hours, and subsequently warming to 80° C. and stirring for 18 hours. The reaction mixture was left to be cooled to room temperature, and then a saturated aqueous sodium hydrogen carbonate solution was added thereto, followed by extraction with ethyl acetate. The organic layer was washed with a saturated aqueous sodium chloride solution and dried over anhydrous magnesium sulfate, and the solvent was then evaporated under reduced pressure. To the residue were added 15 ml of acetonitrile, 1.34 g of lithium perchlorate, and 410 mg of sodium azide, followed by stirring at 80° C. for 18 hours. The reaction mixture was left to be cooled to room temperature and then a saturated aqueous sodium hydrogen carbonate solution was added thereto, followed by extraction with ethyl acetate. The organic layer was washed with a saturated aqueous sodium chloride solution and dried over anhydrous magnesium sulfate, and the solvent was then evaporated under reduced pressure to obtain 460 mg of rac-(1R,2S,3S)-3-azide-3-phenylcyclopentane-1,2-diol.

Preparation Example 44

To a mixture of 1.7 g of 2,2,2-trifluoro-N-(2-vinylbenzyl)acetamide, 1.31 g of 4-methylmorpholine 4-oxide, 43 ml of THF, and 17 ml of water was added 1.85 ml of a 2.5% aqueous tetraoxoosmium solution, followed by stirring at room temperature for 16 hours. To the reaction mixture was added a 10% aqueous sodium thiosulfate solution, followed by stirring at room temperature, followed by extraction with ethyl acetate. The organic layer was washed with a saturated aqueous sodium chloride solution and washed with anhydrous magnesium sulfate, and the solvent was then evaporated under reduced pressure to obtain 1.94 g of N-[2-(1,2-dihydroxyethyl)benzyl]-2,2,2-trifluoroacetamide.

Preparation Example 45

To a mixture of 3.30 g of AD mix-α, 200 mg of methanesulfonamide, 12.5 ml of tert-butyl alcohol, and 12.5 ml of water was added a solution of 500 mg of tert-butyl {2-[(1Z)-prop-1-en-1-yl]benzyl}carbamate in 5 ml of tert-butyl alcohol, followed by stirring at room temperature for 12 hours. To the reaction mixture was added sodium thiosulfate, followed by extraction with chloroform. The organic layer was washed with a saturated aqueous sodium chloride solution and dried over anhydrous magnesium sulfate, and the solvent was then evaporated under reduced pressure. The obtained residue was purified by silica gel column chromatography to obtain 449 mg of tert-butyl {2-[(1S,2R)-1,2-dihydroxypropyl]benzyl}carbamate.

The absolute configurations of the obtained compounds and Preparation Example compounds and the compound synthesized with reference to Preparation Examples above were presumed according to a literature [Chem. Rev., (1994) volume 94, issue 8, 2483].

Preparation Example 46

To a mixture of 410 mg of tert-butyl {(2S)-3-(benzyloxy)-1-[(2-cyanoethyl)amino]-1-oxopropan-2-yl}carbamate, 400 mg of triphenylphosphine, and 10 ml of acetonitrile were added 310 µl of diisopropyl azodicarboxylate and 210 µl of trimethylsilyl azide under ice-cooling, followed by stirring at room temperature for 22 hours. The reaction mixture was concentrated under reduced pressure and the obtained residue was purified by silica gel column chromatography to obtain 280 mg of tert-butyl {(1R)-2-(benzyloxy)-1-[1-(2-cyanoethyl)-1H-tetrazol-5-yl]ethyl}carbamate.

Preparation Example 47

To a solution of 60 mg of N-(1-{[tert-butyl (diphenyl)silyl]oxy}-2-cyanopropan-2-yl)-8-[(2,6-difluorobenzyl)oxy]-2-methylimidazo[1,2-a]pyridine-3-carboxamide in 2 ml of DMF were added 70 mg of sodium azide and 60 mg of ammonium chloride, followed by stirring at 120° C. for 4 hours. The reaction mixture was left to be cooled to room temperature and water was then added thereto, followed by extraction with chloroform. The organic layer was washed with a saturated aqueous sodium chloride solution and dried over anhydrous sodium sulfate, and the solvent was then evaporated under reduced pressure. The obtained residue was purified by silica gel column chromatography. To the obtained crude product was added ethyl acetate, and the insoluble materials were collected by filtration and dried under reduced pressure to obtain 19 mg of 8-[(2,6-difluorobenzyl)oxy]-N-[1-hydroxy-2-(2H-tetrazol-5-yl)propan-2-yl]-2-methylimidazo[1,2-a]pyridine-3-carboxamide.

Preparation Example 48

Under an argon atmosphere, to a solution of 400 mg of benzyl [2,2-dimethyl-5-(prop-2-yn-1-ylcarbamoyl)-1,3-dioxan-5-yl]carbamate in 4 ml of dichloromethane was added 104 mg of gold (III) chloride, followed by stirring at room temperature for 3 days. The reaction mixture was concentrated under reduced pressure and the obtained residue was purified by silica gel column chromatography to obtain 35 mg of benzyl [2,2-dimethyl-5-(5-methyl-1,3-oxazol-2-yl)-1,3-dioxan-5-yl]carbamate.

Preparation Example 49

To a solution of 320 mg of tert-butyl 4-[(2-acetylhydrazino)carbonyl]-2,2,4-trimethyl-1,3-oxazolidine-3-carboxylate in 10 ml of dichloroethane was added 358 mg of a Burgess reagent ((methoxycarbonylsulfamoyl)triethylammonium hydroxide inner salt), followed by stirring at 80° C. for 2 hours. The reaction mixture was concentrated under reduced pressure and the obtained residue was purified by silica gel column chromatography to obtain 84 mg of tert-butyl 2,2,4-trimethyl-4-(5-methyl-1,3,4-oxadiazol-2-yl)-1,3-oxazolidine-3-carboxylate.

Preparation Example 50

To a mixture of 1.93 g of N-[2-(1,2-dihydroxyethyl)benzyl]-2,2,2-trifluoroacetamide and 20 ml of acetone were added 1.1 ml of 2-methoxyprop-1-ene and 140 mg of 4-methylbenzenesulfonic acid monohydrate under ice-cooling, followed by stirring at room temperature for 2 hours. To the reaction mixture was added an aqueous sodium hydrogen carbonate solution under ice-cooling, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 2.2 g of N-[2-(2,2-dimethyl-1,3-dioxolan-4-yl)benzyl]-2,2,2-trifluoroacetamide.

Preparation Example 51

To a solution of 35 mg of benzyl [2,2-dimethyl-5-(5-methyl-1,3-oxazol-2-yl)-1,3-dioxan-5-yl]carbamate in 2 ml of ethanol was added 10 mg of 10% palladium-carbon (hydrated), followed by stirring at room temperature for 4 hours under a hydrogen atmosphere of 1 atm. The reaction mixture was filtered over Celite and the filtrate was concentrated under reduced pressure to obtain 21.4 mg of 2,2-dimethyl-5-(5-methyl-1,3-oxazol-2-yl)-1,3-dioxan-5-amine.

Preparation Example 52

To a solution of 300 mg of N-(1-{[tert-butyl (diphenyl)silyl]oxy}-2-cyanopropan-2-yl)-8-[(2,6-difluorobenzyl)oxy]-2-methylimidazo[1,2-a]pyridine-3-carboxamide in 6 ml of toluene was added 240 mg of trimethyltin azide, followed by stirring for 4 hours under heating to reflux. The reaction mixture was left to be cooled to room temperature, and 10 ml of methanol and 10 ml of 1 M hydrochloric acid were then added thereto, followed by stirring at room temperature for 2 hours. The reaction mixture was neutralized by the addition of 1 M sodium hydroxide and extracted with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 292 mg of N-[1-{[tert-butyl (diphenyl)silyl]oxy}-2-(2H-tetrazol-5-yl)propan-2-yl]-8-[(2,6-difluorobenzyl)oxy]-2-methylimidazo[1,2-a]pyridine-3-carboxamide.

Preparation Example 53

To a solution of 420 mg of tert-butyl 4-[(2-acetylhydrazino)carbonyl]-2,2,4-trimethyl-1,3-oxazolidine-3-carboxylate in 13 ml of toluene was added 309 mg of 2,4-bis(4-methoxyphenyl)-1,3,2,4-dithiadiphosphetane-2,4-disulfide, followed by stirring at 110° C. for 5 hours. The reaction mixture was concentrated under reduced pressure. The obtained residue was purified by silica gel column chromatography to obtain 228 mg of tert-butyl 2,2,4-trimethyl-4-(5-methyl-1,3,4-thiadiazol-2-yl)-1,3-oxazolidine-3-carboxylate.

Preparation Example 54

To a solution of 430 mg of 3-(tert-butoxycarbonyl)-2,2,4-trimethyl-1,3-oxazolidine-4-carboxylic acid in 4 ml of DMF was added 296 mg of 1,1'-carbonyldiimidazole, followed by stirring at room temperature for 2 hours. To the reaction mixture was added 146 mg of N-hydroxyacetamidine, followed by stirring at room temperature for 1 hour, at 110° C. for 2 hours, and then at 130° C. overnight. The reaction mixture was left to be cooled to room temperature and the solvent was evaporated under reduced pressure. The obtained residue was purified by silica gel column chromatography to obtain 390 mg of tert-butyl 2,2,4-trimethyl-4-(3-methyl-1,2,4-oxadiazol-5-yl)-1,3-oxazolidine-3-carboxylate.

Preparation Example 55

A mixture of 137 mg of copper (II) acetate, 121 mg of 2,2'-bipyridine, and 10 ml of dichloroethane was heated to an inner temperature of 70° C., and to this mixture was added a mixture of 501 mg of N-[1-{[tert-butyl (diphenyl)silyl]oxy}-2-(2H-tetrazol-5-yl)propan-2-yl]-8-[(2,6-difluorobenzyl)oxy]-2-methylimidazo[1,2-a]pyridine-3-carboxamide, 135 mg of cyclopropylboronic acid, 182 mg of sodium carbonate, and 10 ml of dichloroethane, followed by stirring at 70° C. for 4 hours. The reaction mixture was left to be cooled to room temperature, and a saturated aqueous ammonium chloride solution and water were then added thereto. The aqueous layer was extracted with chloroform, and the organic layer was then combined and concentrated under reduced pressure. The obtained residue was purified by silica gel column chromatography to obtain 280 mg of N-[1-{[tert-butyl (diphenyl)silyl]oxy}-2-(2-cyclopropyl-2H-tetrazol-5-yl)propan-2-yl]-8-[(2,6-difluorobenzyl)oxy]-2-methylimidazo[1,2-a]pyridine-3-carboxamide.

Preparation Example 56

A solution of 244 mg of tert-butyl 4-carbamothioyl-2,2,4-trimethyl-1,3-oxazolidine-3-carboxylate and 0.1 ml of 1-bromoacetone in 10 ml of ethanol was stirred at 75° C. for 2 hours. The reaction mixture was concentrated under reduced pressure and the obtained residue was purified by silica gel column chromatography to obtain 102 mg of tert-butyl 2,2,4-trimethyl-4-(4-methyl-1,3-thiazol-2-yl)-1,3-oxazolidine-3-carboxylate.

Preparation Example 57

To a solution of 146 mg of tert-butyl 4-(N'-hydroxycarbamimidoyl)-2,2,4-trimethyl-1,3-oxazolidine-3-carboxylate in 4 ml of dichloromethane was added 55 µl of acetic anhydride, followed by stirring at room temperature for 1 hour. The reaction mixture was concentrated under reduced pressure, and to the obtained residue were added 4 ml of DMF, followed by stirring at 110° C. for 15 hours. The reaction mixture was concentrated under reduced pressure and the obtained residue was purified by silica gel column chromatography to obtain 113 mg of tert-butyl 2,2,4-trimethyl-4-(5-methyl-1,2,4-oxadiazol-3-yl)-1,3-oxazolidine-3-carboxylate.

Preparation Example 58

To a mixture of 2 g of (S)-1-(2-bromophenyl)ethylamine and 20 ml of dichloromethane were added 2.1 ml of triethylamine and 1.7 ml of trifluoroacetic anhydride under ice-cooling, followed by stirring at room temperature for 4 hours. To the reaction mixture was added a 10% aqueous citric acid solution under ice-cooling, and the organic layer was washed with a saturated aqueous sodium hydrogen carbonate solution and dried over anhydrous magnesium sulfate. The solvent was then evaporated under reduced pressure. The obtained residue was purified by silica gel column chromatography to obtain 2.84 g of N-[(1S)-1-(2-bromophenyl)ethyl]-2,2,2-trifluoroacetamide.

Preparation Example 59

To a mixture of 1.17 g of methyl 2,2-dimethyl-5-(5-methylpyridin-2-yl)-1,3-dioxane-5-carboxylate, 14 ml of THF, and 14 ml of methanol was added 4.7 ml of a 1 M aqueous sodium hydroxide solution, followed by stirring at 50° C. for 20 hours. The reaction mixture was left to be cooled to room temperature and the solvent was then evaporated under reduced pressure to obtain 1.19 g of sodium 2,2-dimethyl-5-(5-methylpyridin-2-yl)-1,3-dioxane-5-carboxylate.

Preparation Example 60

To a solution of 1.03 g of 2-(5-azide-2,2-dimethyl-1,3-dioxan-5-yl)-5-methyl-1,3-thiazole in 20 ml of acetic acid were added 1.33 g of zinc powder in a water bath, followed by stirring at room temperature overnight. The insoluble materials of the reaction mixture were separated by filtration and the filtrate was concentrated under reduced pressure. The obtained residue was purified by silica gel column to obtain 232 mg of 2,2-dimethyl-5-(5-methyl-1,3-thiazol-2-yl)-1,3-dioxan-5-amine.

Preparation Example 79

The compound was prepared using the compound of Preparation Example 25 by the same method as in Preparation Example 10 as described above.

Preparation Example 80

The compound was prepared using the compound of Preparation Example 121 by the same method as in Preparation Example 10 as described above.

Preparation Example 200

To a suspension of 1.28 g of 8-(cyclohexylmethoxy)-N-[(1R)-2-hydroxy-1-phenylethyl]-2-methylimidazo[1,2-a]pyridine-3-carboxamide prepared by the same method as in Example 1, which will be described later, in 30 ml of ethyl acetate was added 1.2 ml of a 4 M hydrogen chloride/ethyl acetate solution, followed by stirring at room temperature. The insoluble materials were collected by filtration and dried under reduced pressure to obtain 1.41 g of 8-(cyclohexylmethoxy)-N-[(1R)-2-hydroxy-1-phenylethyl]-2-methylimidazo[1,2-a]pyridine-3-carboxamide hydrochloride.

Preparation Example 214

The compound was prepared using the compound of Preparation Example 26 by the same method as in Preparation Example 8, which will be described later.

Preparation Example 263

A mixture of 317 mg of tert-butyl 4-cyano-2,2,4-trimethyl-1,3-oxazolidine-3-carboxylate, 307 mg of trimethylsilyl azide, 67 mg of dibutyltin oxide, and 10 ml of toluene was stirred for 8 hours under heating to reflux. The reaction mixture was left to be cooled to room temperature and then concentrated under reduced pressure. The obtained residue was purified by silica gel column chromatography to obtain 168 mg of tert-butyl 2,2,4-trimethyl-4-(2H-tetrazol-5-yl)-1,3-oxazolidine-3-carboxylate.

Preparation Example 264

To a solution of 75 mg of 8-[(2,6-difluorobenzyl)oxy]-N-{2,2-dimethyl-5-[1-(tetrahydro-2H-pyran-2-yl)-1H-pyrazol-4-yl]-1,3-dioxan-5-yl}-2-methylimidazo[1,2-a]pyridine-3-carboxamide in 0.4 ml of methanol and 0.4 ml of water was added 1.6 ml of a 4 M hydrogen chloride/1,4-dioxane solution, followed by stirring at room temperature for 3 days. The reaction mixture was concentrated under reduced pressure to obtain 74 mg of 8-[(2,6-difluorobenzyl)oxy]-N-[1,3-dihydroxy-2-(1H-pyrazol-4-yl)propan-2-yl]-2-methylimidazo[1,2-a]pyridine-3-carboxamide hydrochloride.

Preparation Example 265

To a solution of 430 mg of 4-(nitromethyl)-1H-pyrazole in 4.3 ml of ethyl acetate were added 0.62 ml of 3,4-dihydro-2H-pyran and 129 mg of 4-methylbenzenesulfonic acid monohydrate, followed by stirring at room temperature for 3 hours. To the reaction mixture was added a saturated aqueous sodium hydrogen carbonate solution, followed by extraction with ethyl acetate. The organic layer was dried over anhydrous magnesium sulfate and the solvent was then evaporated under reduced pressure. The obtained residue was purified by silica gel column chromatography to obtain 213 mg of 4-(nitromethyl)-1-(tetrahydro-2H-pyran-2-yl)-1H-pyrazole.

Preparation Example 266

To a solution of 1.31 g of a mixture of ethyl 2-azide-2-(1,3-dimethyl-1H-pyrazol-4-yl)propanoate and ethyl 2-azide-2-(1,5-dimethyl-1H-pyrazol-4-yl)propanoate in 20 ml of ethyl acetate was added 130 mg of 10% palladium-carbon (hydrous), followed by stirring at room temperature for 18 hours under a hydrogen atmosphere of 1 atm. The reaction mixture was filtered over Celite and the filtrate was concentrated under reduced pressure to obtain 1.13 g of a mixture of ethyl 2-amino-2-(1,3-dimethyl-1H-pyrazol-4-yl)propanoate and ethyl 2-amino-2-(1,5-dimethyl-1H-pyrazol-4-yl)propanoate.

Preparation Example 267

To a solution of 458 mg of tert-butyl 4-(hydrazinocarbonyl)-2,2,4-trimethyl-1,3-oxazolidine-3-carboxylate in 20 ml of dichloromethane were added 0.7 ml of triethylamine and 0.5 ml of trifluoroacetic anhydride at 0° C., followed by warming to room temperature, stirring for 1 hour, and then stirring for 2 hours under heating to reflux. The reaction mixture was left to be cooled to room temperature and the solvent was then evaporated under reduced pressure. 15 ml of dichloroethane, 1.0 ml of triethylamine, and 0.5 ml of trifluoroacetic anhydride were added thereto, followed by stirring for 1 hour under heating to reflux. The reaction mixture was left to be cooled to room temperature and a saturated aqueous sodium hydrogen carbonate solution was added thereto, followed by extraction with chloroform. The organic layer was concentrated under reduced pressure and the obtained residue was purified by silica gel column chromatography to obtain 392 mg of tert-butyl 2,2,4-trimethyl-4-[5-(trifluoromethyl)-1,3,4-oxadiazol-2-yl]-1,3-oxazolidine-3-carboxylate.

Preparation Example 288

To a solution of 761 mg of 1-{[tert-butyl (dimethyl)silyl]oxy}acetone in 20 ml of THF were added 2.1 ml of tetraethyl orthotitanate and 490 mg of (S)-2-methylpropane-2-sulfinamide, followed by stirring at 70° C. for 8 hours. The reaction mixture was left to be cooled to room temperature and a saturated aqueous sodium chloride solution was then added thereto, followed by stirring and filtering over Celite. The filtrate was extracted with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain (S)—N-[(2E)-1-{[tert-butyl(dimethyl)silyl]oxy}propan-2-ylidene]-2-methylpropane-2-sulfinamide.

Preparation Example 289

Under an argon atmosphere, to a mixture of 2.47 g of N-(2-bromobenzyl)-2,2,2-trifluoroacetamide and 25 ml of toluene were added 1.02 g of tetrakis(triphenylphosphine)palladium(0) and 3.10 g of tributylvinyltin, followed by stirring at 130° C. for 17 hours. The reaction mixture was left to be cooled to room temperature, and ethyl acetate and a 10% aqueous potassium fluoride solution were then added thereto, followed by stirring. The reaction mixture was filtered over Celite and the organic layer was washed with a saturated aqueous sodium hydrogen carbonate solution and a saturated aqueous sodium chloride solution, and dried over anhydrous magnesium sulfate. The solvent was then evaporated under reduced pressure. The obtained residue was purified by silica gel column chromatography to obtain 1.71 g of 2,2,2-trifluoro-N-(2-vinylbenzyl)acetamide.

Preparation Example 291

Under a nitrogen atmosphere, a mixture of 5.0 g of 3-[(2,6-difluorobenzyl)oxy]pyridin-2-amine, 4.1 ml of ethyl 2-chloroacetoacetate, 3.5 ml of 2,6-dimethylpyridine, and 50 ml of toluene was stirred at 130° C. for 24 hours. After leaving to be cooled to room temperature, the reaction mixture was washed with water, a 1 M aqueous sodium hydroxide solution, a 10% aqueous citric acid solution, and a saturated aqueous sodium chloride solution. The organic layer was concentrated under reduced pressure to obtain 5.47 g of ethyl 8-[(2,6-difluorobenzyl)oxy]-2-methylimidazo[1,2-a]pyridine-3-carboxylate.

Preparation Example 292

To a suspension of 5.41 g of ethyl 8-[(2,6-difluorobenzyl)oxy]-2-methylimidazo[1,2-a]pyridine-3-carboxylate in 32 ml of ethanol was added dropwise 6.2 ml of a 5 M aqueous sodium hydroxide solution, followed by stirring at 60° C. for 1.5 hours. To the reaction mixture was added dropwise 15.8 ml of 2 M hydrochloric acid at 50° C., and then 1.5 ml of a 2 M hydrochloric acid was added thereto. The insoluble materials were collected by filtration and the solid was washed with ethanol/water=1:1 to obtain 3.46 g of 8-[(2,6-difluorobenzyl)oxy]-2-methylimidazo[1,2-a]pyridine-3-carboxylic acid.

Preparation Example 293

Under an argon gas flow, to a suspension of 32.5 g of 8-[(2,6-difluorobenzyl)oxy]-2-methylimidazo[1,2-a]pyridine-3-carboxylic acid in 807 ml of dichloromethane were added 190 µl of DMF and 17.2 ml of oxalyl chloride under ice-cooling, followed by stirring at room temperature for 80 minutes. The reaction mixture was concentrated under reduced pressure to obtain 38.0 g of 8-[(2,6-difluorobenzyl)oxy]-2-methylimidazo[1,2-a]pyridine-3-carbonyl chloride hydrochloride.

Preparation Example 294

Under an argon gas flow, to a mixture of 10.4 g of 5-amino-2,2-dimethyl-1,3-dioxane-5-carbonitrile, 27.8 ml of triethylamine, and 280 ml of dichloroethane were added 27.2 g of 8-[(2,6-difluorobenzyl)oxy]-2-methylimidazo[1,2-a]pyridine-3-carbonyl chloride hydrochloride and 12 ml of dichloroethane at room temperature, followed by stirring at 70° C. for 2 hours. After leaving to be cooled to room temperature, the insoluble materials were separated by filtration and washed with dichloroethane. The filtrate was washed with a 10% aqueous citric acid solution three times, and the aqueous layer was extracted with chloroform. The organic layer was combined, washed with water, a saturated aqueous sodium hydrogen carbonate solution, and a saturated aqueous sodium chloride solution, and dried over anhydrous magnesium sulfate, and the solvent was then evaporated under reduced pressure. The obtained residue was azeotropic distilled with ethyl acetate twice. To the obtained residue was added THF, and the insoluble materials were separated by filtration and washed with THF. The filtrate was concentrated and the residue was purified by silica gel column chromatography to obtain 27.7 g of N-(5-cyano-2,2-dimethyl-1,3-dioxan-5-yl)-8-[(2,6-difluorobenzyl)oxy]-2-methylimidazo[1,2-a]pyridine-3-carboxamide.

Preparation Example 295

Under a nitrogen gas flow, to a solution of 27.7 g of N-(5-cyano-2,2-dimethyl-1,3-dioxan-5-yl)-8-[(2,6-difluorobenzyl)oxy]-2-methylimidazo[1,2-a]pyridine-3-carboxamide in 280 ml of DMF were added 10.0 g of ammonium chloride and 12.0 g of sodium azide at room temperature, followed by stirring at 120° C. for 2 hours. The reaction mixture was left to be cooled to room temperature, and the insoluble materials were then separated by filtration and washed with DMF. The filtrate was added to water, followed by stirring at room temperature for 2 days. The resulting insoluble materials were separated by filtration and washed with water. The obtained residue was dried under reduced pressure to obtain 29.2 g of 8-[(2,6-difluorobenzyl)oxy]-N-[2,2-dimethyl-5-(2H-tetrazol-5-yl)-1,3-dioxan-5-yl]-2-methylimidazo[1,2-a]pyridine-3-carboxamide.

Preparation Example 296

Under a nitrogen gas flow, to a mixture of 1.1 g of potassium carbonate and 13 ml of DMF was added dropwise a mixture of 1.92 g of 8-[(2,6-difluorobenzyl)oxy]-N-[2,2-dimethyl-5-(2H-tetrazol-5-yl)-1,3-dioxan-5-yl]-2-methylimidazo[1,2-a]pyridine-3-carboxamide, 1.2 g of sodium chlorodifluoroacetate, and 11 ml of DMF at 108° C., followed by stirring at the same temperature for 10 minutes. The reaction mixture was left to be cooled to room temperature, and water was added thereto, followed by extraction with ethyl acetate. The organic layer was washed with water and a saturated aqueous sodium chloride solution, and dried over anhydrous magnesium sulfate, and the solvent was then evaporated under reduced pressure. To the obtained residue was added 12 ml of ethanol, followed by stirring at 70° C. for 30 minutes and at room temperature for 3 days. The insoluble materials were collected by filtration, washed with ethanol, and dried under reduced pressure to obtain 1.51 g of a mixture (about 2:1) of 8-[(2,6-difluorobenzyl)oxy]-N-{5-[2-(difluoromethyl)-2H-tetrazol-5-yl]-2,2-dimethyl-1,3-dioxan-5-yl}-2-methylimidazo[1,2-a]pyridine-3-carboxamide and 8-[(2,6-difluorobenzyl)oxy]-N-{5-[1-(difluoromethyl)-1H-tetrazol-5-yl]-2,2-dimethyl-1,3-dioxan-5-yl}-2-methylimidazo[1,2-a]pyridine-3-carboxamide.

Preparation Example 297

Under a nitrogen gas flow, to a mixture of 11.0 g of tert-butyl (4S)-4-carbamoyl-2,2,4-trimethyl-1,3-oxazolidine-3-carboxylate and 170 ml of THF were added dropwise 11.0 ml of triethylamine and 8.0 ml of trifluoroacetic anhydride under ice-cooling, followed by warming to room temperature and stirring for 30 minutes. The reaction mixture was added to water, followed by extraction with ethyl acetate. The organic layer was washed with a 10% aqueous citric acid solution, a saturated aqueous sodium hydrogen carbonate solution, and a saturated aqueous sodium chloride solution, and dried over anhydrous magnesium sulfate. The solvent was evaporated under reduced pressure to obtain 8.22 g of tert-butyl (4R)-4-cyano-2,2,4-trimethyl-1,3-oxazolidine-3-carboxylate.

Preparation Example 298

To a mixture of 6.96 g of tert-butyl (4R)-4-cyano-2,2,4-trimethyl-1,3-oxazolidine-3-carboxylate, 12.5 g of triethylamine hydrochloride, and 105 ml of toluene was added 5.84 g of sodium azide, followed by stirring at 103° C. for 3 hours. The insoluble materials were separated by filtration and the filtrate was concentrated. The obtained residue was purified twice by silica gel column chromatography to obtain 7.65 g of tert-butyl (4R)-2,2,4-trimethyl-4-(2H-tetrazol-5-yl)-1,3-oxazolidine-3-carboxylate.

Preparation Example 299

Under a nitrogen gas flow, to a mixture of 9.89 g of tert-butyl (4R)-2,2,4-trimethyl-4-(2H-tetrazol-5-yl)-1,3-oxazolidine-3-carboxylate, 11 g of potassium carbonate, and 200 ml of acetonitrile was added dropwise 7.5 ml of 2,2-difluoro-2-(fluorosulfonyl)acetic acid under ice-cooling, followed by warming to room temperature and stirring for 1 hour. The reaction mixture was added to a saturated aqueous sodium hydrogen carbonate solution, followed by extraction with ethyl acetate. The organic layer was washed with a saturated aqueous sodium chloride solution and dried over anhydrous magnesium sulfate, and the solvent was then evaporated under reduced pressure. The obtained residue was purified by silica gel column chromatography to obtain 7.59 g of tert-butyl (4R)-4-[2-(difluoromethyl)-2H-tetrazol-5-yl]-2,2,4-trimethyl-1,3-oxazolidine-3-carboxylate.

Preparation Example 300

To a solution of 8.76 g of tert-butyl (4R)-4-[2-(difluoromethyl)-2H-tetrazol-5-yl]-2,2,4-trimethyl-1,3-oxazolidine-3-carboxylate in 40 ml of dichloromethane was added 20 ml of trifluoroacetic acid, followed by stirring at room temperature for 4 hours. The reaction mixture was concentrated under reduced pressure and the residue was azeotropic distilled with toluene three times. To a solution of the obtained residue in 80 ml of DMF were added 9.05 g of 1H-imidazole and 6.10 g of tert-butyl dimethylchlorosilane, followed by stirring at room temperature overnight. To the reaction mixture was added water, followed by extraction with ethyl acetate. The organic layer was washed with water, and a saturated aqueous sodium chloride solution, followed by drying over anhydrous magnesium sulfate. The solvent was then evaporated under reduced pressure. The obtained residue was purified by silica gel column chromatography to obtain 7.84 g of (2R)-1-{[tert-butyl(dimethyl)silyl]oxy}-2-[2-(difluoromethyl)-2H-tetrazol-5-yl]propan-2-amine.

Preparation Example 301

Under a nitrogen atmosphere, to a mixture of 5.55 g of (2R)-1-{[tert-butyl(dimethyl)silyl]oxy}-2-[2-(difluoromethyl)-2H-tetrazol-5-yl]propan-2-amine, 7.5 ml of triethylamine, 220 mg of 4-dimethylaminopyridine, and 110 ml of 1,2-dichloroethane was added 8.88 g of 8-[(2,6-difluorobenzyl)oxy]-2-methylimidazo[1,2-a]pyridine-3-carbonyl chloride hydrochloride, followed by stirring at 70° C. for 2 hours. The reaction mixture was left to be cooled to room temperature, and was added to the mixture of water and ethyl acetate. The insoluble materials were separated by filtration and washed with ethyl acetate, and the aqueous layer was extracted with ethyl acetate. The organic layer was combined, washed with water and a saturated aqueous sodium chloride solution, and dried over anhydrous magnesium sulfate, and the solvent was evaporated under reduced pressure. The obtained residue was purified by silica gel column chromatography to obtain 8.70 g of N-{(2R)-1-{[tert-butyl (dimethyl)silyl]oxy}-2-[2-(difluoromethyl)-2H-tetrazol-5-yl] propan-2-yl}-8-[(2,6-difluorobenzyl)oxy]-2-methylimidazo [1,2-a]pyridine-3-carboxamide.

Preparation Example 302

To a mixture of 1.00 g of (4S)-3-(tert-butoxycarbonyl)-2, 2,4-trimethyl-1,3-oxazolidine-4-carboxylic acid, 400 mg of acetohydrazide, 850 mg of 1-hydroxybenzotriazole, 2.0 ml of diisopropylethylamine, and 20 ml of DMF was added 1.2 g of N-[3-(dimethylamino)propyl]-N'-ethylcarbodiimide hydrochloride, followed by stirring at room temperature for 5 hours. To the reaction mixture was added water, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography to obtain 1.11 g of tert-butyl (4S)-4-[(2-acetylhydrazino)carbonyl]-2,2,4-trimethyl-1,3-oxazolidine-3-carboxylate.

Preparation Example 303

To a solution of 1.11 g of tert-butyl (4S)-4-[(2-acetylhydrazino)carbonyl]-2,2,4-trimethyl-1,3-oxazolidine-3-carboxylate in 25 ml of dichloroethane was added 1.0 g of a Burgess reagent ((methoxycarbonylsulfamoyl)triethylammonium hydroxide inner salt), followed by stirring at 80° C. for 2 hours. The reaction mixture was concentrated under reduced pressure and the obtained residue was purified by silica gel column chromatography to obtain 845 mg of tert-butyl of (4S)-2,2,4-trimethyl-4-(5-methyl-1,3,4-oxadiazol-2-yl)-1,3-oxazolidine-3-carboxylate.

Preparation Example 304

To a solution of 220 mg of tert-butyl (4S)-2,2,4-trimethyl-4-(5-methyl-1,3,4-oxadiazol-2-yl)-1,3-oxazolidine-3-carboxylate in 3.0 ml of dichloromethane was added 1.5 ml of trifluoroacetic acid, followed by stirring at room temperature for 3 hours. The reaction mixture was concentrated under reduced pressure and the obtained residue was azeotropic distilled with methanol to obtain 266 mg of (2S)-2-amino-2-(5-methyl-1,3,4-oxadiazol-2-yl)propan-1-ol trifluoroacetate as a crude product, which was used for the next reaction without further purification.

Preparation Example 305

To a solution of 3.36 g of tert-butyl (4S)-4-[(2-acetylhydrazino)carbonyl]-2,2,4-trimethyl-1,3-oxazolidine-3-carboxylate in 100 ml of toluene was added 2.8 g of 2,4-bis(4-methoxyphenyl)-1,3,2,4-dithiadiphosphetane-2,4-disulfide, followed by stirring at 110° C. for 4 hours. The reaction mixture was concentrated under reduced pressure and the obtained residue was purified by silica gel column chromatography to obtain 2.39 g of tert-butyl (4S)-2,2,4-trimethyl-4-(5-methyl-1,3,4-thiadiazol-2-yl)-1,3-oxazolidine-3-carboxylate.

Preparation Example 306

To a solution of 1.2 g of tert-butyl (4S)-2,2,4-trimethyl-4-(5-methyl-1,3,4-thiadiazol-2-yl)-1,3-oxazolidine-3-carboxylate in 12 ml of dichloromethane was added 4 ml of trifluoroacetic acid, followed by stirring at room temperature for 4 hours. The reaction mixture was concentrated under reduced pressure and the obtained residue was azeotropic distilled with methanol to obtain 1.59 g of (2S)-2-amino-2-(5-methyl-1,3,4-thiadiazol-2-yl)propan-1-ol trifluoroacetate as a crude product.

Preparation Example 307

803 mg of (2S)-2-amino-2-(5-methyl-1,3,4-thiadiazol-2-yl)propan-1-ol trifluoroacetate was purified by silica gel column chromatography (Yamazen Hi-Flash Column (registered trademark) Amino 40 μm, 36 g) to obtain 330 mg of (2S)-2-amino-2-(5-methyl-1,3,4-thiadiazol-2-yl)propan-1-ol.

Hereinafter, the preparation methods for the compounds of the formula (I) of the present invention are shown as Examples. Further, the compounds of Examples 9 to 104, 106, 109 to 111 were prepared in the same manner as the methods described in Examples 1 to 8, 105, 107 and 108, which will be described later, and Preparation Examples 8, 11, 16, and 47 as described above, and thus, they are described only in Tables, which will be described later.

Example 1

To a mixture of 165 mg of 8-[(2,6-difluorobenzyl)oxy]-2-methylimidazo[1,2-a]pyridine-3-carboxylic acid, 160 mg of 2-amino-2-(5-ethyl-1,3,4-oxadiazol-2-yl)propan-1-ol trifluoroacetate, 90 mg of 1-hydroxybenzotriazole, 0.35 ml of diisopropylethylamine, and 4 ml of DMF was added 130 mg of N-[3-(dimethylamino)propyl]-N'-ethylcarbodiimide hydrochloride, followed by stirring at room temperature overnight. To the reaction mixture was added water, followed by extraction with ethyl acetate. The organic layer was washed with water and a saturated aqueous sodium chloride solution, and the organic layer was dried over anhydrous magnesium sulfate. The solvent was then evaporated under reduced pressure. The obtained residue was purified by silica gel column chromatography. To the obtained crude product were added ethyl acetate and diisopropyl ether, and the insoluble materials were collected by filtration, and dried under reduced pressure to obtain 59 mg of 8-[(2,6-difluorobenzyl)oxy]-N-[2-(5-ethyl-1,3,4-oxadiazol-2-yl)-1-hydroxypropan-2-yl]-2-methylimidazo[1,2-a]pyridine-3-carboxamide.

Example 2

To a solution of 110 mg of ethyl 2-[({8-[(2,6-difluorobenzyl)oxy]-2-methylimidazo[1,2-a]pyridin-3-yl}carbonyl)amino]-2-(2-methyl-1,3-thiazol-5-yl)propanoate in 3.3 ml of ethanol and 0.66 ml of tetrahydrofuran were added 40 mg of sodium borohydride at 0° C., followed by stirring at room temperature for 16 hours. To the reaction mixture was added water, followed by extraction with chloroform. The organic layer was dried over anhydrous magnesium sulfate and the solvent was then evaporated under reduced pressure. The obtained residue was purified by silica gel column chromatography to obtain 80 mg of 8-[(2,6-difluorobenzyl)oxy]-N-[1-hydroxy-2-(2-methyl-1,3-thiazol-5-yl)propan-2-yl]-2-methylimidazo[1,2-a]pyridine-3-carboxamide.

Example 3

To a mixture of 86 mg of methyl 3-[(2R)-2-({[8-(cyclohexylmethoxy)-2-methylimidazo[1,2-a]pyridin-3-yl]carbonyl}amino)-1-hydroxypropan-2-yl]benzoate, 1.9 ml of methanol, and 1.9 ml of THF was added 0.36 ml of a 1 M aqueous sodium hydroxide solution, followed by stirring at 40° C. for 16 hours. The reaction mixture was left to be cooled to room temperature and 1 M hydrochloric acid was then added thereto, followed by extraction with chloroform. The organic layer was dried over anhydrous magnesium sulfate and the solvent was then evaporated under reduced pressure. The obtained residue was purified by silica gel column chromatography to obtain 52 mg of 3-[(2R)-2-({ [8-(cyclohexylmethoxy)-2-methylimidazo[1,2-a]pyridin-3-yl]carbonyl}amino)-1-hydroxypropan-2-yl]benzoic acid.

Example 4

To a solution of 35 mg of methyl 4-{2-[({8-[(2,6-difluorobenzyl)oxy]-2-methylimidazo[1,2-a]pyridin-3-yl}carbonyl)amino]-1-hydroxypropan-2-yl}benzoate in 1.4 ml of THF were added dropwise 0.17 ml of a 1 M diisobutylaluminum hydride/toluene solution at −78° C., followed by stirring at 0° C. for 3 hours. To the reaction mixture was added 0.14 ml of a 1 M diisobutylaluminum hydride/toluene solution at 0° C., followed by stirring for 1 hour. To the reaction mixture was added a saturated aqueous Rochelle salt solution, followed by extraction with ethyl acetate. The organic layer was washed with a saturated aqueous sodium chloride solution and dried over anhydrous magnesium sulfate, and the solvent was then evaporated. The residue was purified by silica gel column chromatography to obtain 20 mg of 8-[(2,6-difluorobenzyl)oxy]-N-{1-hydroxy-2-[4-(hydroxymethyl)phenyl]propan-2-yl}-2-methylimidazo[1,2-a]pyridine-3-carboxamide.

Example 5

To a mixture of 273 mg of 8-[(2,6-difluorobenzyl)oxy]-N-[2-(2,2-dimethyl-1,3-dioxolan-4-yl)benzyl]-2-methylimidazo[1,2-a]pyridine-3-carboxamide, 3 ml of dioxane, and 3 ml of methanol was added 6 ml of 1 M hydrochloric acid under ice-cooling, followed by stirring at room temperature for 16 hours. The reaction mixture was ice-cooled and 0.6 g of sodium hydrogen carbonate was added thereto in small portions to make the mixture weakly basic. The precipitated solid was collected by filtration and washed with water to obtain 236 mg of 8-[(2,6-difluorobenzyl)oxy]-N-[2-(1,2-dihydroxyethyl)benzyl]-2-methylimidazo[1,2-a]pyridine-3-carboxamide.

Example 6

To a mixture of 153 mg of potassium carbonate and 5 ml of DMF was added dropwise a solution of 346 mg of N-[1-{[tert-butyl (diphenyl)silyl]oxy}-2-(2H-tetrazol-5-yl)propan-2-yl]-8-[(2,6-difluorobenzyl)oxy]-2-methylimidazo[1,2-a]pyridine-3-carboxamide and 158 mg of sodium chloro(difluoro)acetate in 3 ml of DMF at an inner temperature of 95° C., followed by stirring at the same temperature for 1 hour. After leaving to be cooled to room temperature, water was added thereto, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography. To the obtained crude product were added ethyl acetate and diisopropyl ether, and the insoluble materials were collected by filtration and dried under reduced pressure to obtain 98 mg of 8-[(2,6-difluorobenzyl)oxy]-N-{2-[2-(difluoromethyl)-2H-tetrazol-5-yl]-1-hydroxypropan-2-yl}-2-methylimidazo[1,2-a]pyridine-3-carboxamide.

Example 7

To a solution of 245 mg of 8-[(2,6-difluorobenzyl)oxy]-N-[1-hydroxy-2-(2H-tetrazol-5-yl)propan-2-yl]-2-methylimidazo[1,2-a]pyridine-3-carboxamide in 5 ml of DMF were added 200 mg of potassium carbonate and 50 μl of methyl iodide, followed by stirring at room temperature for 2 hours. To the reaction mixture was added water, followed by extraction with ethyl acetate. The organic layer was washed with water and a saturated aqueous sodium chloride solution, and dried over anhydrous magnesium sulfate, and the solvent was then evaporated under reduced pressure. The obtained residue was purified by silica gel column chromatography. To the obtained crude product were added isopropyl alcohol and diisopropyl ether, and the insoluble materials were collected by filtration and dried under reduced pressure to obtain 73 mg of 8-[(2,6-difluorobenzyl)oxy]-N-[1-hydroxy-2-(2-methyl-2H-tetrazol-5-yl)propan-2-yl]-2-methylimidazo[1,2-a]pyridine-3-carboxamide (Ex7a). Further, to the other crude product was added diisopropyl ether, and the insoluble materials were collected by filtration and dried under reduced pressure to obtain 27 mg of 8-[(2,6-difluorobenzyl)oxy]-N-[1-hydroxy-2-(1-methyl-1H-tetrazol-5-yl)propan-2-yl]-2-methylimidazo[1,2-a]pyridine-3-carboxamide (Ex7b).

Example 8

To a solution of 137 mg of N-[1-{[tert-butyl (diphenyl)silyl]oxy}-2-(2-ethyl-2H-tetrazol-5-yl)propan-2-yl]-8-[(2,6-difluorobenzyl)oxy]-2-methylimidazo[1,2-a]pyridine-3-carboxamide in 3 ml of THF was added 0.3 ml of a 1 M tetrabutylammonium fluoride/THF solution, followed by stirring at room temperature for 2 hours. The reaction mixture was concentrated under reduced pressure and the obtained residue was purified by silica gel column chromatography. To the obtained crude product was added ethyl acetate, and the insoluble materials were collected by filtration, washed with diisopropyl ether, and dried under reduced pressure to obtain 75 mg of 8-[(2,6-difluorobenzyl)oxy]-N-[2-(2-ethyl-2H-tetrazol-5-yl)-1-hydroxypropan-2-yl]-2-methylimidazo[1,2-a]pyridine-3-carboxamide.

Example 105

To a solution of 180 mg of N-[1-{[tert-butyl (diphenyl)silyl]oxy}-2-(2H-tetrazol-5-yl)propan-2-yl]-8-[(2,6-difluorobenzyl)oxy]-2-methylimidazo[1,2-a]pyridine-3-carboxamide in 3 ml of DMF were added 100 mg of potassium carbonate and 50 μl of 2,2-dimethyloxirane, followed by stirring at 60° C. for 4 hours and then at 100° C. overnight. To the reaction mixture were added 100 mg of potassium carbonate and 50 μl of 2,2-dimethyloxirane, followed by stirring at 140° C. for 1 hour under the microwave irradiation condition. To the reaction mixture was added 50 μl of 2,2-dimethyloxirane, followed by stirring at 150° C. for 1 hour under the microwave irradiation condition. To the reaction mixture was added water, followed by extraction with ethyl acetate. The organic layer was washed with water and a saturated aqueous sodium chloride solution, and dried over anhydrous magnesium sulfate, and the solvent was then evaporated. The obtained residue was purified by silica gel column chromatography. To the obtained crude product were added ethyl acetate and diisopropyl ether, and the insoluble materials were collected by filtration and dried under reduced pressure to obtain 42 mg of 8-[(2,6-difluorobenzyl)oxy]-N-{1-hydroxy-2-[2-(2-hydroxy-2-methylpropyl)-2H-tetrazol-5-yl]propan-2-yl}-2-methylimidazo[1,2-a]pyridine-3-carboxamide.

Example 107

106 mg of 8-[(2,6-difluorobenzyl)oxy]-N-{1-hydroxy-2-[4-(hydroxymethyl)phenyl]propan-2-yl}-2-methylimidazo[1,2-a]pyridine-3-carboxamide was separated under the preparative condition A, using an supercritical fluid chromatography device manufactured by Waters, thus to obtain 41 mg of an optical isomer (Ex107a) and 39 mg of the other optical isomer (Ex107b), respectively.

Example 108

370 mg of 8-[(2,6-difluorobenzyl)oxy]-N-[1-hydroxy-2-(2-methyl-2H-tetrazol-5-yl)propan-2-yl]-2-methylimidazo[1,2-a]pyridine-3-carboxamide was separated under the preparative condition B, using an supercritical fluid chromatography device manufactured by Waters. To each of the optical isomers were added ethyl acetate and diisopropyl ether. The insoluble materials were collected by filtration and dried under reduced pressure to obtain 140 mg (Ex108a) and 136 mg (Ex108b), respectively.

Example 112

23.6 g of a mixture of 8-[(2,6-difluorobenzyl)oxy]-N-{5-[2-(difluoromethyl)-2H-tetrazol-5-yl]-2,2-dimethyl-1,3-dioxan-5-yl}-2-methylimidazo[1,2-a]pyridine-3-carboxamide and 8-[(2,6-difluorobenzyl)oxy]-N-{5-[1-(difluoromethyl)-1H-tetrazol-5-yl]-2,2-dimethyl-1,3-dioxan-5-yl}-2-methylimidazo[1,2-a]pyridine-3-carboxamide, a mixture of 220 ml of methanol and 220 ml of 1 M hydrochloric acid was stirred at room temperature for 14 hours. The reaction mixture was concentrated under reduced pressure and a saturated aqueous sodium hydrogen carbonate solution was added thereto, followed by extraction with chloroform/methanol=9:1. The organic layer was washed with a saturated aqueous sodium chloride solution and dried over anhydrous sodium sulfate, and the solvent was then evaporated under reduced pressure. The obtained residue was purified by silica gel column chromatography to obtain 15.1 g of a crude product. To this crude product were added 30 ml of ethyl acetate and 150 ml of diisopropyl ether, followed by stirring at room temperature for 1 hour. The insoluble materials were separated by filtration, and the solid was washed with 100 ml of diisopropyl ether and dried under reduced pressure to obtain 12.9 g of 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide.

Example 113

To a solution of 459 mg of 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide in 1.85 ml of ethanol was added dropwise 105 μl of 47% hydrobromic acid, followed by stirring at room temperature for 4 days. The insoluble materials were collected by filtration, washed with 460 μl of ethanol, and dried under reduced pressure to obtain 443 mg of a crystal of 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide hydrobromide.

The crystal obtained in Example 113 has peaks at around 2θ (°) 7.9, 8.8, 10.2, 11.1, 13.1, 13.5, 13.7, 14.4, 14.7, and 15.8 with powder X-ray diffraction.

Example 114

To a solution of 463 mg of N-{(2R)-1-{[tert-butyl (dimethyl)silyl]oxy}-2-[2-(difluoromethyl)-2H-tetrazol-5-yl] propan-2-yl}-8-[(2,6-difluorobenzyl)oxy]-2-methylimidazo[1,2-a]pyridine-3-carboxamide in 8 ml of THF was added 1 ml of a 1 M tetrabutylammonium fluoride/THF solution, followed by stirring at room temperature for 2 hours. To the reaction mixture was added water, followed by extraction with chloroform. The organic layer was concentrated under reduced pressure and the obtained residue was purified by silica gel column chromatography. To the obtained crude product was added ethyl acetate, and diisopropyl ether was further added thereto. The mixture was stirred for 1 hour in an oil bath at 85° C., left to be cooled to room temperature, and stirred overnight. The insoluble materials were collected by filtration and the solid was washed with diisopropyl ether to obtain 260 mg of 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide.

Example 115

To a mixture of 94.1 mg of 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide and 750 μl of ethanol was added dropwise 21 μl of 47% hydrobromic acid at 50° C., left to be cooled to room temperature, and stirred overnight. The insoluble materials were separated by filtration, and the solid was washed with 100 of ethanol and dried under reduced pressure to obtain 45 mg of a crystal of 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide hydrobromide.

The crystal obtained in Example 115 has peaks at around 2θ (°) 5.6, 9.9, 10.2, 11.2, 12.2, 12.4, 13.1, 14.7, 14.9, and 15.6 with powder X-ray diffraction.

Example 116

To a mixture of 400 mg of 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide and 3.2 ml of ethanol was added 300 mg of benzenesulfonic monohydrate at 55° C. To the reaction mixture was added 6.4 ml of ethyl acetate at 40° C. to 50° C., left to be cooled to room temperature, and stirred overnight. The insoluble materials were separated by filtration, and the solid was washed with ethyl acetate and dried under reduced pressure to obtain 503 mg of a crystal of 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide benzenesulfonate.

The crystal obtained in Example 116 has peaks at around 2θ (°) 5.7, 9.6, 10.2, 11.0, 12.4, 14.2, 16.3, 17.2, 18.8, and 19.1 with powder X-ray diffraction.

Example 117

To a mixture of 102 mg of (2S)-2-amino-2-(5-methyl-1,3,4-oxadiazol-2-yl)propan-1-ol trifluoroacetate and 6 ml of dichloromethane were added 500 μl of triethylamine and 422 mg of 8-[(2,6-difluorobenzyl)oxy]-2-methylimidazo[1,2-a]pyridine-3-carbonyl chloride hydrochloride under ice-cooling, followed by stirring at room temperature overnight. To the reaction mixture were added water and chloroform, and the aqueous layer was extracted with chloroform. The organic layer was combined and concentrated under reduced pressure, and the obtained residue was purified by silica gel column chromatography to obtain 124 mg of a crystal of 8-[(2,6-difluorobenzyl)oxy]-N-[(2S)-1-hydroxy-2-(5-methyl-1,3,4-oxadiazol-2-yl)propan-2-yl]-2-methylimidazo[1,2-a]pyridine-3-carboxamide.

The crystal obtained in Example 117 has peaks at around 2θ (°) 10.6, 11.3, 13.7, 14.5, 15.2, 16.4, 17.1, 17.7, 18.8, and 19.3 with powder X-ray diffraction.

Example 118

To a mixture of 750 mg of 8-[(2,6-difluorobenzyl)oxy]-2-methylimidazo[1,2-a]pyridine-3-carboxylic acid, 325 mg of (2S)-2-amino-2-(5-methyl-1,3,4-thiadiazol-2-yl)propan-1-ol, 400 mg of 1-hydroxybenzotriazole, 1.5 ml of diisopropylethylamine, and 18 ml of DMF was added 550 mg of N-[3-(dimethylamino)propyl]-N'-ethylcarbodiimide hydrochloride, followed by stirring at room temperature overnight. To the reaction mixture was added ethyl acetate, followed by washing with water and a saturated aqueous sodium chloride solution. The organic layer was dried over anhydrous magnesium sulfate and the solvent was then evaporated under reduced pressure. The obtained residue was purified by silica gel column chromatography to obtain 184 mg of a crystal of 8-[(2,6-difluorobenzyl)oxy]-N-[(2S)-1-hydroxy-2-(5-methyl-1,3,4-thiadiazol-2-yl)propan-2-yl]-2-methylimidazo[1,2-a]pyridine-3-carboxamide.

The crystal obtained in Example 118 has peaks at around 2θ (°) 8.3, 10.9, 11.4, 12.1, 12.9, 13.9, 14.6, 15.1, 16.6, and 17.1 with powder X-ray diffraction.

For the Preparation Example Compounds, the structures are shown in Tables 4 to 39, which will be described later, and the physicochemical data and preparation methods are shown in Tables 40 to 51, which will be described later.

For the Example Compounds, the structures are shown in Tables 52 to 73, which will be described later, and the physicochemical data and preparation methods are shown in Tables 74 to 83, which will be described later.

TABLE 4

| PEx | Str |
| --- | --- |
| 1 | 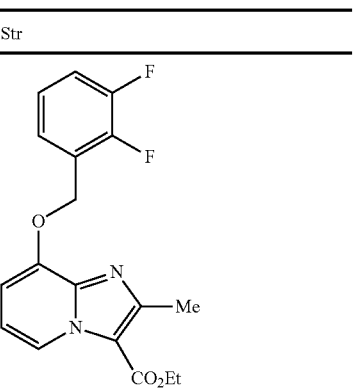 |

TABLE 4-continued

| PEx | Str |
|---|---|
| 2 | 8-(cyclohexylmethoxy)-2-methylimidazo[1,2-a]pyridine-3-carboxylic acid ethyl ester |
| 3 | 8-[(3-fluoropyridin-2-yl)methoxy]-2-methylimidazo[1,2-a]pyridine-3-carboxylic acid ethyl ester |
| 4 | ethyl 2-(benzhydrylideneamino)-2-(1-methyl-1H-pyrazol-4-yl)acetate |
| 5 | tert-butyl (2-((Z)-prop-1-enyl)benzyl)carbamate |
| 6 | methyl 4-(1-nitroethyl)benzoate |
| 7 | ethyl 2-amino-2-(1-methyl-1H-pyrazol-4-yl)acetate |
| 8 | 2-amino-2-(5-methylthiazol-2-yl)ethanol hydrochloride |
| 9 | tert-butyl (1-(2H-tetrazol-5-yl)-2-(benzyloxy)ethyl)carbamate |

TABLE 4-continued

| PEx | Str |
|---|---|
| 10 | tert-butyl (1-(2-methyl-2H-tetrazol-5-yl)-2-hydroxyethyl)carbamate |
| 11 | 2-amino-2-(2-methyl-2H-tetrazol-5-yl)ethanol hydrochloride |
| 12 | (2-(2,2-dimethyl-1,3-dioxolan-4-yl)phenyl)methanamine |

TABLE 5

| PEx | Str |
|---|---|
| 13 | 2-amino-2-(5-methylthiazol-2-yl)-3-((tert-butyldimethylsilyl)oxy)-2-methylpropan-1-ol |
| 14 | 2-amino-2-(5-methyl-1,3,4-oxadiazol-2-yl)propan-1-ol TFA |
| 15 | ethyl 2-(8-((2,6-difluorobenzyl)oxy)-2-methylimidazo[1,2-a]pyridine-3-carboxamido)-2-(pyrimidin-5-yl)propanoate |

TABLE 5-continued

| PEx | Str |
|---|---|
| 16 | (2,6-difluorobenzyloxy)-2-methyl-N-[2-(2,2-dimethyl-1,3-dioxolan-4-yl)benzyl]imidazo[1,2-a]pyridine-3-carboxamide |
| 17a | (R)-N-[(1-(5-methylthiazol-2-yl)-2-(OTBS)ethyl)]-tert-butanesulfinamide |
| 17b | (S)-N-[(1-(5-methylthiazol-2-yl)-2-(OTBS)ethyl)]-tert-butanesulfinamide |
| 18a | tBu-S(O)-NH-C(Me)(Ph)-CH2-OTBS (one isomer) |
| 18b | tBu-S(O)-NH-C(Me)(Ph)-CH2-OTBS (other isomer) |
| 19 | tBu-S(O)-NH-C(Me)(3-CO2Me-C6H4)-CH2-OTBS |
| 20 | ethyl 2-hydroxy-2-(2-methylthiazol-5-yl)propanoate |

TABLE 6

| PEx | Str |
|---|---|
| 21 | 5-(4-methylpyridin-2-yl)-2,2-dimethyl-1,3-dioxan-5-ol |
| 22 | 1-phenyl-1-(NHBoc)cyclopent-3-ene |
| 23 | 5-(OTBDPS-methyl)thiazole |
| 24 | ethyl 5-(NHZ)-2,2-dimethyl-1,3-dioxane-5-carboxylate |
| 25 | 5-(5-methylpyridin-2-yl)-5-(NHZ)-2,2-dimethyl-1,3-dioxane |
| 26 | 2-(trimethylsilyl)ethyl [5-(5-chloropyridin-2-yl)-2,2-dimethyl-1,3-dioxan-5-yl]carbamate |
| 27 | 2-amino-2-(pyrimidin-2-yl)propan-1-ol |
| 28 | 5-amino-5-(4-fluorophenyl)-2,2-dimethyl-1,3-dioxane |

TABLE 6-continued

| PEx | Str |
|---|---|
| 29 | 2-amino-2-(1-methyl-1H-pyrazol-4-yl)propanoic acid ethyl ester |
| 30 | 5-(3-(methoxycarbonyl)phenyl)-2,2-dimethyl-1,3-dioxan-5-amine |
| 31 | ethyl 2-((diphenylmethylene)amino)-2-(pyrimidin-5-yl)propanoate |
| 32 | methyl 4-(1-hydroxy-2-methyl-2-nitropropan-2-yl)benzoate |
| 33 | methyl 2-(1,3-dihydroxy-2-(5-methylpyridin-2-yl)propan-2-yl)... |
| 34 | ethyl 2-hydroxy-2-(1-methyl-1H-pyrazol-4-yl)propanoate |

TABLE 7

| PEx | Str |
|---|---|
| 35 | 5-bromo-4-((di-Boc-amino)methyl)pyridine |
| 36 | ethyl 2-azido-2-(1-methyl-1H-pyrazol-4-yl)propanoate |
| 37 | methyl 3-(nitromethyl)benzoate |
| 38 | (E)-6-methoxynicotinaldehyde oxime |
| 39 | 2-methoxy-5-(nitromethyl)pyridine |
| 40 | tert-butyl (1-phenyl-6-oxabicyclo[3.1.0]hexan-2-yl)carbamate (two diastereomers) |
| 41 | tert-butyl ((1R,3S,4R)-3,4-dihydroxy-1-phenylcyclopentyl)carbamate (rac) |
| 42 | ethyl 2-(1,5-dimethyl-1H-pyrazol-4-yl)-2-oxoacetate and ethyl 2-(1,3-dimethyl-1H-pyrazol-4-yl)-2-oxoacetate |
| 43 | (1S,2R,3S)-3-azido-3-phenylcyclopentane-1,2-diol (rac) |
| 44 | N-(2-(1,2-dihydroxyethyl)benzyl)-2,2,2-trifluoroacetamide |

TABLE 7-continued

| PEx | Str |
|---|---|
| 45 | (structure) |
| 46 | (structure) |

TABLE 8

| PEx | Str |
|---|---|
| 47 | (structure) |
| 48 | (structure) |
| 49 | (structure) |

TABLE 8-continued

| PEx | Str |
|---|---|
| 50 | (structure) |
| 51 | (structure) |
| 52 | (structure) |
| 53 | (structure) |
| 54 | (structure) |

TABLE 9
| PEx | Str |
|---|---|
| 55 | 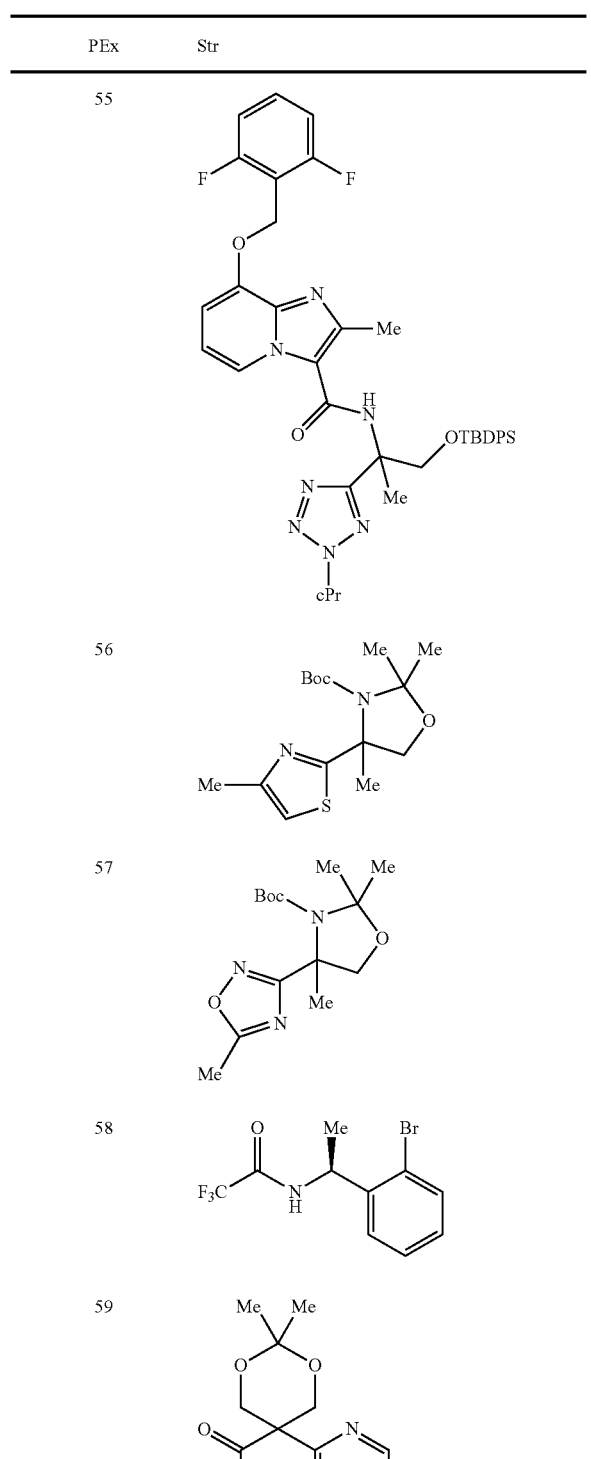 |
| 56 | |
| 57 | |
| 58 | |
| 59 | |
| 60 | |
TABLE 9-continued
| PEx | Str |
|---|---|
| 61 | 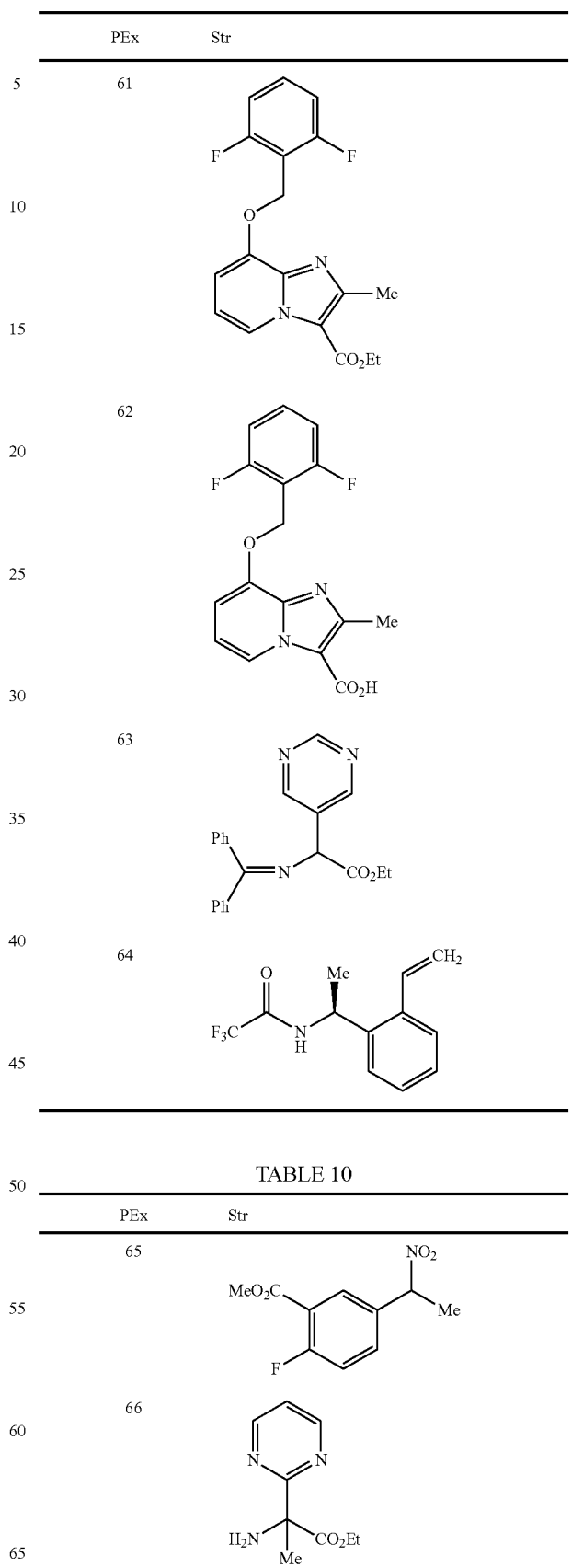 |
| 62 | |
| 63 | |
| 64 | |
TABLE 10
| PEx | Str |
|---|---|
| 65 | |
| 66 | |

TABLE 10-continued
| PEx | Str |
|---|---|
| 67 | 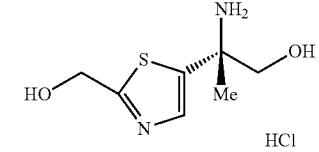 [SMILES: C[C@@](N)(CO)c1cnc(CO)s1 ; Cl] |
| 68 | 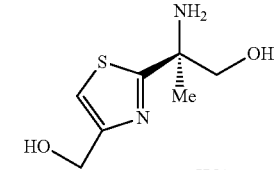 |
| 69 | 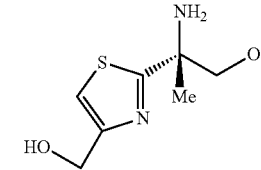 |
| 70 | 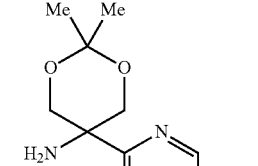 |
| 71 | 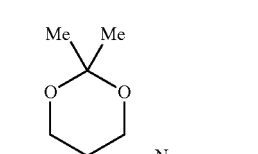 |
| 72 | 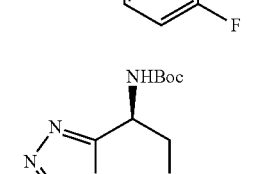 |
| 73 | 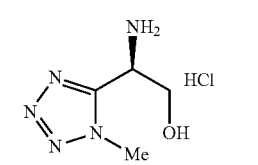 |
| 74 | |
| 75 | |
TABLE 10-continued
| PEx | Str |
|---|---|
| 76 | |
TABLE 11
| PEx | Str |
|---|---|
| 77 | |
| 78 | |
| 79 | |
| 80 | |
| 81 | |
| 82 | |

TABLE 11-continued
| PEx | Str |
|---|---|
| 83 | 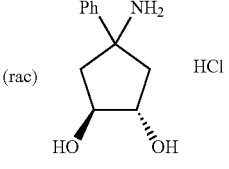 [SMILES: NC1(c2ccccc2)C[C@H](O)[C@@H](O)C1 ; Cl] |
| 84 | 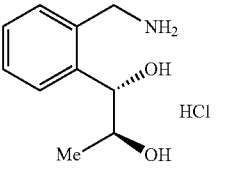 [SMILES: C[C@H](O)[C@@H](O)c1ccccc1CN ; Cl] |
| 85 | 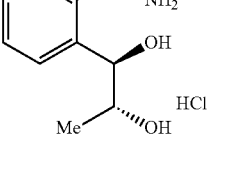 |
| 86 | 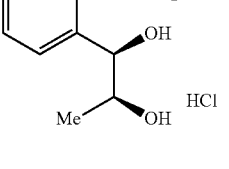 |
| 87 | 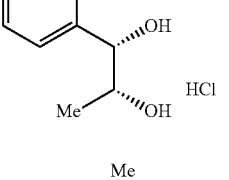 |
| 88 | 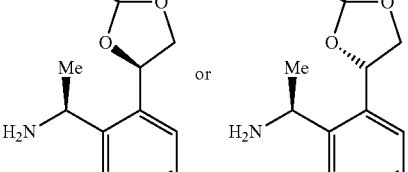 |
TABLE 12
| PEx | Str |
|---|---|
| 89 | 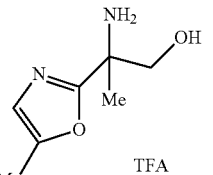 |
| 90 | 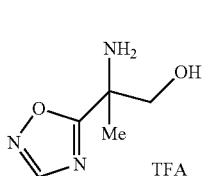 |
| 91 | 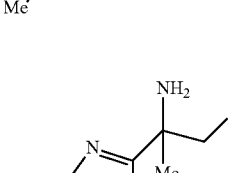 |
| 92 | 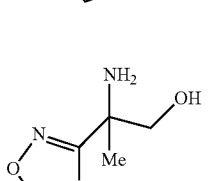 |
| 93 | 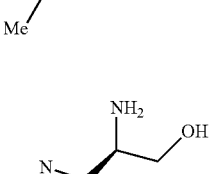 |
| 94 | 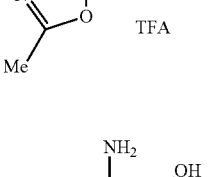 |
| 95 | 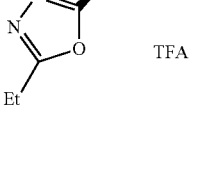 |
| 96 | 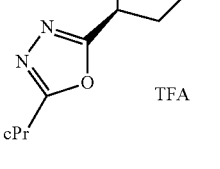 |

TABLE 12-continued
| PEx | Str |
|---|---|
| 97 | 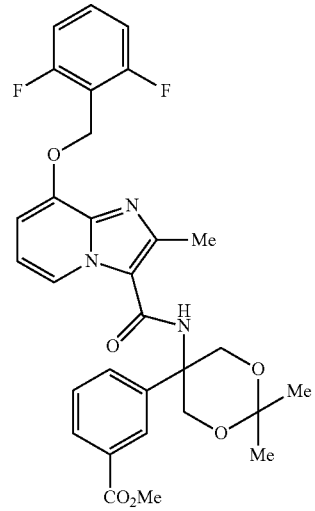 [SMILES: COC(=O)c1cccc(C2(NC(=O)c3c(C)nc4c(OCc5c(F)cccc5F)cccn34)COC(C)(C)OC2)c1] |
| 98 | 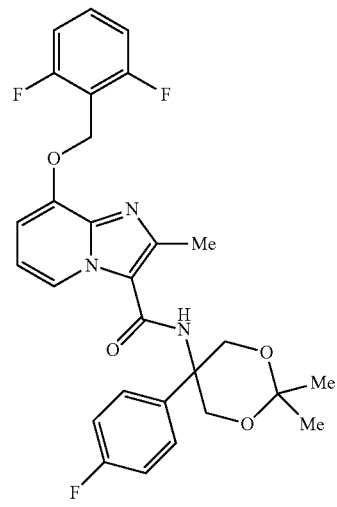 [SMILES: Cc1nc2c(OCc3c(F)cccc3F)cccn2c1C(=O)NC1(c2ccc(F)cc2)COC(C)(C)OC1] |
TABLE 13
| PEx | Str |
|---|---|
| 99 | 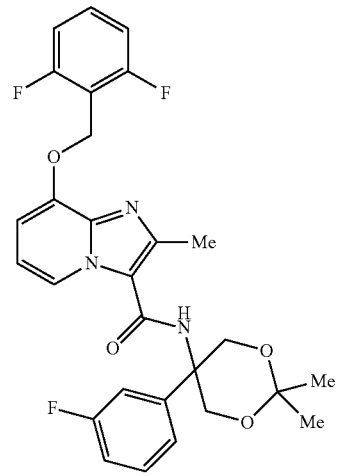 [SMILES: Cc1nc2c(OCc3c(F)cccc3F)cccn2c1C(=O)NC1(c2cccc(F)c2)COC(C)(C)OC1] |
TABLE 13-continued
| PEx | Str |
|---|---|
| 100 | 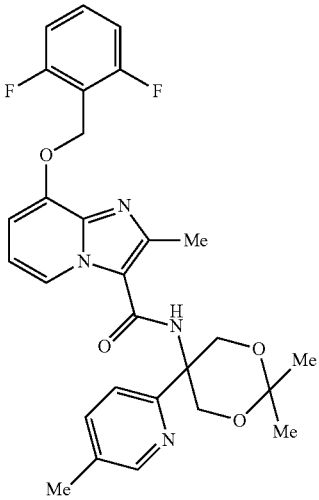 [SMILES: Cc1ccc(C2(NC(=O)c3c(C)nc4c(OCc5c(F)cccc5F)cccn34)COC(C)(C)OC2)nc1] |
| 101 | 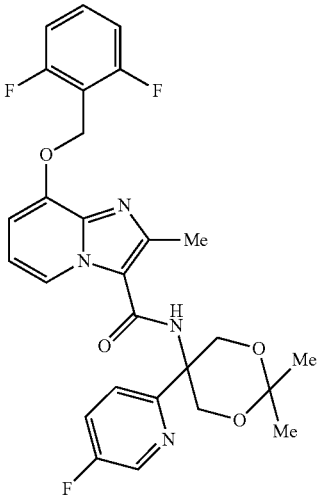 [SMILES: Cc1nc2c(OCc3c(F)cccc3F)cccn2c1C(=O)NC1(c2ccc(F)cn2)COC(C)(C)OC1] |
| 102 | 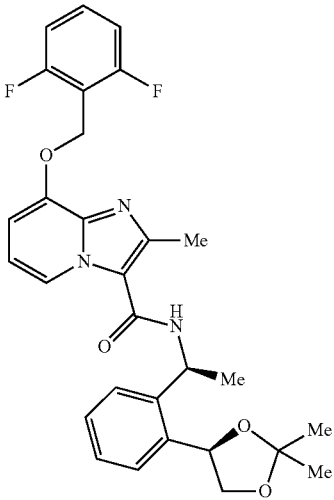 [SMILES: Cc1nc2c(OCc3c(F)cccc3F)cccn2c1C(=O)N[C@@H](C)c1ccccc1[C@H]1COC(C)(C)O1] |
or TABLE 13-continued
| PEx | Str |
|---|---|
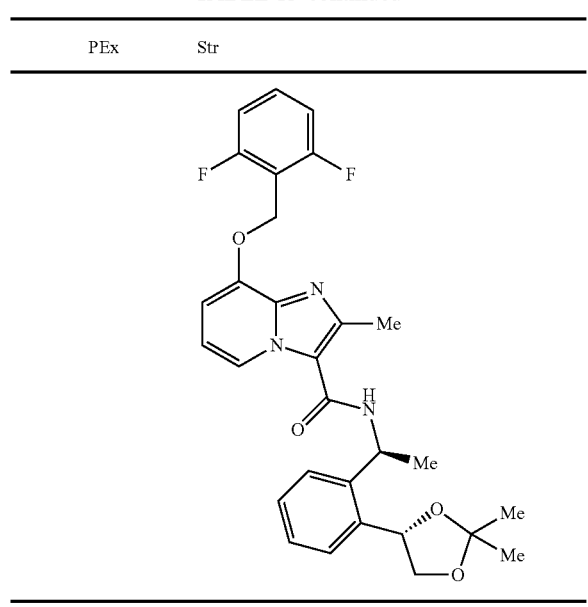
TABLE 14
| PEx | Str |
|---|---|
| 103 | |
| 104 | |
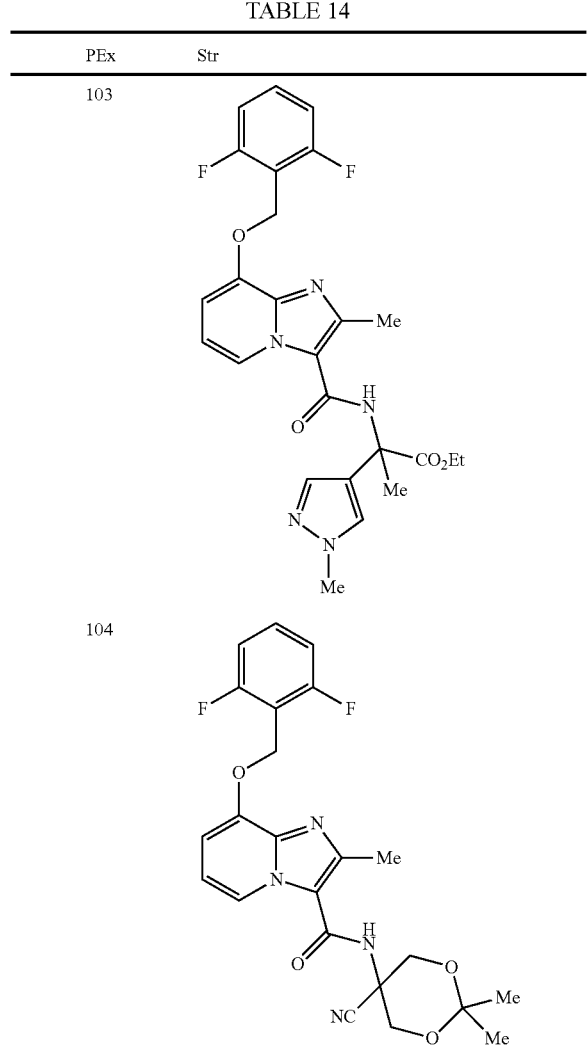
TABLE 14-continued
| PEx | Str |
|---|---|
| 105 | |
| 106 | |
| 107 | |
| 108a | |
| 108b | |
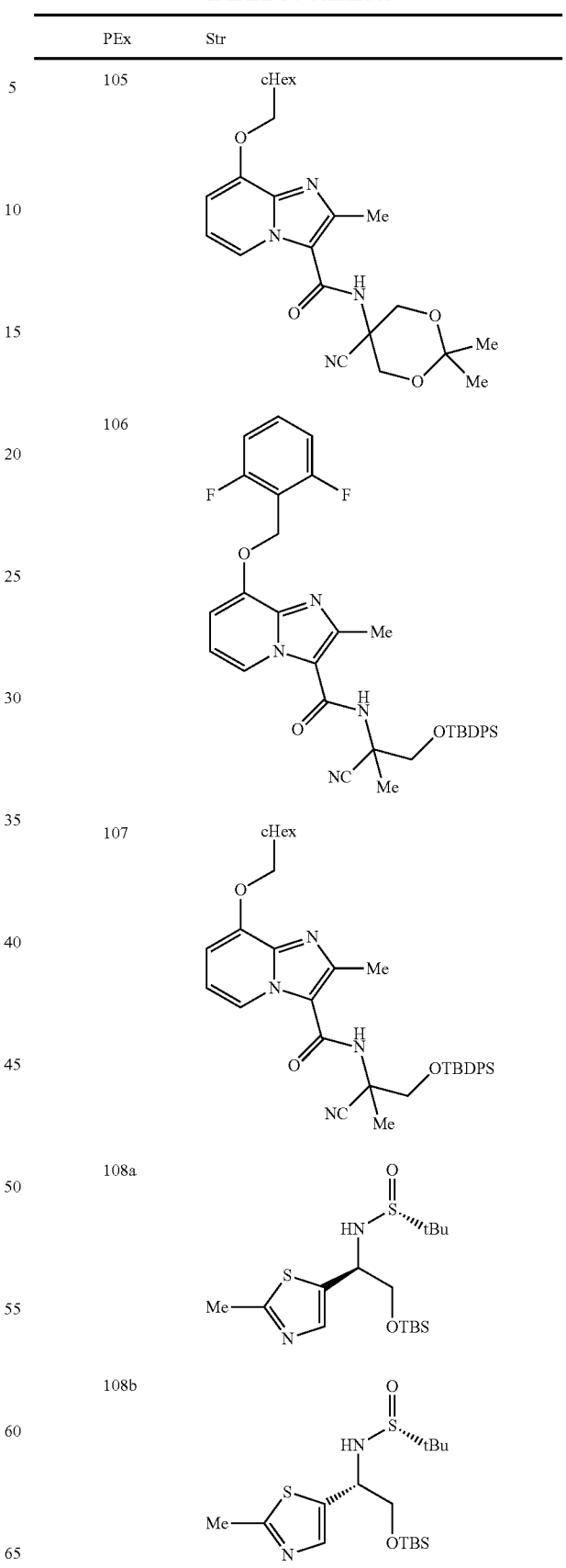

TABLE 14-continued

| PEx | Str |
|---|---|
| 109 | (structure) |

TABLE 15

| PEx | Str |
|---|---|
| 110 | (structure) |
| 111 | (structure) |
| 112a | (structure) |
| 112b | (structure) |
| 113a | (structure) |

TABLE 15-continued

| PEx | Str |
|---|---|
| 113b | (structure) |
| 114 | (structure) |
| 115 | (structure) or (structure) |
| 116 | (structure) |
| 117 | (structure) |

TABLE 16

| PEx | Str |
|---|---|
| 118 | (structure) |
| 119 | (structure) |
| 120 | (structure) |
| 121 | (structure) |
| 122 | (structure) |
| 123 | (structure) |
| 124 | (structure) |

TABLE 16-continued

| PEx | Str |
|---|---|
| 125 | (structure) |
| 126 | (structure) |
| 127 | (structure) |

TABLE 17

| PEx | Str |
|---|---|
| 128 | (structure) |
| 129 | (structure) |
| 130 | (structure) |

TABLE 17-continued

| PEx | Str |
|---|---|
| 131 | (structure) |
| 132 | (rac) (structure) |
| 133 | (structure) or (structure) |
| 134 | (structure) |
| 135 | (structure) |
| 136 | (structure) |
| 137 | (structure) |

TABLE 18

| PEx | Str |
|---|---|
| 138 | (structure) |
| 139 | (structure) |
| 140 | (structure) |
| 141 | (structure) |
| 142 | (structure) |
| 143 | (structure) |
| 144 | (structure) |

TABLE 18-continued
| PEx | Str |
|---|---|
| 145 | 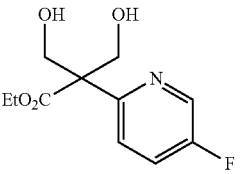 [SMILES: CCOC(=O)C(CO)(CO)c1ccc(F)cn1] |
| 146 | 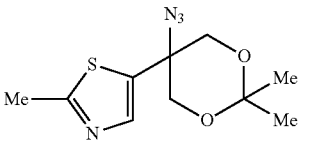 [SMILES: Cc1ncc(C2(N=[N+]=[N-])COC(C)(C)OC2)s1] |
| 147 | 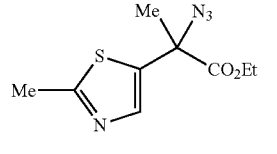 [SMILES: CCOC(=O)C(C)(N=[N+]=[N-])c1cnc(C)s1] |
| 148 | 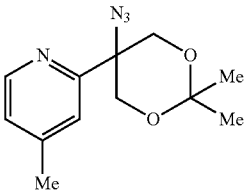 [SMILES: Cc1ccnc(C2(N=[N+]=[N-])COC(C)(C)OC2)c1] |
| 149 | 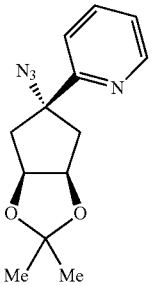 [SMILES: CC1(C)O[C@H]2C[C@@](N=[N+]=[N-])(c3ccccn3)C[C@H]2O1] |
TABLE 19
| PEx | Str |
|---|---|
| 150 | 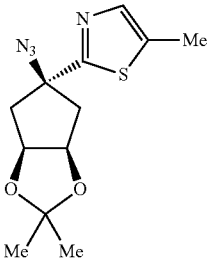 or 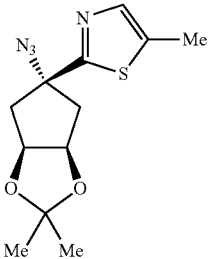 |
| 151 | 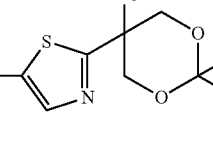 |
| 152 | 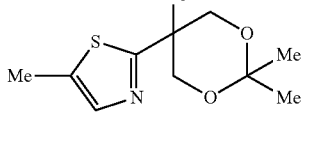 |
| 153 | 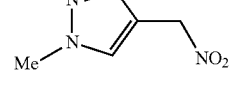 |
| 154 | (rac) |
| 155 | (rac) |
| 156 | (rac) 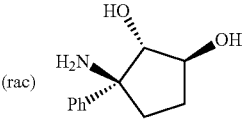 [SMILES: N[C@]1(c2ccccc2)CC[C@H](O)[C@H]1O] |

TABLE 19-continued

| PEx | Str |
|---|---|
| 157 | (structure: N-[(1S)-1-(2-{(1R)-1,2-dihydroxyethyl}phenyl)ethyl]-2,2,2-trifluoroacetamide) or (diastereomer of the above) |

TABLE 20

| PEx | Str |
|---|---|
| 158 | (2-{NHBoc-methyl}phenyl with CH(OH)-CH(OH)Me side chain) |
| 159 | (2-{NHBoc-methyl}phenyl with CH(OH)-CH(OH)Me side chain, different stereochemistry) |
| 160 | (2-{NHBoc-methyl}phenyl with CH(OH)-CH(OH)Me side chain, different stereochemistry) |
| 161 | (2,6-difluorobenzyloxy-imidazo[1,2-a]pyridine-2-methyl-3-carboxamide linked to 2,2-dimethyl-1,3-dioxane bearing tetrazole) |

TABLE 20-continued

| PEx | Str |
|---|---|
| 162 | (8-(cyclohexylmethoxy)-2-methylimidazo[1,2-a]pyridine-3-carboxamide linked to 2,2-dimethyl-1,3-dioxane bearing tetrazole) |
| 163 | (8-(cyclohexylmethoxy)-2-methylimidazo[1,2-a]pyridine-3-carboxamide linked to 2-methyl-1-hydroxy-2-(tetrazol-5-yl)propyl) |
| 164 | (N-Boc-2,2-dimethyl-4-methyl-oxazolidine with 5-methyloxazole) |
| 165 | (N-Boc-2,2-dimethyloxazolidine with 5-methyl-1,3,4-oxadiazole) |

TABLE 21

| PEx | Str |
|---|---|
| 166 | (structure) |
| 167 | (structure) |
| 168 | (structure) |
| 169 | (structure) |
| 170 | (structure) |
| 171 | (structure) |

TABLE 21-continued

| PEx | Str |
|---|---|
| 172 | (structure) |
| 173 | (structure) |
| 174 | (structure) or (structure) |
| 175 | (structure) |

TABLE 22

| PEx | Str |
|---|---|
| 176 | (structure) |

TABLE 22-continued
| PEx | Str |
|---|---|
| 177 | 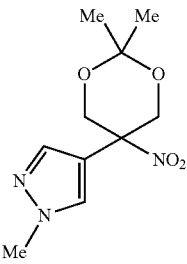 [SMILES: Cn1cc(C2([N+](=O)[O-])COC(C)(C)OC2)cn1] |
| 178 | 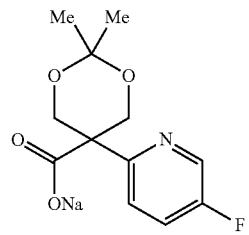 |
| 179 | 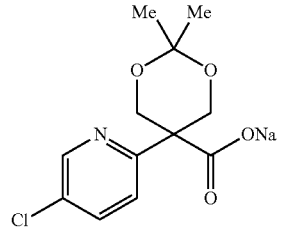 |
| 180 | 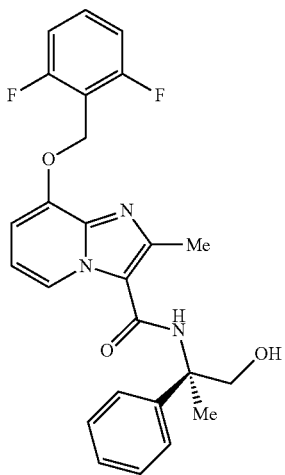 |
TABLE 22-continued
| PEx | Str |
|---|---|
| 181 | 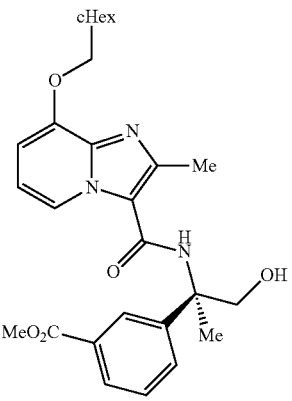 |
TABLE 23
| PEx | Str |
|---|---|
| 182 | 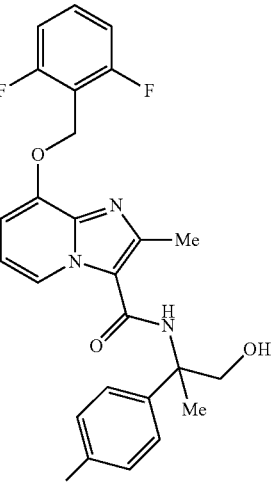 |
| 183 | 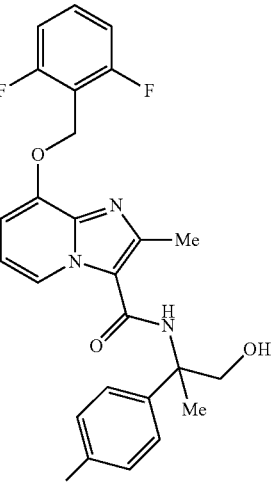 |

TABLE 23-continued
| PEx | Str |
|---|---|
| 184 | 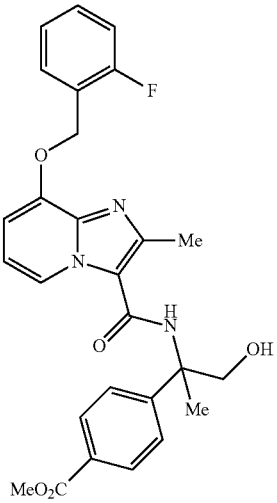 [SMILES: COC(=O)c1ccc(C(C)(CO)NC(=O)c2c(C)nc3c(OCc4ccccc4F)cccn23)cc1] |
| 185 | |
| 186 | |
TABLE 23-continued
| PEx | Str |
|---|---|
| 187 | 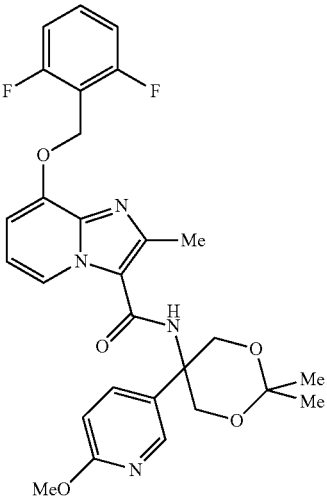 [SMILES: COc1ccc(C2(NC(=O)c3c(C)nc4c(OCc5c(F)cccc5F)cccn34)COC(C)(C)OC2)cn1] |
TABLE 24
| PEx | Str |
|---|---|
| 188 | |
| 189 | |

TABLE 24-continued
| PEx | Str |
|---|---|
| 190 | 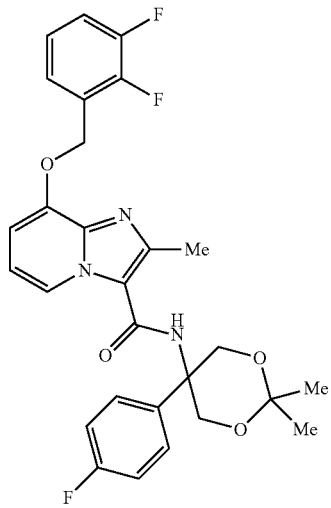 [SMILES: Cc1nc2c(OCc3cccc(F)c3F)cccn2c1C(=O)NC1(c2ccc(F)cc2)COC(C)(C)OC1] |
| 191 | 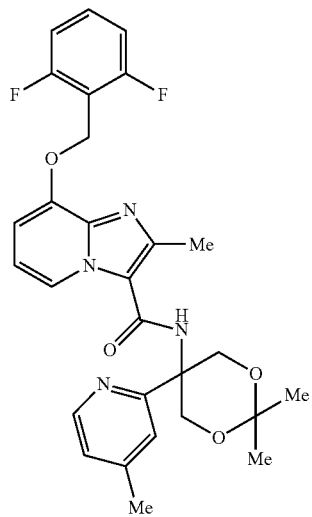 [SMILES: Cc1ccnc(C2(NC(=O)c3c(C)nc4c(OCc5c(F)cccc5F)cccn34)COC(C)(C)OC2)c1] |
| 192 | 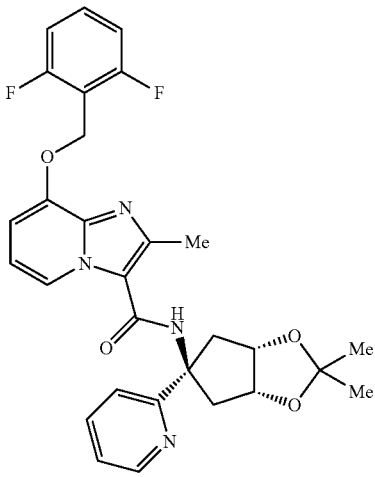 [SMILES: Cc1nc2c(OCc3c(F)cccc3F)cccn2c1C(=O)N[C@@]1(c2ccccn2)C[C@@H]2OC(C)(C)O[C@@H]2C1] |
TABLE 24-continued
| PEx | Str |
|---|---|
| 193 | 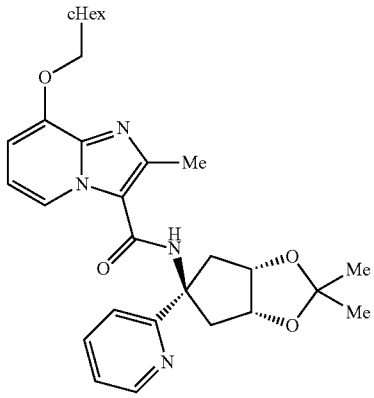 |
TABLE 25
| PEx | Str |
|---|---|
| 194 | 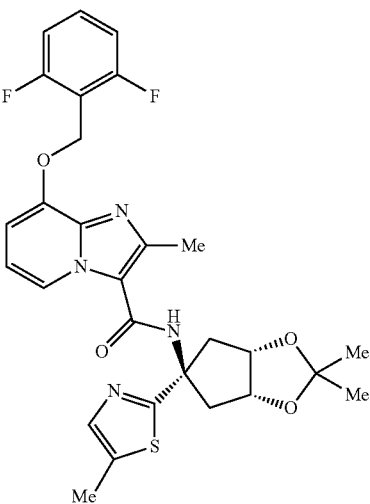
or
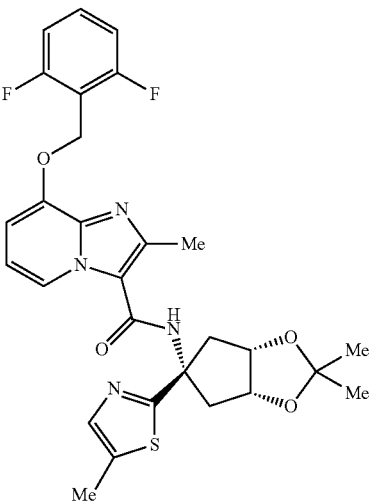 [SMILES: Cc1cnc([C@@]2(NC(=O)c3c(C)nc4c(OCc5c(F)cccc5F)cccn34)C[C@@H]3OC(C)(C)O[C@@H]3C2)s1] |

US 9,278,968 B2
TABLE 25-continued
| PEx | Str |
|---|---|
| 195 | 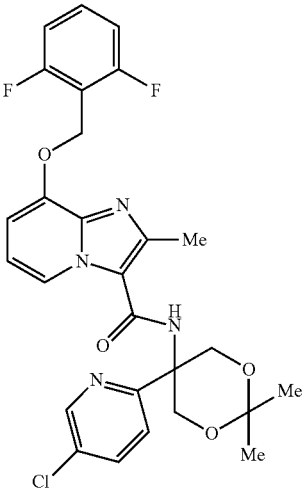 [SMILES: Cc1nc2c(OCc3c(F)cccc3F)cccn2c1C(=O)NC1(c2ccc(Cl)cn2)COC(C)(C)OC1] |
| 196 | 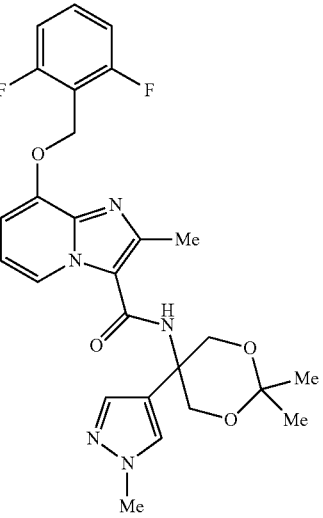 |
| 197 | 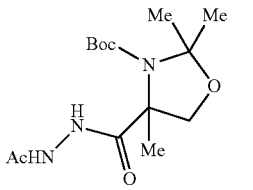 [SMILES: CC(=O)NNC(=O)C1(C)COC(C)(C)N1C(=O)OC(C)(C)C] |
TABLE 26
| PEx | Str |
|---|---|
| 198 | 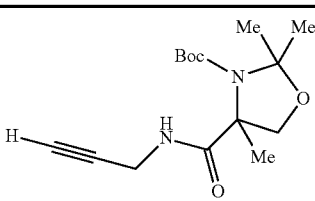 |
TABLE 26-continued
| PEx | Str |
|---|---|
| 199 | 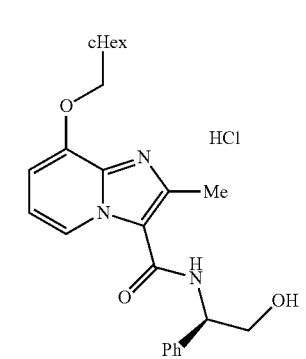 |
| 200 | 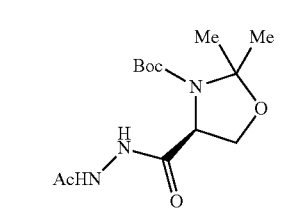 [SMILES: CC(=O)NNC(=O)[C@@H]1COC(C)(C)N1C(=O)OC(C)(C)C] |
| 201 | 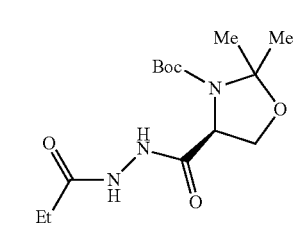 [SMILES: CCC(=O)NNC(=O)[C@@H]1COC(C)(C)N1C(=O)OC(C)(C)C] |
| 202 | 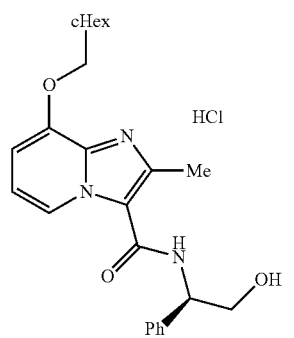 |
| 203 | 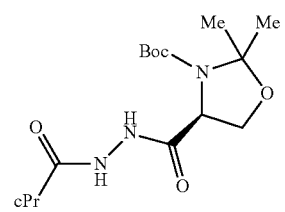 |

TABLE 26-continued
| PEx | Str |
|---|---|
| 204 | 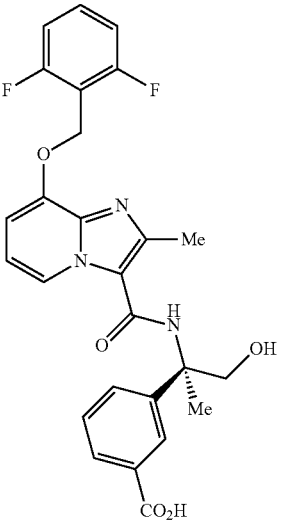 [SMILES: Cc1nc2c(OCc3c(F)cccc3F)cccn2c1C(=O)N[C@@](C)(CO)c1cccc(C(=O)O)c1] |
| 205 | 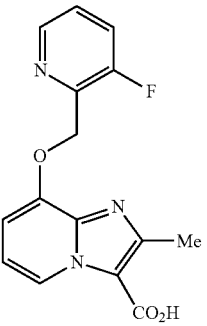 [SMILES: Cc1nc2c(OCc3ncccc3F)cccn2c1C(=O)O] |
| 206 | 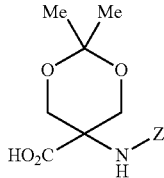 |
| 207 | 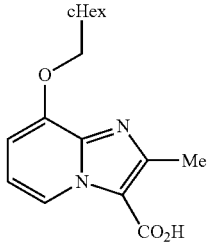 |
TABLE 27
| PEx | Str |
|---|---|
| 208a | 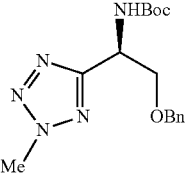 |
| 208b | 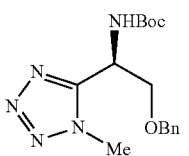 [SMILES: Cn1nnnc1[C@H](COCc1ccccc1)NC(=O)OC(C)(C)C] |
| 209a | 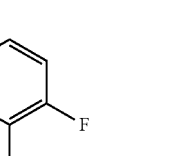 |
| 209b | 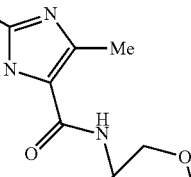 |

TABLE 27-continued
| PEx | Str |
|---|---|
| 210a | 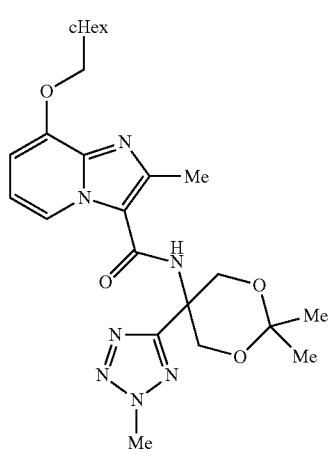 |
| 210b | 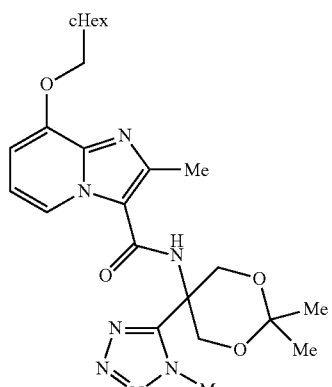 |
TABLE 28
| PEx | Str |
|---|---|
| 211 | 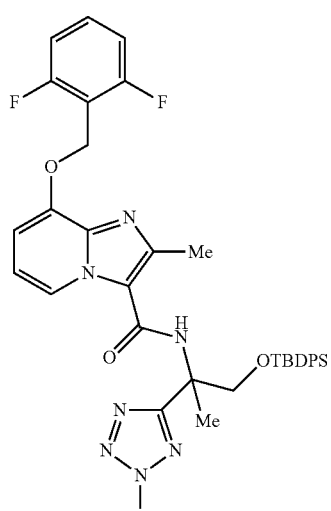 |
| 212 | 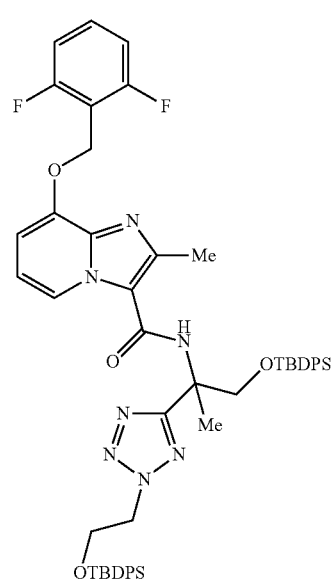 |
| 213 | 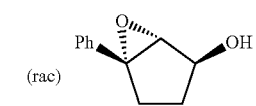 |
| 214 | 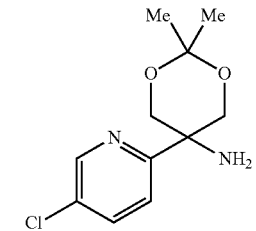 [SMILES: CC1(C)OCC(N)(c2ccc(Cl)cn2)CO1] |
| 215 | 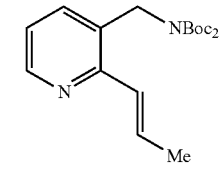 |
| 216 | 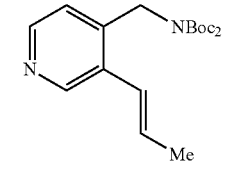 |
| 217 | 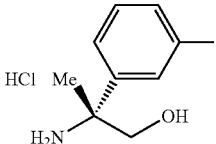 |

TABLE 28-continued

| PEx | Str |
|---|---|
| 218 | 2-ethyl-2H-tetrazol-5-yl CH(NHBoc)CH2OH |

TABLE 29

| PEx | Str |
|---|---|
| 219 | 2-isopropyl-2H-tetrazol-5-yl CH(NHBoc)CH2OH |
| 220 | 2-(difluoromethyl)-2H-tetrazol-5-yl CH(NHBoc)CH2OH |
| 221 | 2-ethyl-2H-tetrazol-5-yl CH(NH2)CH2OH · HCl |
| 222 | 2-(difluoromethyl)-2H-tetrazol-5-yl CH(NH2)CH2OH · HCl |
| 223 | 3-(aminomethyl)pyridin-2-yl CH(OH)CH(Me)OH (rac) · HCl |
| 224 | 4-(aminomethyl)pyridin-3-yl CH(OH)CH(Me)OH (rac) · HCl |
| 225 | methyl 3-(2-amino-propan-2-yl)benzoate · HCl |
| 226 | 2-(2-methyl-2H-tetrazol-5-yl)-1-aminopropan-2-yl methanol · TFA |
| 227 | 2-(5-ethyl-1,3,4-oxadiazol-2-yl)-1-aminopropan-2-yl methanol · TFA |
| 228 | 2-(5-cyclopropyl-1,3,4-oxadiazol-2-yl)-1-aminopropan-2-yl methanol · TFA |
| 229 | 2-(5-trifluoromethyl-1,3,4-oxadiazol-2-yl)-1-aminopropan-2-yl methanol · TFA |
| 230 | 8-(2-cyclohexylethoxy)-2-methyl-N-[2,2-dimethyl-5-(5-methyl-1,3,4-oxadiazol-2-yl)-1,3-dioxan-5-yl]imidazo[1,2-a]pyridine-3-carboxamide |

TABLE 30
| PEx | Str |
|---|---|
| 231 | 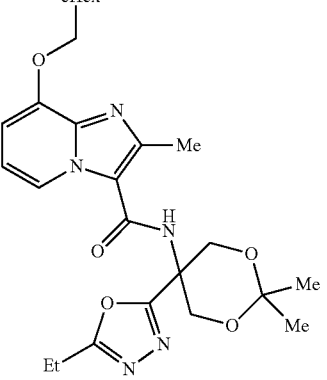 |
| 232 | 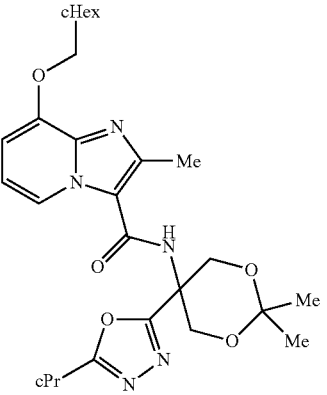 |
| 233 | 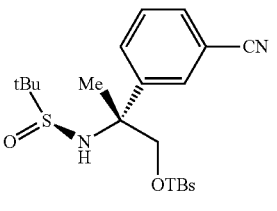 |
| 234 | 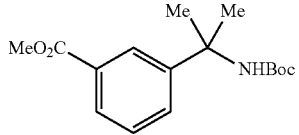 [SMILES: COC(=O)c1cccc(C(C)(C)NC(=O)OC(C)(C)C)c1] |
| 235 | 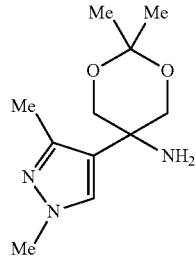 [SMILES: Cc1nn(C)cc1C1(N)COC(C)(C)OC1] |//
TABLE 30-continued
| PEx | Str |
|---|---|
| 236 | 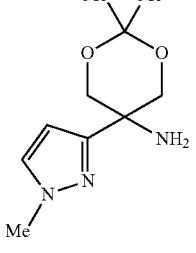 |
| 237 | 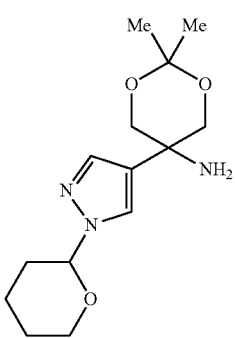 [SMILES: CC1(C)OCC(N)(c2cnn(C3CCCCO3)c2)CO1] |
| 238 | 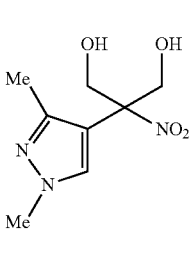 [SMILES: Cc1nn(C)cc1C(CO)(CO)[N+](=O)[O-]] |
| 239 | 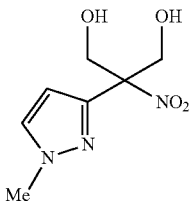 [SMILES: Cn1ccc(C(CO)(CO)[N+](=O)[O-])n1] |
| 240 | 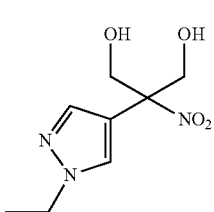 |

TABLE 31
| PEx | Str |
|---|---|
| 241 | 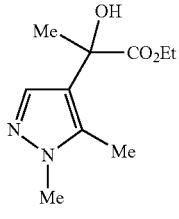 and 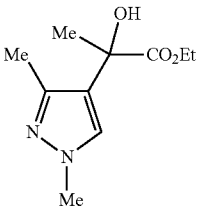 |
| 242 | 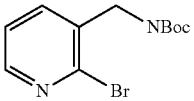 |
| 243 | 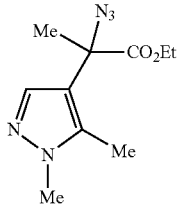 and 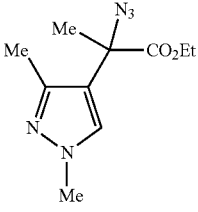 |
| 244 | 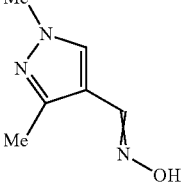 |
| 245 | 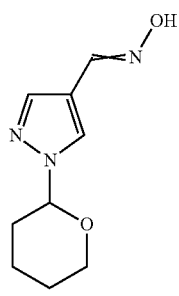 |
TABLE 31-continued
| PEx | Str |
|---|---|
| 246 | 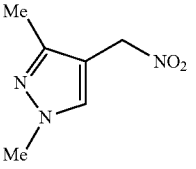 |
| 247 | 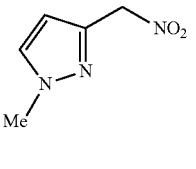 |
| 248 | 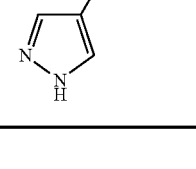 |
TABLE 32
| PEx | Str |
|---|---|
| 249 | (rac) 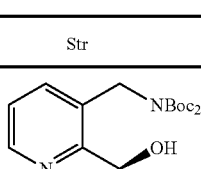 |
| 250 | (rac) 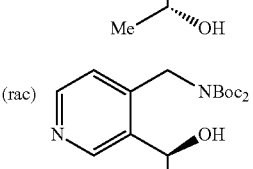 |
| 251 | 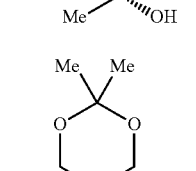 |
| 252 | 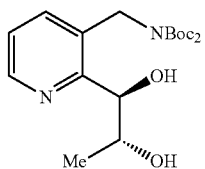 |

TABLE 32-continued
| PEx | Str |
|---|---|
| 253 | 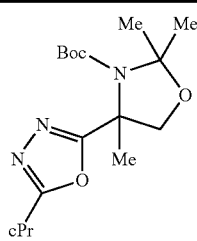 |
| 254 | 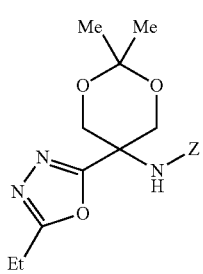 |
| 255 | 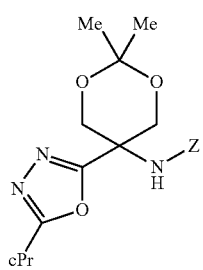 |
| 256 | 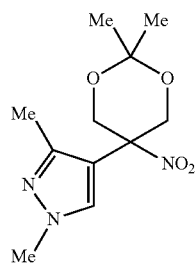 |
| 257 | 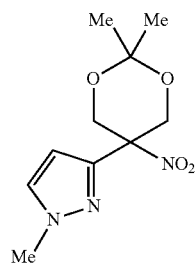 |
TABLE 32-continued
| PEx | Str |
|---|---|
| 258 | 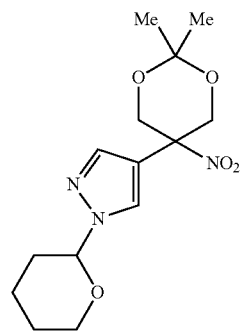 |
| 259 | 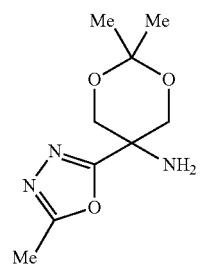 |
| 260 | 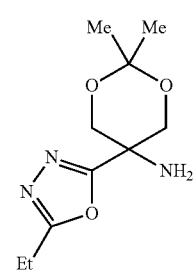 [SMILES: CCc1nnc(C2(N)COC(C)(C)OC2)o1] |
TABLE 33
| PEx | Str |
|---|---|
| 261 | 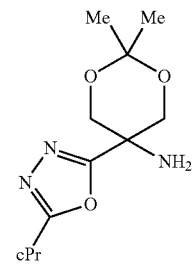 |

TABLE 33-continued
| PEx | Str |
|---|---|
| 262 | 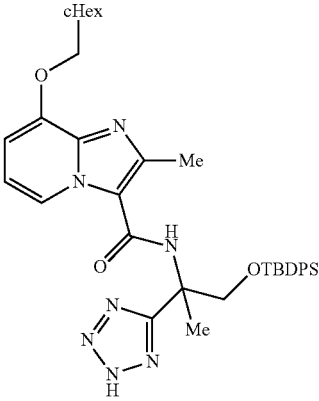 |
| 263 | 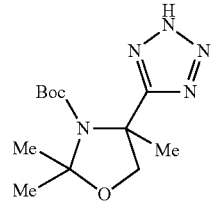 [SMILES: CC(C)(C)OC(=O)N1C(C)(C)OCC1(C)c1nn[nH]n1] |
| 264 | 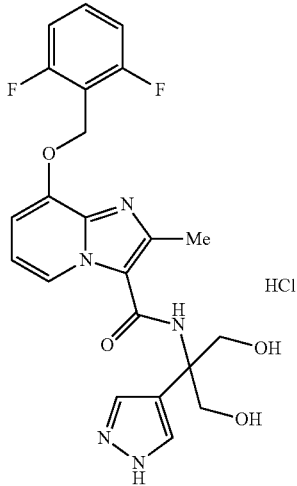 [SMILES: Cc1nc2c(OCc3c(F)cccc3F)cccn2c1C(=O)NC(CO)(CO)c1cn[nH]c1 ; Cl] |
| 265 | 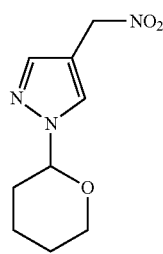 [SMILES: O=[N+]([O-])Cc1cnn(C2CCCCO2)c1] |
| 266 | 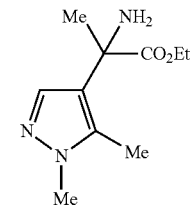 and 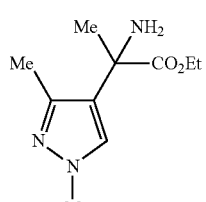 |
| 267 | 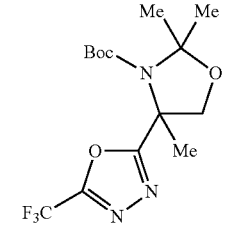 |
| 268 | 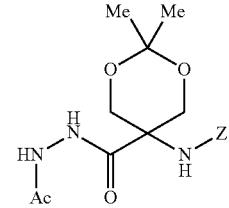 |
TABLE 34
| PEx | Str |
|---|---|
| 269 | 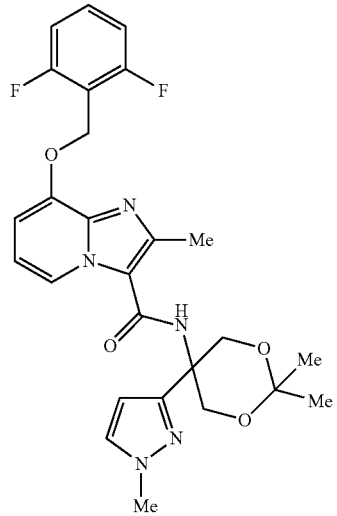 [SMILES: Cc1nc2c(OCc3c(F)cccc3F)cccn2c1C(=O)NC1(c2ccn(C)n2)COC(C)(C)OC1] |

TABLE 34-continued
| PEx | Str |
|---|---|
| 270 | 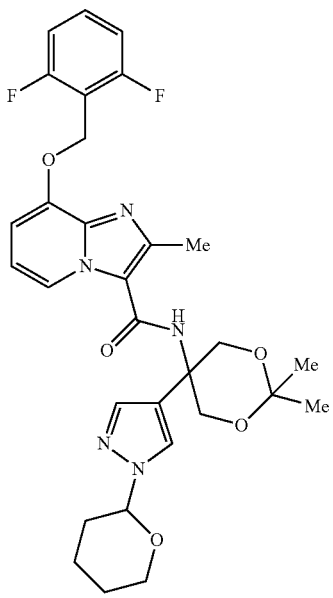 [SMILES: Cc1nc2c(OCc3c(F)cccc3F)cccn2c1C(=O)NC1(c2cnn(C3CCCCO3)c2)COC(C)(C)OC1] |
| 271 | 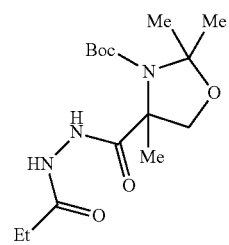 [SMILES: CCC(=O)NNC(=O)C1(C)COC(C)(C)N1C(=O)OC(C)(C)C] |
| 272 | 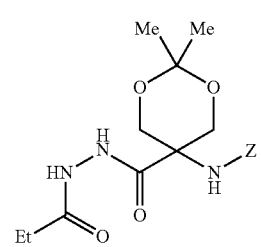 |
| 273 | 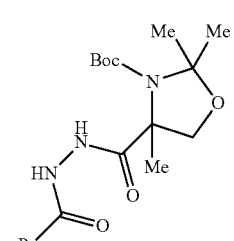 |
| 274 | 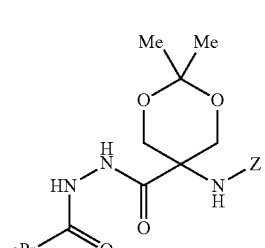 |
TABLE 35
| PEx | Str |
|---|---|
| 275 | 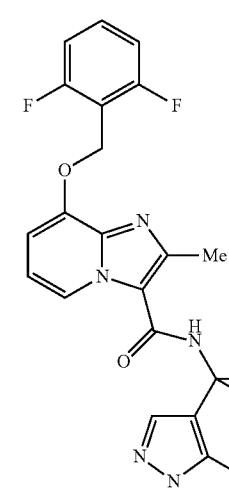 |
| 276 | 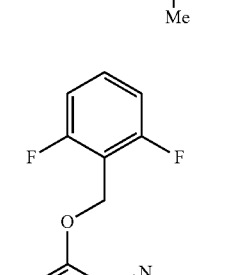 |
| 277 | 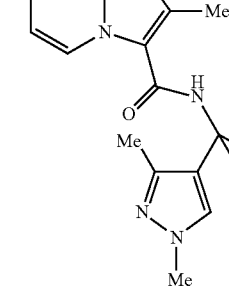 |

TABLE 35-continued
| PEx | Str |
|---|---|
| 278 | 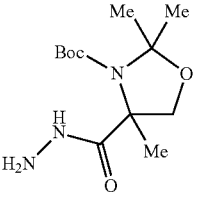 |
| 279 | 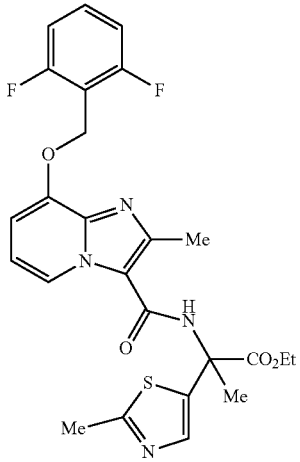 [SMILES: CCOC(=O)C(C)(NC(=O)c1c(C)nc2c(OCc3c(F)cccc3F)cccn12)c1cnc(C)s1] |
| 280 | 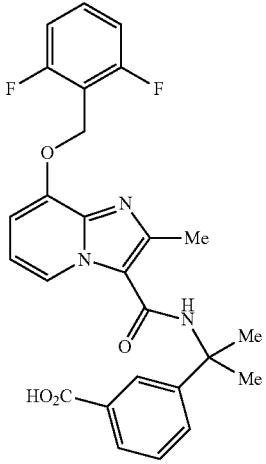 [SMILES: Cc1nc2c(OCc3c(F)cccc3F)cccn2c1C(=O)NC(C)(C)c1cccc(C(=O)O)c1] |
TABLE 36
| PEx | Str |
|---|---|
| 281a | 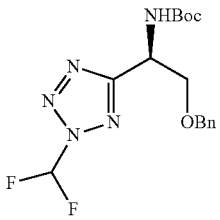 |
TABLE 36-continued
| PEx | Str |
|---|---|
| 281b | 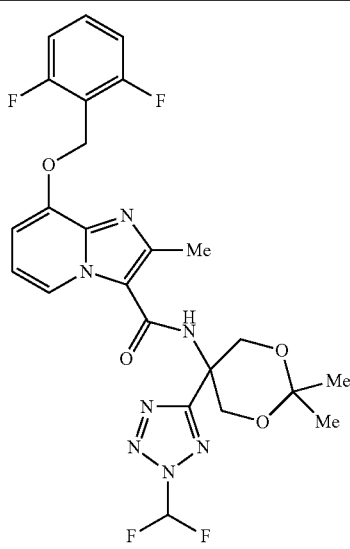 |
| 282 | 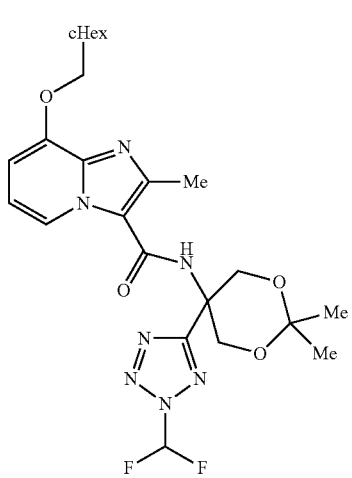 |
| 283 | 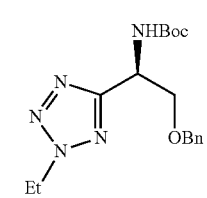 [SMILES: CCn1nnc([C@H](COCc2ccccc2)NC(=O)OC(C)(C)C)n1] |
| 284 | 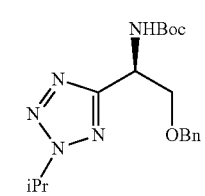 [SMILES: CC(C)n1nnc([C@H](COCc2ccccc2)NC(=O)OC(C)(C)C)n1] |

TABLE 36-continued
| PEx | Str |
|---|---|
| 285 | 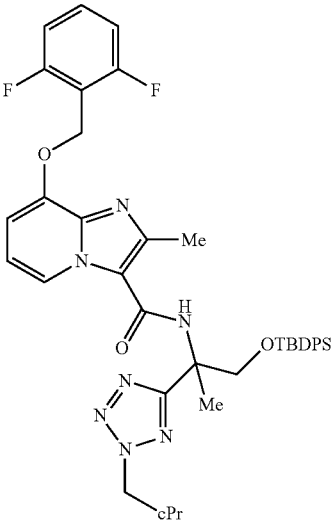 |
| 286 | 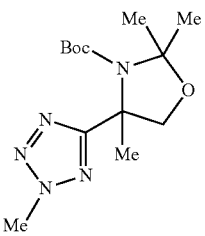 |
| 287 | 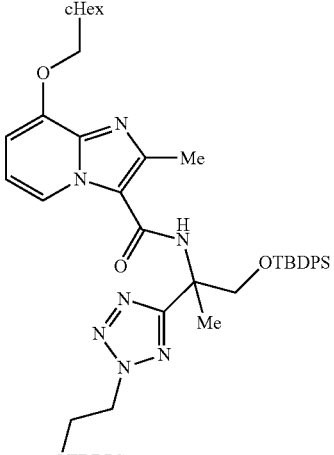 |
TABLE 37
| PEx | Str |
|---|---|
| 288 | 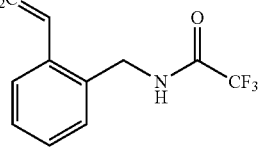 |
TABLE 37-continued
| PEx | Str |
|---|---|
| 289 | 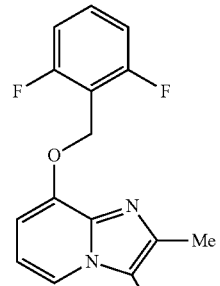 |
| 290 | 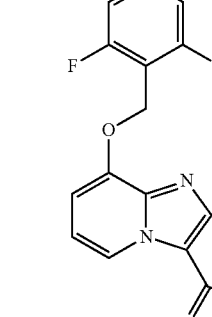 (rac) |
| 291 | 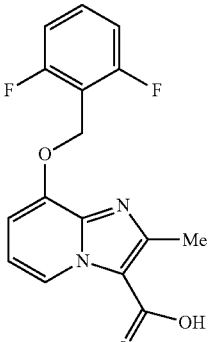 |
| 292 | 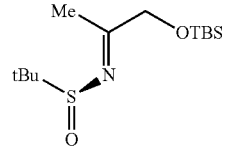 |

TABLE 37-continued
| PEx | Str |
|---|---|
| 293 | 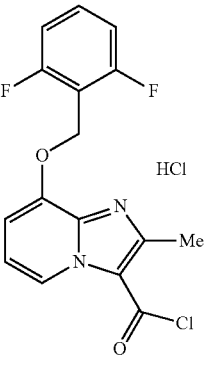 [SMILES: Cc1nc2c(OCc3c(F)cccc3F)cccn2c1C(=O)Cl ; Cl] |
| 294 | 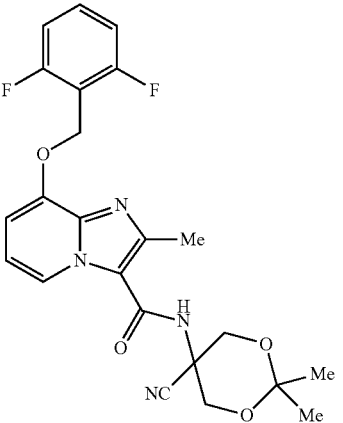 [SMILES: Cc1nc2c(OCc3c(F)cccc3F)cccn2c1C(=O)NC1(C#N)COC(C)(C)OC1] |
| 295 | 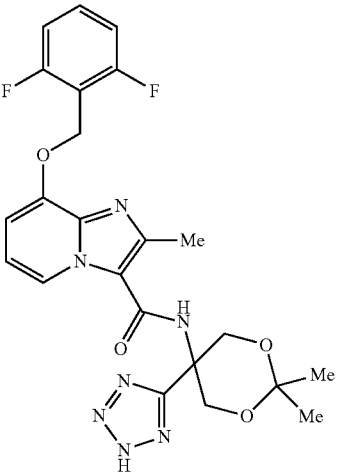 [SMILES: Cc1nc2c(OCc3c(F)cccc3F)cccn2c1C(=O)NC1(c2nn[nH]n2)COC(C)(C)OC1] |
TABLE 38
| PEx | Str |
|---|---|
| 296 | 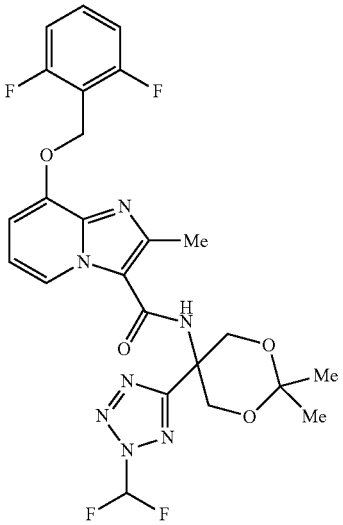 [SMILES: Cc1nc2c(OCc3c(F)cccc3F)cccn2c1C(=O)NC1(c2nnn(C(F)F)n2)COC(C)(C)OC1] |
| 297 | 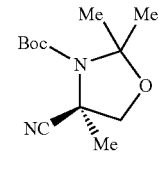 |
| 298 | 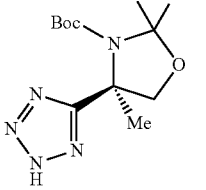 |
| 299 | 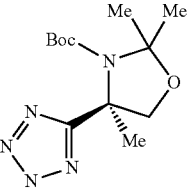 |
| 300 | 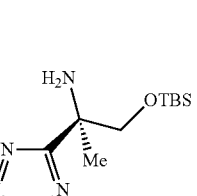 |

TABLE 38-continued
| PEx | Str |
|---|---|
| 301 | 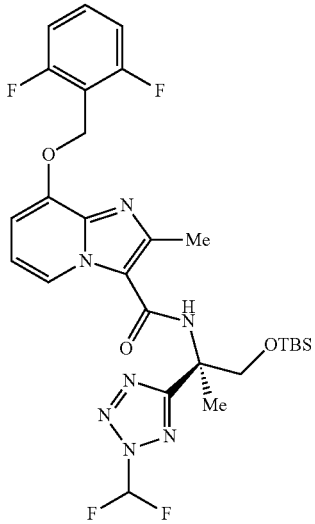 [SMILES: Cc1nc2c(OCc3c(F)cccc3F)cccn2c1C(=O)N[C@@](C)(CO[Si](C)(C)C(C)(C)C)c1nnn(C(F)F)n1] |
| 302 | 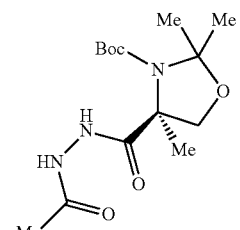 |
| 303 | 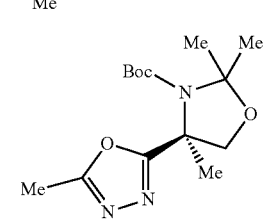 |
TABLE 39
| PEx | Str |
|---|---|
| 304 | 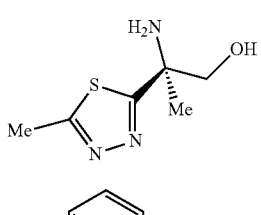 |
| 305 | 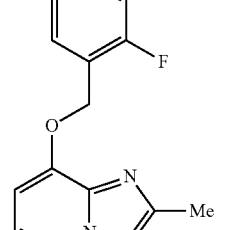 |
| 306 | 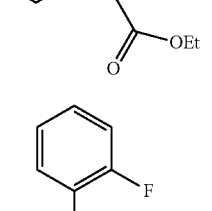 |
TABLE 39-continued
| PEx | Str |
|---|---|
| 307 | 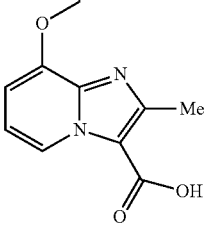 |
| 308 | 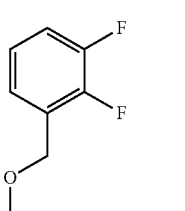 |
| 309 | 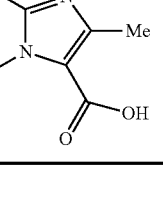 |
| 310 | 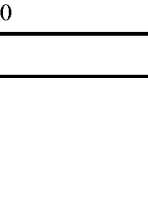 |
TABLE 40
| PEx | PSyn | DATA |
|---|---|---|
| 1 | PEx 1 | ESI+: 347 |
| 2 | PEx 2 | ESI+: 317 |
| 3 | PEx 3 | ESI+: 330 |
| 4 | PEx 4 | ESI+: 348 |
| 5 | PEx 5 | ESI+: 270 [M + Na]+ |
| 6 | PEx 6 | ESI−: 208 |
| 7 | PEx 7 | ESI+: 184 |
| 8 | PEx 8 | ESI+: 159 |
| 9 | PEx 9 | ESI−: 318 |

TABLE 40-continued

| PEx | PSyn | DATA |
|---|---|---|
| 10 | PEx 10 | ESI+: 266 [M + Na]+ |
| 11 | PEx 11 | ESI+: 144 |
| 12 | PEx 12 | APCI/ESI+: 208 |
| 13 | PEx 13 | ESI+: 287 |
| 14 | PEx 14 | ESI+: 158 |
| 15 | PEx 15 | ESI+: 496 |
| 16 | PEx 16 | ESI+: 508 |
| 17a | PEx 17 | ESI+: 377<br>NMR (CDCl3): −0.03 (3H, s), 0.05 (3H, s), 0.85 (9H, s), 1.28 (9H, s), 2.43 (3H, d, J = 1.1 Hz), 4.04 (1H, dd, J = 4.9, 9.8 Hz), 4.05 (1H, dd, J = 4.3, 9.8 Hz), 4.57 (1H, d, J = 5.5 Hz), 4.76 (1H, ddd, J = 4.3, 4.9, 5.5 Hz), 7.38 (1H, q, J =1.1 Hz) |
| 17b | PEx 17 | ESI+: 377<br>NMR (CDCl3): −0.01 (3H, s), 0.02 (3H, s), 0.87 (9H, s), 1.24 (9H, s), 2.44 (3H, d, J = 1.2 Hz), 3.86 (1H, dd, J = 5.5, 9.8 Hz), 3.96 (1H, dd, J = 4.6, 9.8 Hz), 4.62 (1H, d, J = 6.7 Hz), 4.66-4.72 (1H, m), 7.37 (1H, q, J = 1.2 Hz) |
| 18a | PEx 18 | ESI+: 370<br>NMR (CDCl3): −0.09 (3H, s), −0.04 (3H, s), 0.83 (9H, s), 1.24 (9H, s), 1.62 (3H, s), 3.75 (1H, d, J = 9.5 Hz), 3.85 (1H, d, J = 9.5 Hz), 4.16 (1H, s), 7.22-7.26 (1H, m), 7.30-7.36 (2H, m), 7.48-7.52 (2H, m) |

TABLE 41

| PEx | PSyn | DATA |
|---|---|---|
| 18b | PEx 18 | ESI+: 370<br>NMR (CDCl3): 0.03 (3H, s), 0.05 (3H, s), 0.89 (9H, s), 1.23 (9H, s), 1.79 (3H, s), 3.51 (1H, d, J = 9.5 Hz), 3.80 (1H, d, J = 9.5 Hz), 4.25 (1H, s), 7.25-7.30 (1H, m), 7.31-7.37 (2H, m), 7.44-7.48 (2H, m) |
| 19 | PEx 19 | ESI+: 428 |
| 20 | PEx 20 | ESI+: 216 |
| 21 | PEx 21 | ESI+: 224 |
| 22 | PEx 22 | EI: 259 |
| 23 | PEx 23 | ESI+: 354 |
| 24 | PEx 24 | ESI+: 338 |
| 25 | PEx 25 | ESI+: 357 |
| 26 | PEx 26 | APCI/ESI+: 387, 389 |
| 27 | PEx 27 | ESI+: 154 |
| 28 | PEx 28 | ESI+: 226 |
| 29 | PEx 29 | ESI+: 198 |
| 30 | PEx 30 | ESI+: 266 |
| 31 | PEx 31 | ESI+: 360 |
| 32 | PEx 32 | CI+: 240 |
| 33 | PEx 33 | APCI/ESI+: 226 |
| 34 | PEx 34 | ESI+: 199 |
| 35 | PEx 35 | ESI+: 387, 389 |
| 36 | PEx 36 | ESI+: 224 |
| 37 | PEx 37 | ESI+: 196 |
| 38 | PEx 38 | ESI+: 153 |
| 39 | PEx 39 | ESI+: 169 |
| 40 | PEx 40 | ESI+: 276 |
| 41 | PEx 41 | ESI+: 294 |
| 42 | PEx 42 | ESI+: 197 |

TABLE 42

| PEx | PSyn | DATA |
|---|---|---|
| 43 | PEx 43 | NMR (DMSO-d6): 1.60-1.69 (1H, m), 2.00-2.17 (2H, m), 2.40-2.48 (1H, m), 3.93 (1H, t, J = 4.0 Hz), 4.31-4.40 (1H, m), 4.71 (1H, d, J = 4.3 Hz), 4.76 (1H, d, J = 6.6 Hz), 7.31-7.36 (1H, m), 7.37-7.46 (4H, m) |
| 44 | PEx 44 | ESI−: 262 |
| 45 | PEx 45 | ESI+: 304 [M + Na]+ |
| 46 | PEx 46 | APCI/ESI+: 373 |
| 47 | PEx 47 | ESI+: 444 |
| 48 | PEx 48 | ESI+: 347 |
| 49 | PEx 49 | ESI+: 298 |
| 50 | PEx 50 | ESI−: 302 |

TABLE 42-continued

| PEx | PSyn | DATA |
|---|---|---|
| 51 | PEx 51 | ESI+: 213 |
| 52 | PEx 52 | APCI/ESI+: 682 |
| 53 | PEx 53 | ESI+: 314 |
| 54 | PEx 54 | ESI+: 298 |
| 55 | PEx 55 | APCI/ESI+: 722 |
| 56 | PEx 56 | ESI+: 313 |
| 57 | PEx 57 | ESI+: 298 |
| 58 | PEx 58 | ESI+: 296, 298 |
| 59 | PEx 59 | ESI+: 252 |
| 60 | PEx 60 | ESI+: 229 |
| 61 | PEx 2 | ESI+: 347 |
| 62 | Ex 3 | ESI+: 319 |
| 63 | PEx 4 | ESI+: 346 |
| 64 | PEx 289 | ESI+: 244 |
| 65 | PEx 6 | CI+: 228 |
| 66 | PEx 7 | ESI+: 196 |
| 67 | PEx 7 | ESI+: 196 |
| 68 | PEx 8 | ESI+: 152 |
| 69 | PEx 8 | ESI+: 152 |
| 70 | PEx 8 | ESI+: 153 |
| 71 | PEx 8 | ESI+: 210 |

TABLE 43

| PEx | PSyn | DATA |
|---|---|---|
| 72 | PEx 8 | ESI+: 182 |
| 73 | PEx 8 | ESI+: 159 |
| 74 | PEx 8 | ESI+: 159 |
| 75 | PEx 8 | ESI+: 189 |
| 76 | PEx 8 | ESI+: 189 |
| 77 | PEx 8 | ESI+: 189 |
| 78 | PEx 8 | ESI+: 189 |
| 79 | PEx 10 | ESI+: 223 |
| 80 | PEx 10 | ESI+: 227 |
| 81 | PEx 10 | ESI+: 244 |
| 82 | PEx 11 | ESI+: 144 |
| 83 | PEx 11 | ESI+: 194 |
| 84 | PEx 11 | ESI+: 182 |
| 85 | PEx 11 | ESI+: 182 |
| 86 | PEx 11 | ESI+: 182 |
| 87 | PEx 11 | ESI+: 182 |
| 88 | PEx 12 | ESI+: 222 |
| 89 | PEx 14 | ESI+: 174 |
| 90 | PEx 14 | ESI+: 157 |
| 91 | PEx 14 | ESI+: 158 |
| 92 | PEx 14 | ESI+: 173 |
| 93 | PEx 14 | ESI+: 158 |
| 94 | PEx 14 | ESI+: 144 |
| 95 | PEx 14 | ESI+: 158 |
| 96 | PEx 14 | ESI+: 170 |
| 97 | PEx 16 | APCI/ESI+: 566 |
| 98 | PEx 16 | ESI+: 526 |
| 99 | PEx 16 | ESI+: 526 |
| 100 | PEx 16 | APCI/ESI+: 523 |
| 101 | PEx 16 | ESI+: 527 |
| 102 | PEx 16 | ESI+: 522 |
| 103 | PEx 16 | ESI+: 498 |

TABLE 44

| PEx | PSyn | DATA |
|---|---|---|
| 104 | PEx 16 | APCI/ESI+: 457 |
| 105 | PEx 16 | APCI/ESI+: 427 |
| 106 | PEx 16 | APCI/ESI+: 639 |
| 107 | PEx 16 | ESI+: 609 |
| 108a | PEx 17 | ESI+: 377<br>NMR (CDCl3): 0.08 (3H, s), 0.09 (3H, s), 0.91 (9H, s), 1.22 (9H, s), 2.68 (3H, s), 3.71 (1H, dd, J = 7.7, 9.9 Hz), 3.87 (1H, dd, J = 4.2, 9.9 Hz), 4.27 (1H, d, J = 3.0 Hz), 4.77 (1H, ddd, J = 3.0, 4.2, 7.7 Hz), 7.54 (1H, s) |

TABLE 44-continued

| PEx | PSyn | DATA |
|---|---|---|
| 108b | PEx 17 | ESI+: 377<br>NMR (CDCl3): 0.05 (6H, s), 0.90 (9H, s), 1.21 (9H, s), 2.67 (3H, s), 3.84 (1H, dd, J = 4.2, 9.9 Hz), 3.87-3.93 (2H, m), 4.65-4.71 (1H, m), 7.56 (1H, s) |
| 109 | PEx 18 | ESI+: 371<br>NMR (CDCl3): −0.21 (3H, s), −0.15 (3H, s), 0.74 (9H, s), 1.25 (9H, s), 1.68 (3H, s), 3.60 (1H, d, J = 9.2 Hz), 3.88 (1H, d, J = 9.2 Hz), 5.18 (1H, s), 7.09-7.14 (1H, m), 7.59-7.68 (2H, m), 8.49-8.53 (1H, m) |
| 110 | PEx 18 | ESI+: 448, 450 |
| 111 | PEx 18 | ESI+: 514 |
| 112a | PEx 18 | ESI+: 645<br>NMR (CDCl3): −0.01 (3H, s), 0.01 (3H, s), 0.87 (9H, s), 1.05 (9H, s), 1.25 (9H, s), 1.76 (3H, s), 3.79 (1H, d, J = 9.6 Hz), 3.90 (1H, d, J = 9.6 Hz), 4.57 (1H, s), 4.83 (2H, brs), 7.35-7.48 (7H, m), 7.64-7.71 (4H, m) |
| 112b | PEx 18 | ESI+: 645<br>NMR (CDCl3): −0.08 (3H, s), 0.02 (3H, s), 0.82 (9H, s), 1.06 (9H, s), 1.31 (9H, s), 1.80 (3H, s), 3.77 (1H, d, J = 9.1 Hz), 4.06 (1H, d, J = 9.1 Hz), 4.83 (2H, d, J = 0.8 Hz), 4.94 (1H, s), 7.35-7.47 (7H, m), 7.64-7.70 (4H, m) |

TABLE 45

| PEx | PSyn | DATA |
|---|---|---|
| 113a | PEx 18 | ESI+: 645<br>NMR (CDCl3): −0.08 (3H, s), −0.04 (3H, s), 0.84 (9H, s), 1.10 (9H, s), 1.24 (9H, s), 1.71 (3H, s), 3.74 (1H, d, J = 9.5 Hz), 3.87 (1H, d, J = 9.5 Hz), 4.58 (1H, s), 4.85 (2H, d, J = 1.2 Hz), 7.19 (1H, t, J = 1.2 Hz), 7.34-7.45 (6H, m), 7.67-7.73 (4H, m) |
| 113b | PEx 18 | ESI+: 645<br>NMR (CDCl3): −0.15 (3H, s), −0.03 (3H, s), 0.78 (9H, s), 1.10 (9H, s), 1.30 (9H, s), 1.76 (3H, s), 3.75 (1H, d, J = 9.2 Hz), 4.05 (1H, d, J = 9.2 Hz), 4.79-4.90 (2H, m), 4.96 (1H, s), 7.13-7.15 (1H, m), 7.34-7.46 (6H, m), 7.67-7.72 (4H, m) |
| 114 | PEx 18 | ESI+: 391 |
| 115 | PEx 20 | ESI+: 256 |
| 116 | PEx 20 | ESI+: 230 |
| 117 | PEx 20 | ESI+: 230 |
| 118 | PEx 21 | ESI+: 236 |
| 119 | PEx 23 | ESI+: 354 |
| 120 | PEx 23 | ESI+: 361 [M + Na]+ |
| 121 | PEx 25 | ESI+: 361 |
| 122 | PEx 27 | ESI+: 538 |
| 123 | PEx 28 | ESI+: 228 |
| 124 | PEx 28 | ESI+: 226 |
| 125 | PEx 28 | ESI+: 239 |
| 126 | PEx 28 | ESI+: 212 |
| 127 | PEx 28 | ESI+: 156 |
| 128 | PEx 29 | ESI+: 229 |
| 129 | PEx 29 | ESI+: 215 |
| 130 | PEx 29 | ESI+: 223 |
| 131 | PEx 29 | ESI+: 235 |
| 132 | PEx 29 | ESI+: 194 |
| 133 | PEx 29 | ESI+: 255 |

TABLE 46

| PEx | PSyn | DATA |
|---|---|---|
| 134 | PEx 30 | ESI+: 210 |
| 135 | PEx 31 | ESI+: 360 |
| 136 | PEx 32 | ESI+: 278 [M + Na]+ |
| 137 | PEx 32 | ESI+: 258 |
| 138 | PEx 32 | ESI+: 238 [M + Na]+ |
| 139 | PEx 32 | ESI+: 229 |
| 140 | PEx 32 | ESI+: 194 |
| 141 | PEx 33 | ESI+: 260, 262 |

TABLE 46-continued

| PEx | PSyn | DATA |
|---|---|---|
| 142 | PEx 32 | ESI+: 202 |
| 143 | PEx 39 | ESI+: 156 |
| 144 | PEx 32 | ESI+: 186 |
| 145 | PEx 33 | ESI+: 244 |
| 146 | PEx 36 | ESI+: 255 |
| 147 | PEx 36 | ESI+: 241 |
| 148 | PEx 36 | ESI+: 249 |
| 149 | PEx 36 | ESI+: 261 |
| 150 | PEx 36 | ESI+: 281 |
| 151 | PEx 36 | APCI/ESI+: 255 |
| 152 | PEx 38 | ESI+: 140 |
| 153 | PEx 39 | ESI+: 142 |
| 154 | PEx 40 | CI+: 177 |
| 155 | PEx 40 | ESI+: 313 [M+ Na]+ |
| 156 | PEx 43, PEx 29 | ESI+: 194 |
| 157 | PEx 44 | ESI−: 276 |
| 158 | PEx 45 | ESI+: 304 [M + Na]+ |
| 159 | PEx 45 | ESI+: 304 [M + Na]+ |
| 160 | PEx 45 | ESI+: 304 [M + Na]+ |
| 161 | PEx 47 | ESI+: 500 |
| 162 | PEx 47 | ESI+: 470 |
| 163 | PEx 47 | APCI/ESI+: 414 |
| 164 | PEx 48 | ESI+: 297 |
| 165 | PEx 49 | ESI+: 284 |

TABLE 47

| PEx | PSyn | DATA |
|---|---|---|
| 166 | PEx 49 | ESI+: 320 [M + Na]+ |
| 167 | PEx 49 | ESI+: 310 |
| 168 | PEx 50 | ESI+: 318 [M + Na]+ |
| 169 | PEx 50 | ESI+: 266 |
| 170 | PEx 50 | ESI+: 278 [M + Na]+ |
| 171 | PEx 50 | ESI+: 278 [M + Na]+ |
| 172 | PEx 50 | ESI+: 284 |
| 173 | PEx 50 | ESI+: 269 |
| 174 | PEx 50 | ESI−: 316 |
| 175 | PEx 50 | ESI+: 256 [M + Na]+ |
| 176 | PEx 50 | ESI+: 322, 324 [M + Na]+ |
| 177 | PEx 50 | ESI+: 242 |
| 178 | PEx 59 | APCI/ESI+: 256 |
| 179 | PEx 59 | ESI+: 272, 274 |
| 180 | Ex 1 | ESI+: 510 |
| 181 | Ex 1 | ESI+: 480 |
| 182 | Ex 1 | ESI+: 510 |
| 183 | Ex 1 | ESI+: 528 |
| 184 | Ex 1 | ESI+: 492 |
| 185 | Ex 1 | APCI/ESI+: 484 |
| 186 | Ex 1 | ESI+: 348 |
| 187 | Ex 1 | APCI/ESI+: 539 |
| 188 | Ex 1 | ESI+: 347 |
| 189 | Ex 1 | APCI/ESI+: 513 |
| 190 | Ex 1 | ESI+: 526 |
| 191 | Ex 1 | ESI+: 523 |
| 192 | Ex 1 | ESI+: 535 |
| 193 | Ex 1 | ESI+: 505 |
| 194 | Ex 1 | APCI/ESI+: 555 |
| 195 | Ex 1 | ESI+: 543, 545 |
| 196 | Ex 1 | ESI+: 512 |
| 197 | Ex 1 | ESI+: 338 [M + Na]+ |

TABLE 48

| PEx | PSyn | DATA |
|---|---|---|
| 198 | Ex 1 | ESI+: 297 |
| 199 | Ex 1 | APCI/ESI+: 529 |
| 200 | Ex 1, PEx 200 | ESI+: 408 |
| 201 | Ex 1 | ESI+: 324 [M + Na]+ |
| 202 | Ex 1 | ESI+: 338 [M + Na]+ |
| 203 | Ex 1 | ESI+: 350 [M + Na]+ |
| 204 | Ex 3 | ESI+: 496 |

TABLE 48-continued

| PEx | PSyn | DATA |
|---|---|---|
| 205 | Ex 3 | ESI+: 302 |
| 206 | Ex 3 | ESI+: 310 |
| 207 | Ex 3 | ESI+: 289 |
| 208a | Ex 7 | ESI+: 334 |
| 208b | Ex 7 | ESI+: 334 |
| 209a | Ex 7 | ESI+: 514 |
| 209b | Ex 7 | ESI+: 514 |
| 210a | Ex 7 | ESI+: 484 |
| 210b | Ex 7 | ESI+: 484 |
| 211 | Ex 7 | APCI/ESI+: 710 |
| 212 | Ex 7 | ESI+: 964 |
| 213 | Ex 8 | CI+: 177 |
| 214 | Ex 8 | APCI/ESI+: 243, 245 |
| 215 | PEx 5 | ESI+: 349 |
| 216 | PEx 5 | ESI+: 349 |
| 217 | PEx 8 | ESI+: 177 |
| 218 | PEx 10 | CI+: 258 |
| 219 | PEx 10 | CI+: 272 |
| 220 | PEx 10 | ESI+: 280 |
| 221 | PEx 11 | ESI+: 158 |
| 222 | PEx 11 | APCI/ESI+: 180 |
| 223 | PEx 11 | ESI+: 183 |
| 224 | PEx 11 | ESI+: 183 |
| 225 | PEx 11 | ESI+: 194 |
| 226 | PEx 14 | ESI+: 158 |

TABLE 49

| PEx | PSyn | DATA |
|---|---|---|
| 227 | PEx 14 | ESI+: 172 |
| 228 | PEx 14 | ESI+: 184 |
| 229 | PEx 14 | ESI+: 212 |
| 230 | PEx 16 | ESI+: 484 |
| 231 | PEx 16 | ESI+: 498 |
| 232 | PEx 16 | ESI+: 510 |
| 233 | PEx 18 | ESI+: 395 |
| 234 | PEx 19 | ESI+: 294 |
| 235 | PEx 28 | CI+: 226 |
| 236 | PEx 28 | ESI+: 212 |
| 237 | PEx 28 | ESI+: 282 |
| 238 | PEx 32 | ESI+: 216 |
| 239 | PEx 32 | ESI+: 202 |
| 240 | PEx 32 | ESI+: 272 |
| 241 | PEx 34 | ESI+: 213 |
| 242 | PEx 35 | ESI+: 387, 389 |
| 243 | PEx 36 | ESI+: 238 |
| 244 | PEx 38 | ESI+: 140 |
| 245 | PEx 38 | ESI+: 196 |
| 246 | PEx 39 | ESI+: 156 |
| 247 | PEx 39 | ESI+: 142 |
| 248 | PEx 39 | CI+: 128 |
| 249 | PEx 44 | ESI+: 383 |
| 250 | PEx 44 | ESI+: 383 |
| 251 | PEx 49 | ESI+: 348 |
| 252 | PEx 49 | ESI+: 312 |
| 253 | PEx 49 | ESI+: 324 |
| 254 | PEx 49 | ESI+: 362 |
| 255 | PEx 49 | ESI+: 374 |
| 256 | PEx 50 | ESI+: 256 |
| 257 | PEx 50 | ESI+: 264 [M + Na]+ |
| 258 | PEx 50 | ESI+: 312 |

TABLE 50

| PEx | PSyn | DATA |
|---|---|---|
| 259 | PEx 51 | ESI+: 214 |
| 260 | PEx 51 | ESI+: 228 |
| 261 | PEx 51 | ESI+: 240 |
| 262 | PEx 52 | ESI+: 652 |
| 263 | PEx 263 | ESI+: 306 [M + Na]+ |
| 264 | PEx 264 | ESI+: 458 |

TABLE 50-continued

| PEx | PSyn | DATA |
|---|---|---|
| 265 | PEx 265 | ESI+: 212 |
| 266 | PEx 266 | APCI/ESI+: 212 |
| 267 | PEx 267 | ESI: 374 [M + Na]+ |
| 268 | Ex 1 | ESI+: 366 |
| 269 | Ex 1 | ESI+: 512 |
| 270 | Ex 1 | ESI+: 582 |
| 271 | Ex 1 | ESI+: 330 |
| 272 | Ex 1 | ESI+: 380 |
| 273 | Ex 1 | ESI+: 364 [M + Na]+ |
| 274 | Ex 1 | ESI+: 392 |
| 275 | Ex 1 | ESI+: 512 |
| 276 | Ex 1 | ESI+: 512 |
| 277 | Ex 1 | ESI+: 494 |
| 278 | Ex 1 | ESI+: 274 |
| 279 | Ex 1 | ESI+: 515 |
| 280 | Ex 3 | ESI+: 480 |
| 281a | Ex 6 | ESI+: 392 [M + Na]+ |
| 281b | Ex 6 | ESI+: 550 |
| 282 | Ex 6 | ESI+: 520 |
| 283 | Ex 7 | ESI+: 370 [M + Na]+ |
| 284 | Ex 7 | ESI+: 384 [M + Na]+ |
| 285 | Ex 7 | ESI+: 736 |
| 286 | Ex 7 | ESI+: 298 |
| 287 | Ex 7 | ESI+: 934 |
| 288 | PEx 288 | ESI+: 292 |
| 289 | PEx 289 | ESI+: 230 |

TABLE 51

| PEx | PSyn | DATA |
|---|---|---|
| 290 | Ex 1 | ESI+: 494 |
| 291 | PEx 291 | ESI+: 347 |
| 292 | PEx 292 | ESI+: 319 |
| 293 | PEx 293 | NMR (DMSO-d6): 2.66 (3H, s), 5.47 (2H, s), 7.22-7.30 (2H, m), 7.53 (1H, dd, J = 7.0, 8.0 Hz), 7.61 (1H, tt, J = 6.8, 8.5 Hz), 7.76 (1H, d, J = 8.1 Hz), 9.12 (1H, dd, J = 0.5, 6.9 Hz) |
| 294 | PEx 294 | APCI/ESI+: 457 |
| 295 | PEx 295 | ESI+: 500 |
| 296 | PEx 296 | ESI+: 550 |
| 297 | PEx 297 | ESI+: 263 [M + Na]+ |
| 298 | PEx 298 | ESI+: 306 [M + Na]+ |
| 299 | PEx 299 | ESI+: 334 |
| 300 | PEx 300 | ESI+: 308 |
| 301 | PEx 301 | ESI+: 608 |
| 302 | PEx 302 | ESI+: 316 |
| 303 | PEx 303 | ESI+: 298 |
| 304 | PEx 304 | ESI+: 158 |
| 305 | PEx 305 | ESI+: 314 |
| 306 | PEx 306 | ESI+: 174 |
| 307 | PEx 307 | ESI+: 174 |
| 308 | PEx 2 | ESI+: 329 |
| 309 | Ex 3 | ESI+: 301 |
| 310 | Ex 3 | ESI+: 319 |

TABLE 52
| Ex | Str |
|---|---|
| 1 | 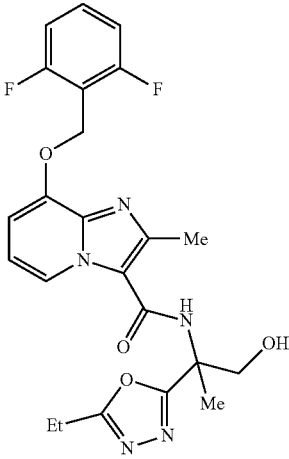 [SMILES: CCc1nnc(C(C)(CO)NC(=O)c2c(C)nc3c(OCc4c(F)cccc4F)cccn23)o1] |
| 2 | 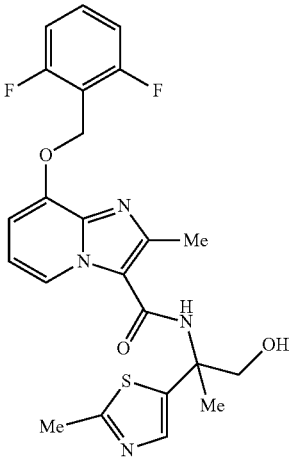 [SMILES: Cc1ncc(C(C)(CO)NC(=O)c2c(C)nc3c(OCc4c(F)cccc4F)cccn23)s1] |
| 3 | 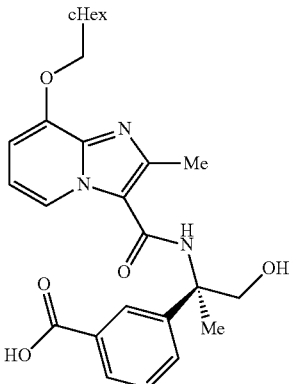 |
TABLE 52-continued
| Ex | Str |
|---|---|
| 4 | 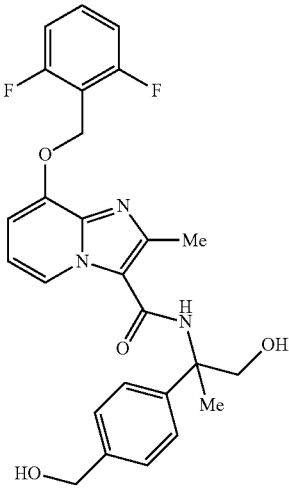 [SMILES: Cc1nc2c(OCc3c(F)cccc3F)cccn2c1C(=O)NC(C)(CO)c1ccc(CO)cc1] |
| 5 | 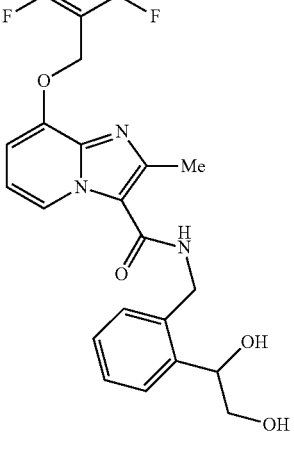 |
| 6 | 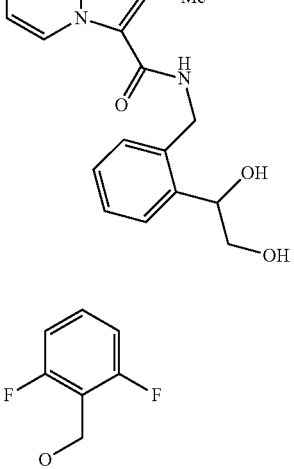 |

TABLE 53
| Ex | Str |
|---|---|
| 7a | 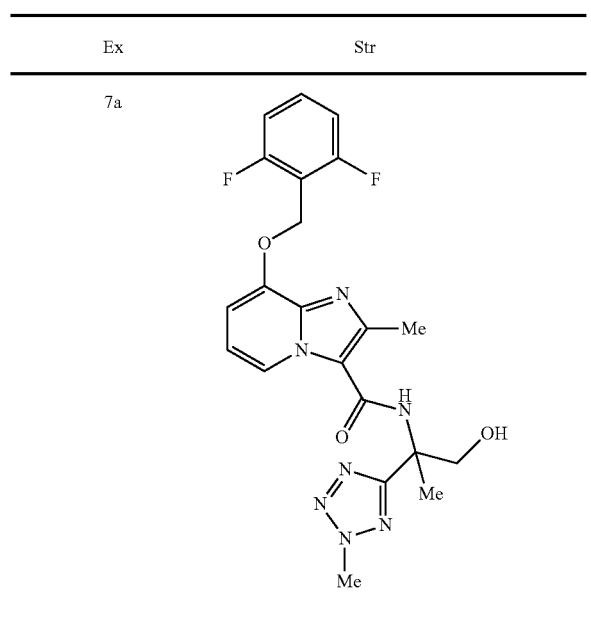 |
| 7b | |
| 8 | |
TABLE 53-continued
| Ex | Str |
|---|---|
| 9 | 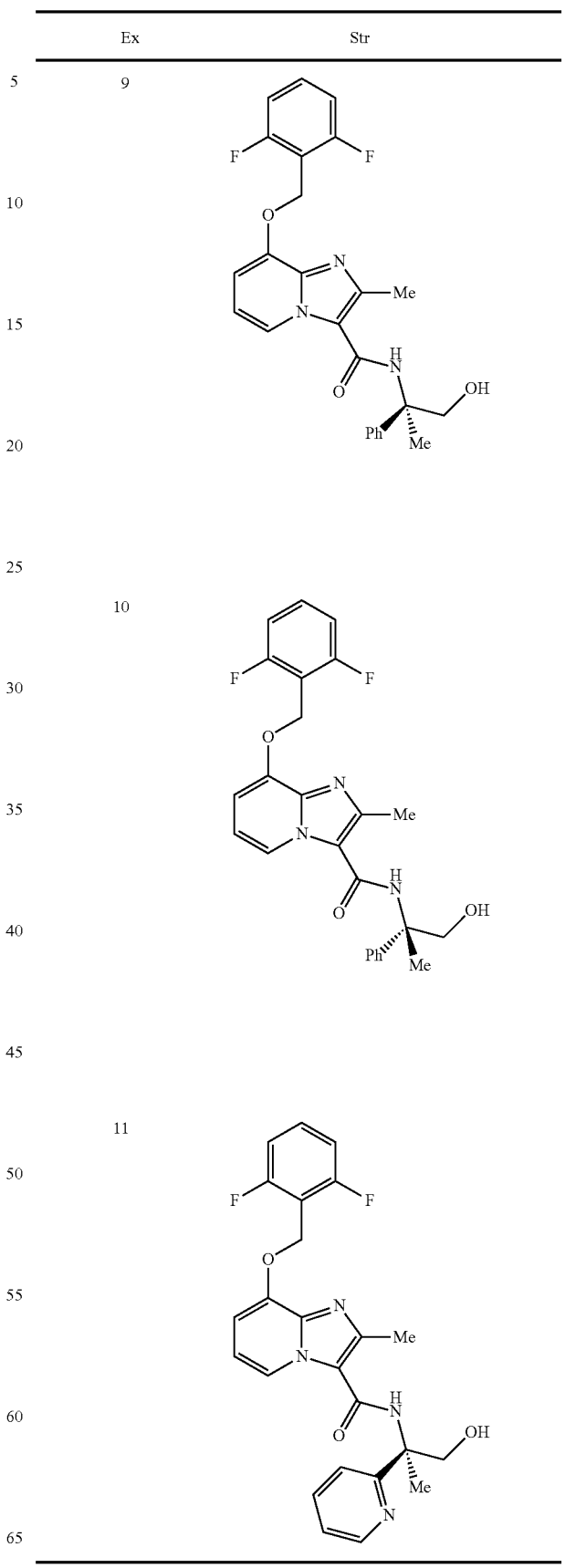 |
| 10 | |
| 11 | |

TABLE 54
| Ex | Str |
|---|---|
| 12 | 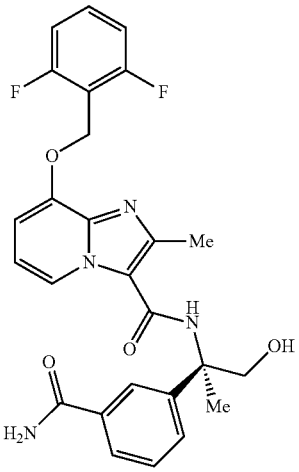 [SMILES: Cc1nc2c(OCc3c(F)cccc3F)cccn2c1C(=O)N[C@@](C)(CO)c1cccc(C(N)=O)c1] |
| 13 | 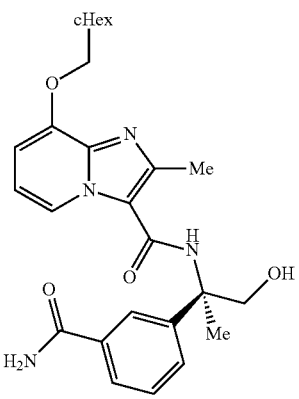 |
| 14 | 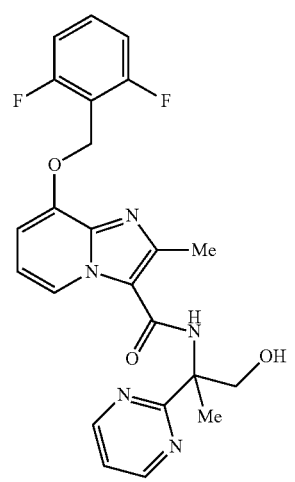 [SMILES: Cc1nc2c(OCc3c(F)cccc3F)cccn2c1C(=O)NC(C)(CO)c1ncccn1] |
TABLE 54-continued
| Ex | Str |
|---|---|
| 15 | 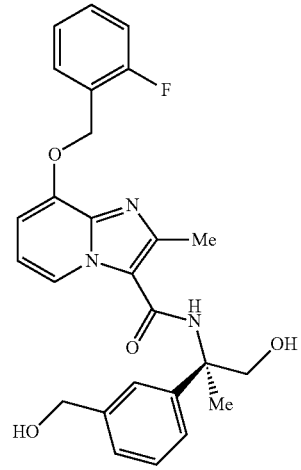 [SMILES: Cc1nc2c(OCc3ccccc3F)cccn2c1C(=O)N[C@@](C)(CO)c1cccc(CO)c1] |
| 16 | 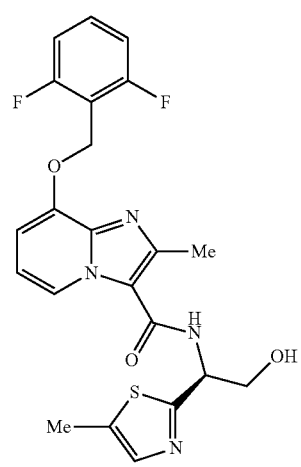 [SMILES: Cc1cnc([C@H](CO)NC(=O)c2c(C)nc3c(OCc4c(F)cccc4F)cccn23)s1] |
| 17 | 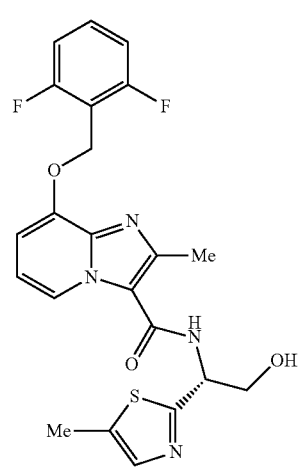 |

TABLE 55
| Ex | Str |
|---|---|
| 18 | 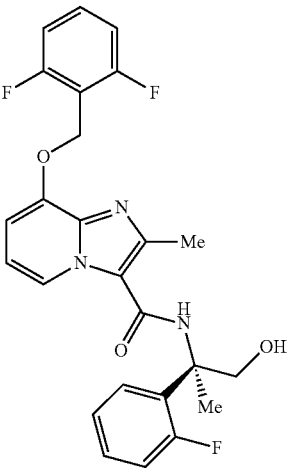 [SMILES: Cc1nc2c(OCc3c(F)cccc3F)cccn2c1C(=O)N[C@@](C)(CO)c1ccccc1F] |
| 19 | 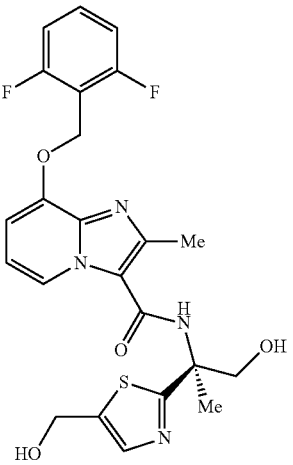 [SMILES: Cc1nc2c(OCc3c(F)cccc3F)cccn2c1C(=O)N[C@@](C)(CO)c1ncc(CO)s1] |
| 20 | 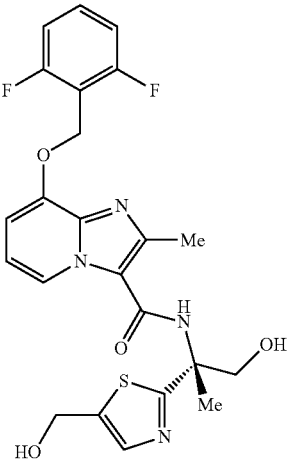 [SMILES: Cc1nc2c(OCc3c(F)cccc3F)cccn2c1C(=O)N[C@](C)(CO)c1ncc(CO)s1] |
TABLE 55-continued
| Ex | Str |
|---|---|
| 21 | 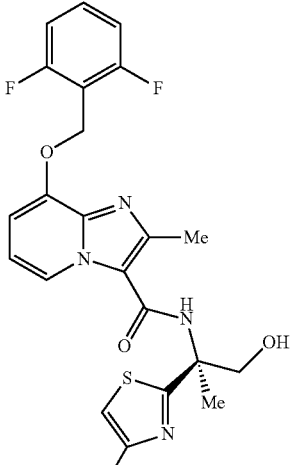 |
| 22 | 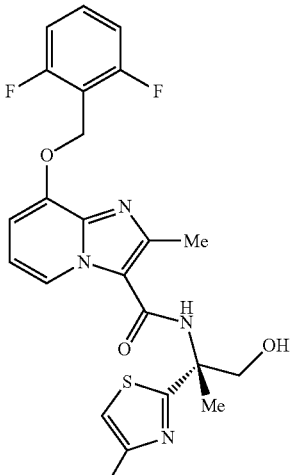 |
| 23 | 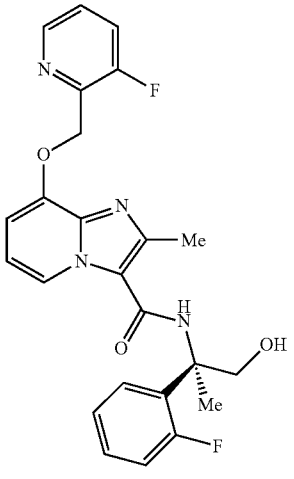 [SMILES: Cc1nc2c(OCc3ncccc3F)cccn2c1C(=O)N[C@@](C)(CO)c1ccccc1F] |

TABLE 56
| Ex | Str |
|---|---|
| 24 | 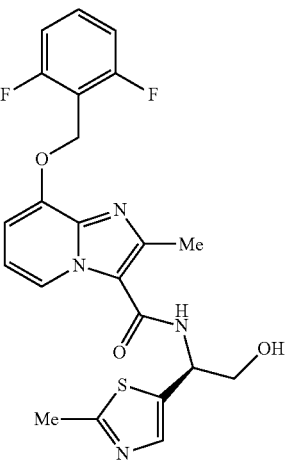 [SMILES: Cc1ncc([C@H](CO)NC(=O)c2c(C)nc3c(OCc4c(F)cccc4F)cccn23)s1] |
| 25 | 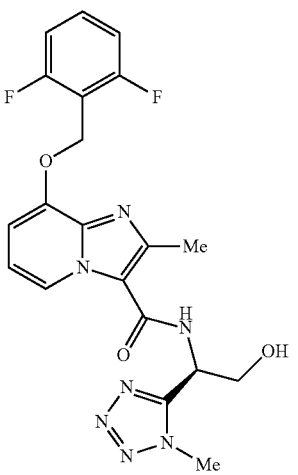 [SMILES: Cc1nc2c(OCc3c(F)cccc3F)cccn2c1C(=O)N[C@@H](CO)c1nnnn1C] |
| 26 | 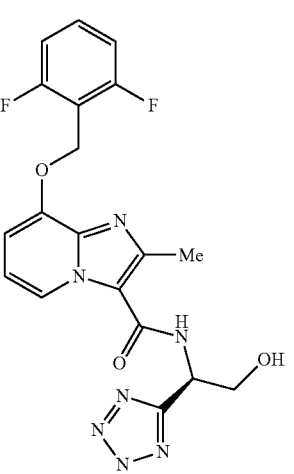 |
TABLE 56-continued
| Ex | Str |
|---|---|
| 27 | 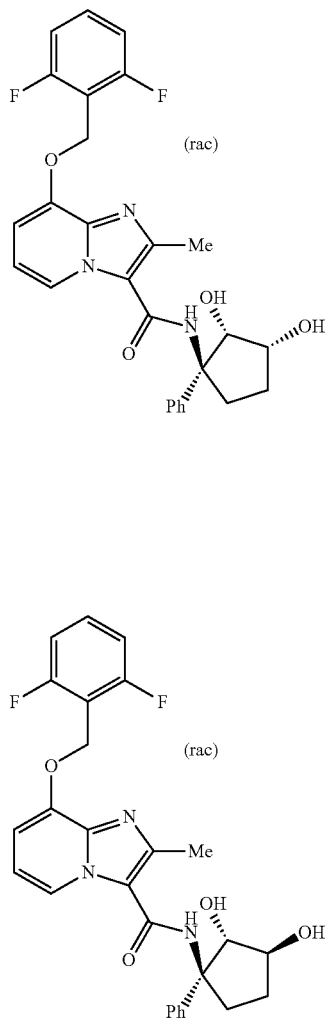 |
| 28 | |
| 29 | 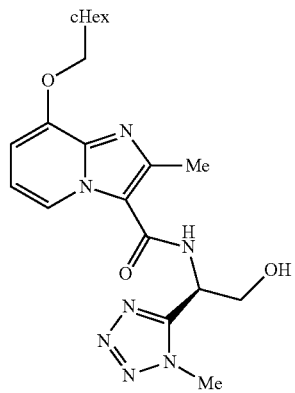 |

TABLE 57

| Ex | Str |
|---|---|
| 30 | (structure) |
| 31 | (structure) |
| 32 | (structure) |

TABLE 57-continued

| Ex | Str |
|---|---|
| 33 | (structure) |
| 34 | (structure) |
| 35 | (structure) |

TABLE 58
| Ex | Str |
|---|---|
| 36 | 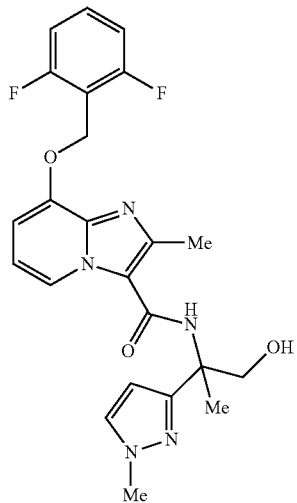 [SMILES: Cc1nc2c(OCc3c(F)cccc3F)cccn2c1C(=O)NC(C)(CO)c1ccn(C)n1] |
| 37 | 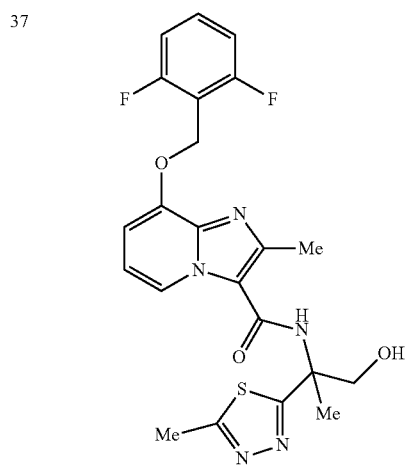 |
| 38 | 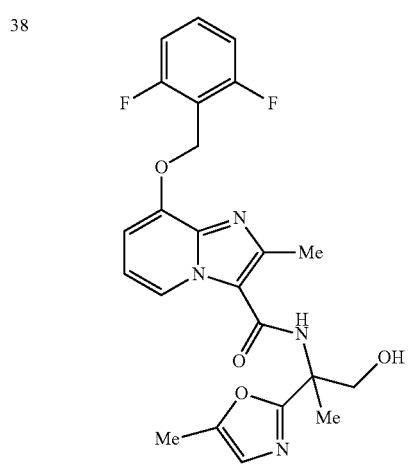 |
TABLE 58-continued
| Ex | Str |
|---|---|
| 39 | 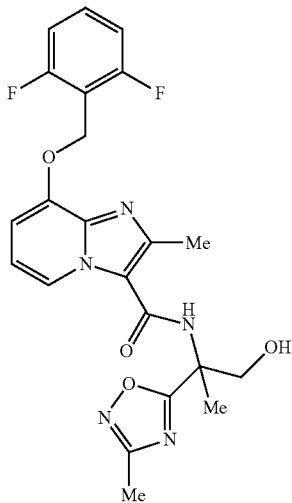 [SMILES: Cc1noc(C(C)(CO)NC(=O)c2c(C)nc3c(OCc4c(F)cccc4F)cccn23)n1] |
| 40 | 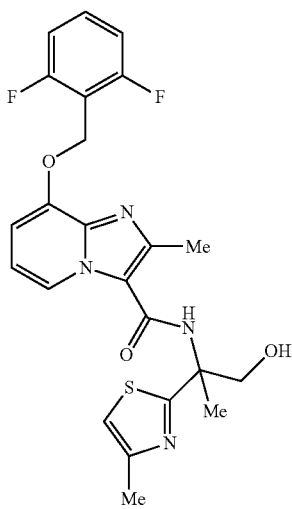 [SMILES: Cc1csc(C(C)(CO)NC(=O)c2c(C)nc3c(OCc4c(F)cccc4F)cccn23)n1] |
| 41 | 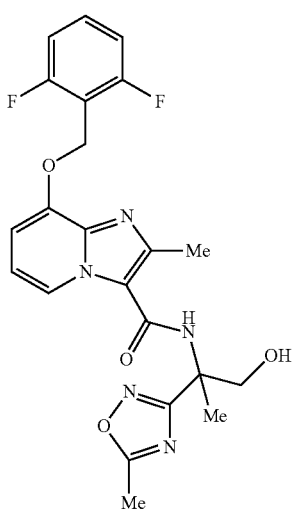 [SMILES: Cc1nc(C(C)(CO)NC(=O)c2c(C)nc3c(OCc4c(F)cccc4F)cccn23)no1] |

TABLE 59
| Ex | Str |
|---|---|
| 42 | 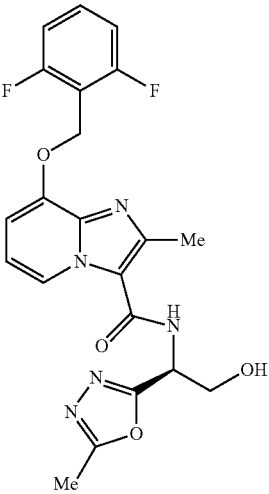 [SMILES: Cc1nnc([C@H](CO)NC(=O)c2c(C)nc3c(OCc4c(F)cccc4F)cccn23)o1] |
| 43 | 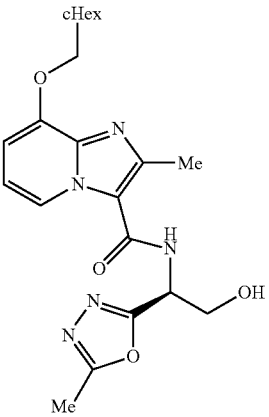 |
| 44 | 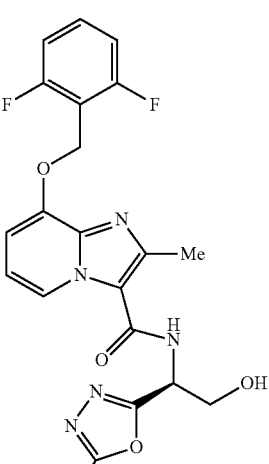 |
TABLE 59-continued
| Ex | Str |
|---|---|
| 45 | 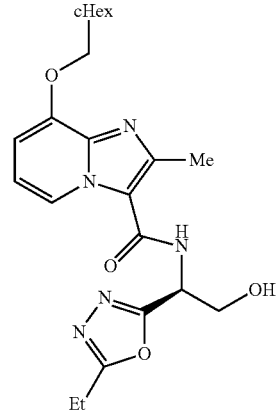 |
| 46 | 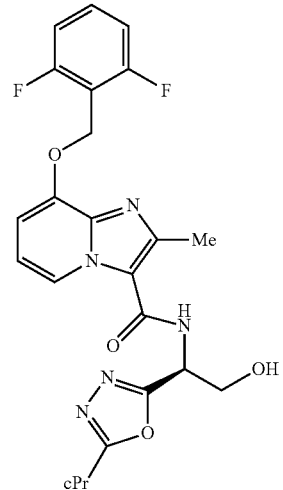 |
| 47 | 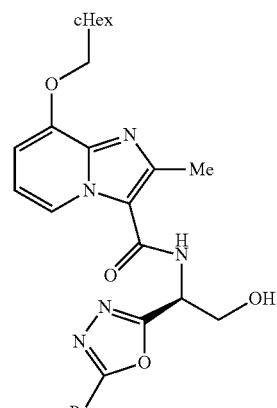 |

TABLE 60
| Ex | Str |
|---|---|
| 48 | 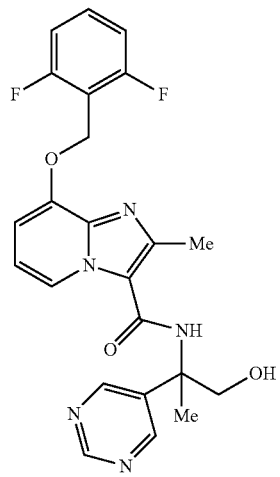 [SMILES: Cc1nc2c(OCc3c(F)cccc3F)cccn2c1C(=O)NC(C)(CO)c1cncnc1] |
| 49 | 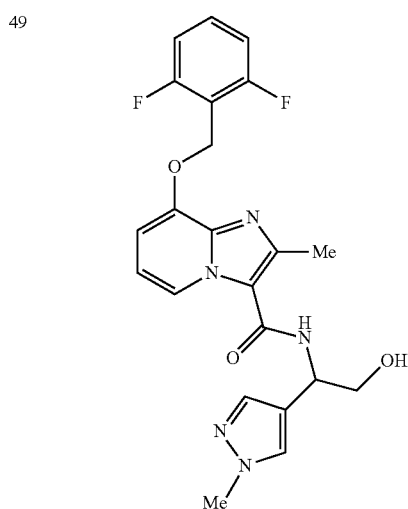 |
| 50 | 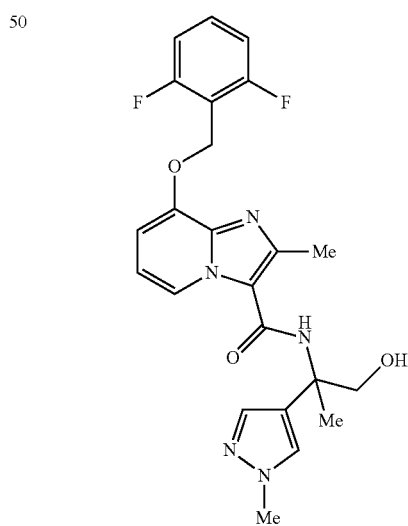 |
TABLE 60-continued
| Ex | Str |
|---|---|
| 51 | 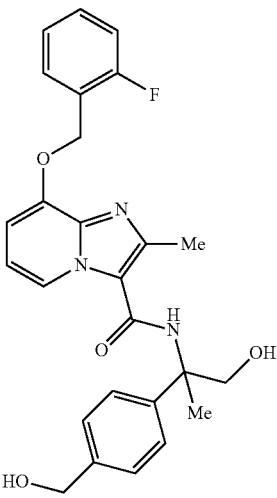 [SMILES: Cc1nc2c(OCc3ccccc3F)cccn2c1C(=O)NC(C)(CO)c1ccc(CO)cc1] |
| 52 | 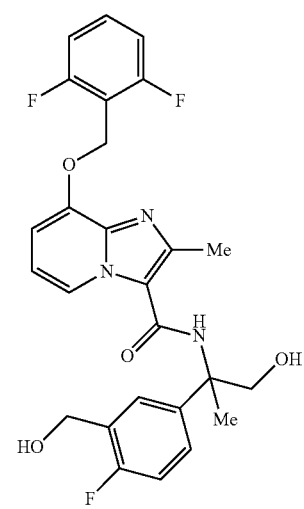 [SMILES: Cc1nc2c(OCc3c(F)cccc3F)cccn2c1C(=O)NC(C)(CO)c1ccc(F)c(CO)c1] |
| 53 | 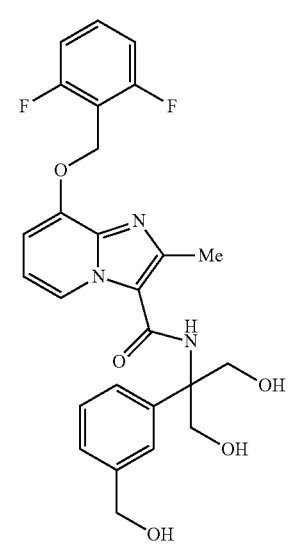 [SMILES: Cc1nc2c(OCc3c(F)cccc3F)cccn2c1C(=O)NC(CO)(CO)c1cccc(CO)c1] |

TABLE 61
| Ex | Str |
|----|-----|
| 54 | |
| 55 | |
| 56 | |
TABLE 61-continued
| Ex | Str |
|----|-----|
| 57 | |
TABLE 62
| Ex | Str |
|----|-----|
| 58 | 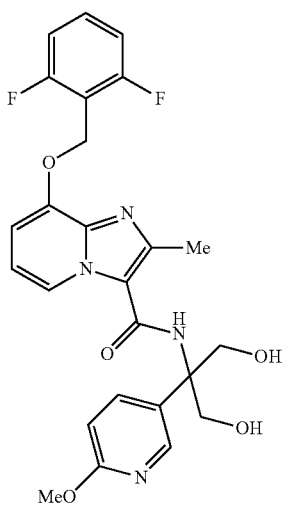 [SMILES: COc1ccc(C(CO)(CO)NC(=O)c2c(C)nc3c(OCc4c(F)cccc4F)cccn23)cn1] |

TABLE 62-continued
| Ex | Str |
|---|---|
| 59 | 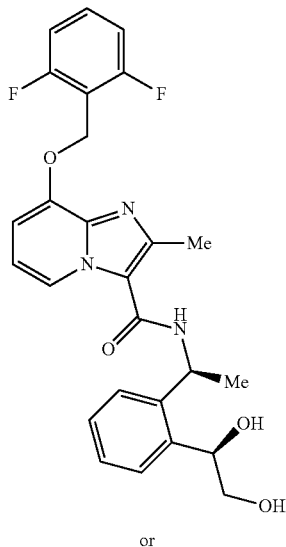 [SMILES: Cc1nc2c(OCc3c(F)cccc3F)cccn2c1C(=O)N[C@@H](C)c1ccccc1[C@@H](O)CO] or 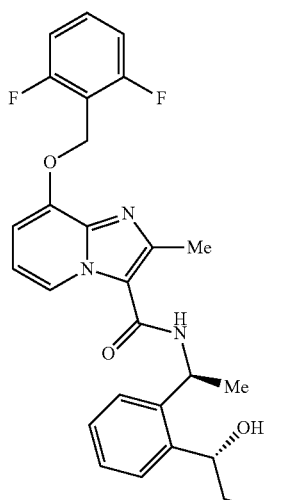 |
| 60 | 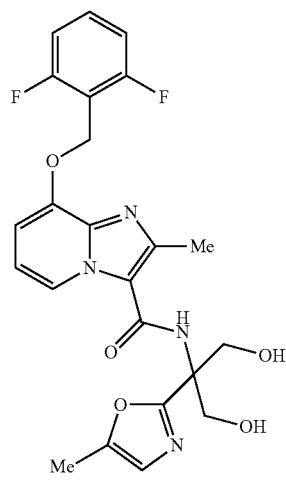 [SMILES: Cc1cnc(C(CO)(CO)NC(=O)c2c(C)nc3c(OCc4c(F)cccc4F)cccn23)o1] |
TABLE 62-continued
| Ex | Str |
|---|---|
| 61 | 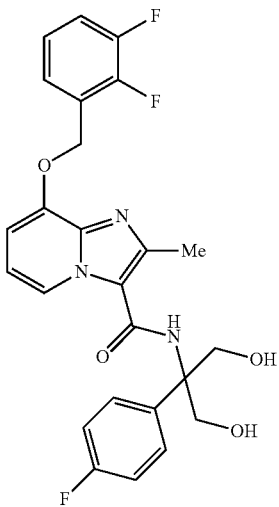 [SMILES: Cc1nc2c(OCc3cccc(F)c3F)cccn2c1C(=O)NC(CO)(CO)c1ccc(F)cc1] |
TABLE 63
| Ex | Str |
|---|---|
| 62 | 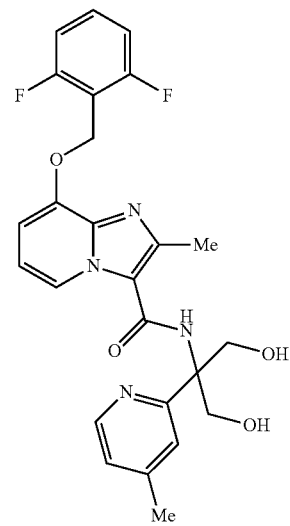 [SMILES: Cc1ccnc(C(CO)(CO)NC(=O)c2c(C)nc3c(OCc4c(F)cccc4F)cccn23)c1] |

TABLE 63-continued
| Ex | Str |
|---|---|
| 63 | 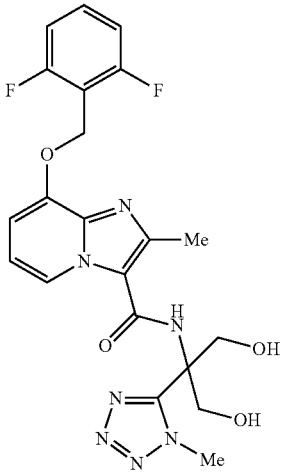 [SMILES: Cc1nc2c(OCc3c(F)cccc3F)cccn2c1C(=O)NC(CO)(CO)c1nnnn1C] |
| 64 | 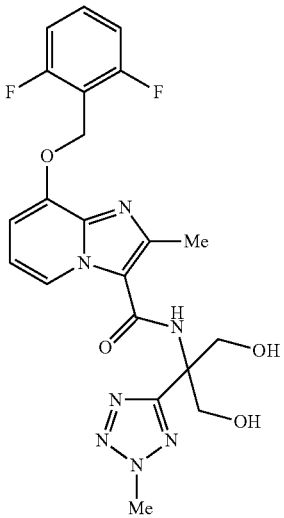 [SMILES: Cc1nc2c(OCc3c(F)cccc3F)cccn2c1C(=O)NC(CO)(CO)c1nnn(C)n1] |
| 65 | 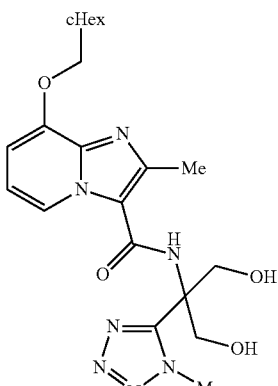 |
| 66 | 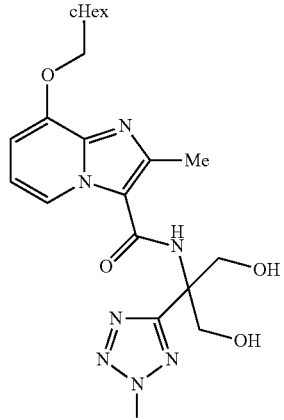 |
| 67 | 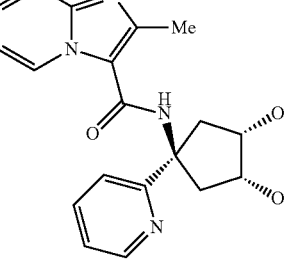 |
TABLE 64
| Ex | Str |
|---|---|
| 68 | 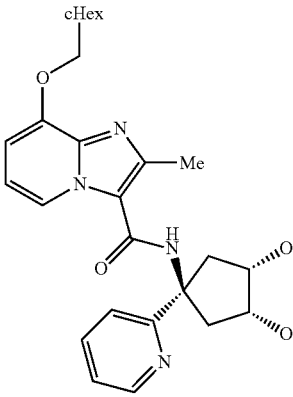 |

TABLE 64-continued
| Ex | Str |
|---|---|
| 69 | 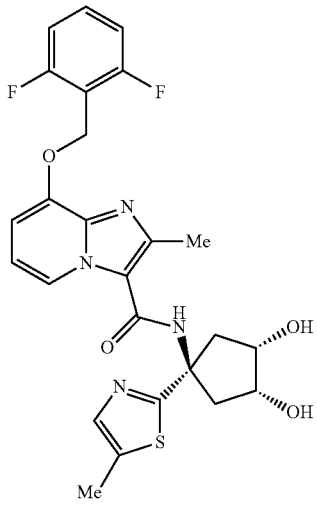 or 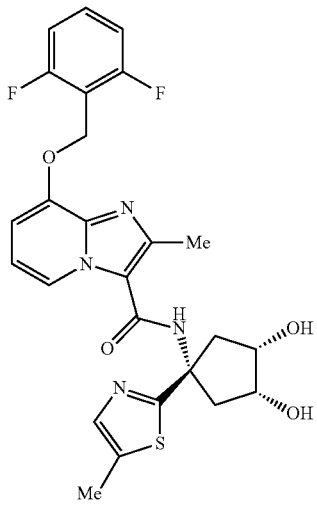 [SMILES: Cc1cnc([C@]2(NC(=O)c3c(C)nc4c(OCc5c(F)cccc5F)cccn34)C[C@@H](O)[C@@H](O)C2)s1] |
| 70 | 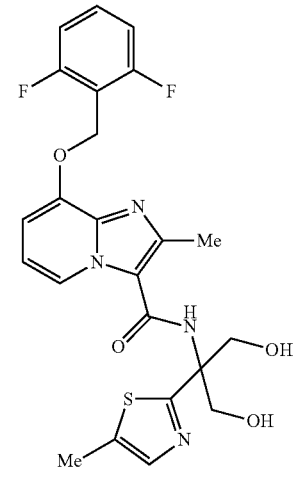 [SMILES: Cc1cnc(C(CO)(CO)NC(=O)c2c(C)nc3c(OCc4c(F)cccc4F)cccn23)s1] |
TABLE 64-continued
| Ex | Str |
|---|---|
| 71 | 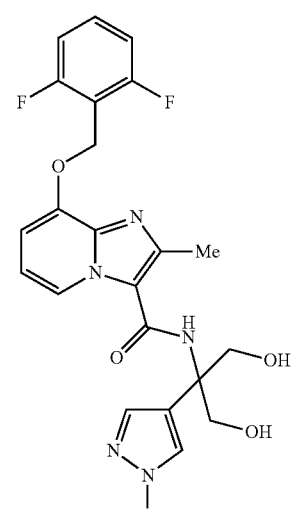 |
TABLE 65
| Ex | Str |
|---|---|
| 72 | 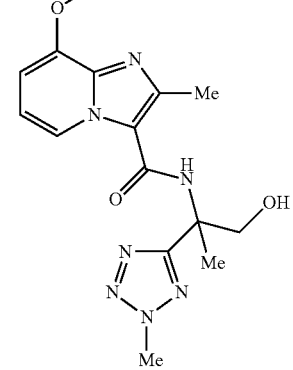 |
| 73a | 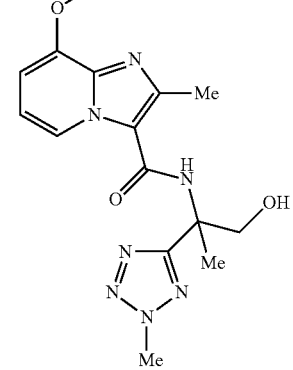 |

TABLE 65-continued

| Ex | Str |
|---|---|
| 73b | (structure) |
| 74 | (structure) |
| 75 | (structure) |

TABLE 65-continued

| Ex | Str |
|---|---|
| 76 | (structure) |

TABLE 66

| Ex | Str |
|---|---|
| 77 | (structure) |
| 78 | (structure) |

TABLE 66-continued
| Ex | Str |
|---|---|
| 79 | 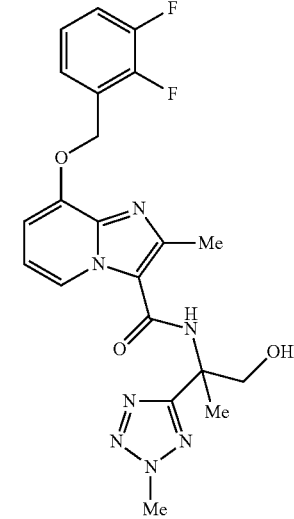 [SMILES: Cc1nc2c(OCc3cccc(F)c3F)cccn2c1C(=O)NC(C)(CO)c1nnn(C)n1] |
| 80 | |
| 81 | |
TABLE 66-continued
| Ex | Str |
|---|---|
| 82 | 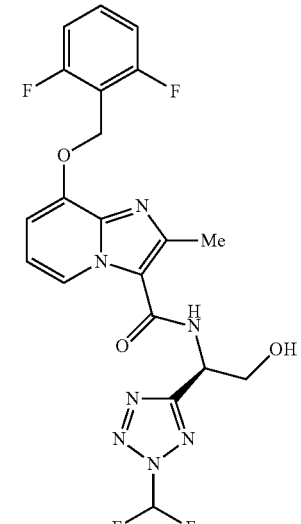 |
TABLE 67
| Ex | Str |
|---|---|
| 83 | |
| 84 | 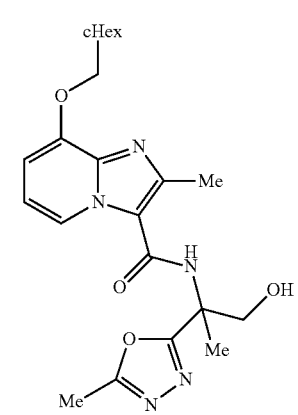 |

TABLE 67-continued

| Ex | Str |
|---|---|
| 85 | (8-(cyclohexylmethoxy)-2-methylimidazo[1,2-a]pyridine-3-carboxamide with N-[(1S)-1-(3-cyanophenyl)-2-hydroxy-1-methylethyl]) |
| 86 | (8-(cyclohexylmethoxy)-2-methylimidazo[1,2-a]pyridine-3-carboxamide with 2-(5-ethyl-1,3,4-oxadiazol-2-yl)-1-hydroxymethyl-propan-2-yl) |
| 87 | (8-[(2,6-difluorobenzyl)oxy]-2-methylimidazo[1,2-a]pyridine-3-carboxamide with 2-(5-cyclopropyl-1,3,4-oxadiazol-2-yl)-1-hydroxymethyl-propan-2-yl) |
| 88 | (8-(cyclohexylmethoxy)-2-methylimidazo[1,2-a]pyridine-3-carboxamide with 2-(5-cyclopropyl-1,3,4-oxadiazol-2-yl)-1-hydroxymethyl-propan-2-yl) |

TABLE 68

| Ex | Str |
|---|---|
| 89 | (rac) 8-[(2,6-difluorobenzyl)oxy]-2-methyl-imidazo[1,2-a]pyridine-3-carboxamide derivative with pyridin-3-yl(1,2-dihydroxypropyl) |
| 90 | (rac) 8-[(2,6-difluorobenzyl)oxy]-2-methyl-imidazo[1,2-a]pyridine-3-carboxamide derivative with pyridin-4-yl(1,2-dihydroxypropyl) |

TABLE 68-continued
| Ex | Str |
|---|---|
| 91 | 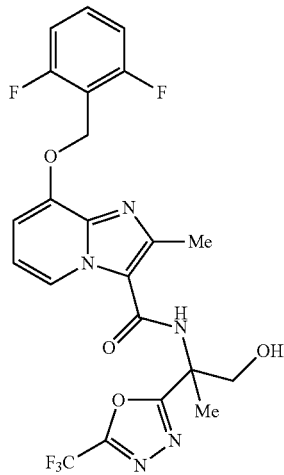 |
| 92 | 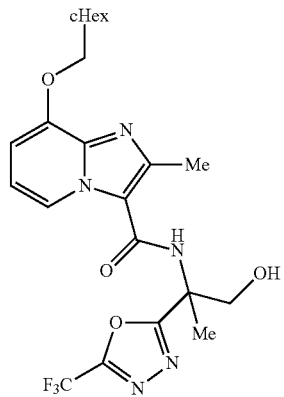 |
| 93 | 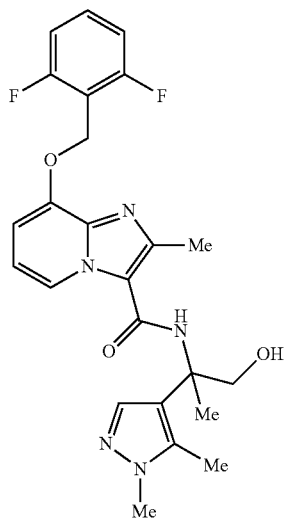 [SMILES: Cc1nc2c(OCc3c(F)cccc3F)cccn2c1C(=O)NC(C)(CO)c1cnn(C)c1C] |
TABLE 68-continued
| Ex | Str |
|---|---|
| 94 | 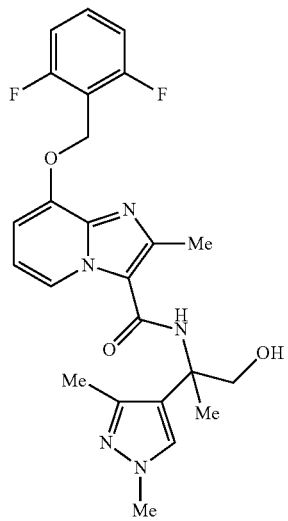 [SMILES: Cc1nn(C)cc1C(C)(CO)NC(=O)c1c(C)nc2c(OCc3c(F)cccc3F)cccn12] |
TABLE 69
| Ex | Str |
|---|---|
| 95 | 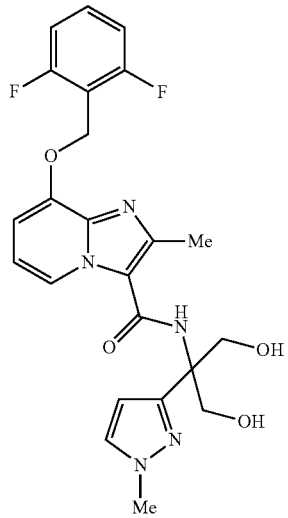 [SMILES: Cc1nc2c(OCc3c(F)cccc3F)cccn2c1C(=O)NC(CO)(CO)c1ccn(C)n1] |

TABLE 69-continued
| Ex | Str |
|---|---|
| 96 | 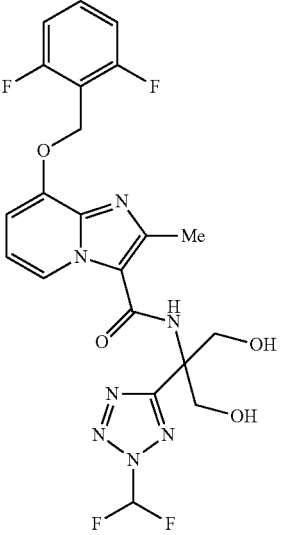 [SMILES: Cc1nc2c(OCc3c(F)cccc3F)cccn2c1C(=O)NC(CO)(CO)c1nnn(C(F)F)n1] |
| 97 | 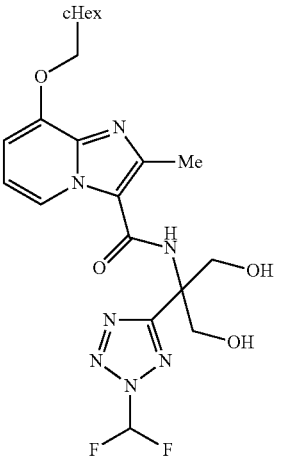 |
| 98 | 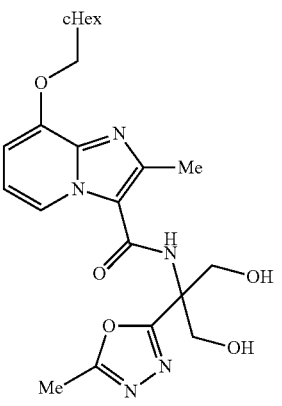 |
| 99 | 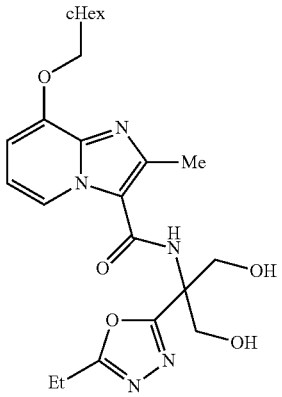 |
| 100 | 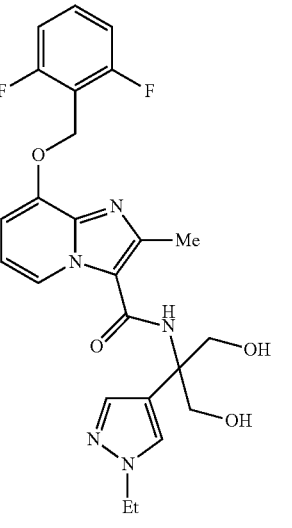 |
TABLE 70
| Ex | Str |
|---|---|
| 101 | 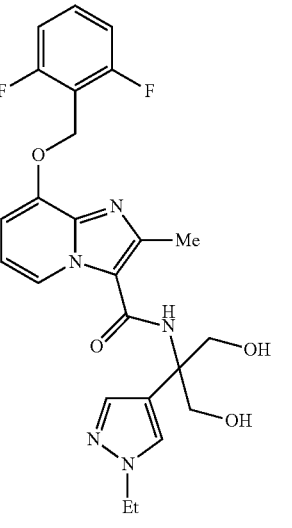 |

TABLE 70-continued
| Ex | Str |
|---|---|
| 102 | 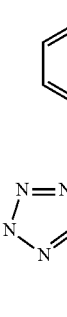 |
| 103 | 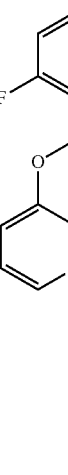 |
| 104 | 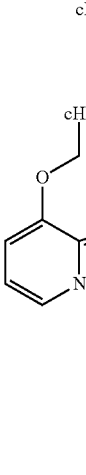 |
| 105 | 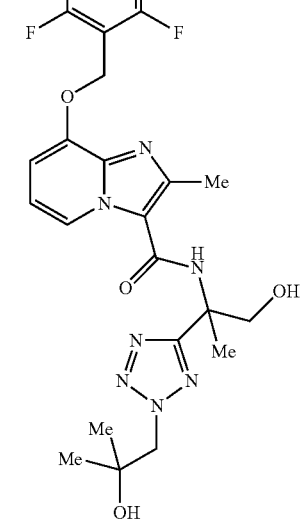 |
| 106 | 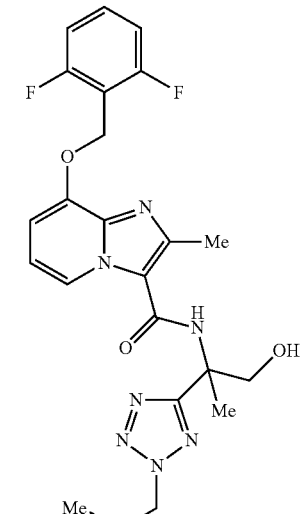 |

TABLE 71

| Ex | Str |
|---|---|
| 107a and 107b | (chemical structures of two diastereomers: 8-(2,6-difluorobenzyloxy)-2-methylimidazo[1,2-a]pyridine-3-carboxamide linked to N-[(1)-1-(4-(hydroxymethyl)phenyl)-2-hydroxy-1-methylethyl]) |
| 108a and | (chemical structure: 8-(2,6-difluorobenzyloxy)-2-methylimidazo[1,2-a]pyridine-3-carboxamide with N-[(1)-2-hydroxy-1-methyl-1-(2-methyl-2H-tetrazol-5-yl)ethyl]) |

TABLE 71-continued

| Ex | Str |
|---|---|
| 108b | (chemical structure: 8-(2,6-difluorobenzyloxy)-2-methylimidazo[1,2-a]pyridine-3-carboxamide with N-[(1)-2-hydroxy-1-methyl-1-(2-methyl-2H-tetrazol-5-yl)ethyl], other diastereomer) |

TABLE 72

| Ex | Str |
|---|---|
| 109 | (chemical structure: 8-(2,6-difluorobenzyloxy)-2-methylimidazo[1,2-a]pyridine-3-carboxamide with N-[2-(1,3-dimethyl-1H-pyrazol-4-yl)-1,3-dihydroxy-2-propyl]) |

TABLE 72-continued
| Ex | Str |
|---|---|
| 110 | 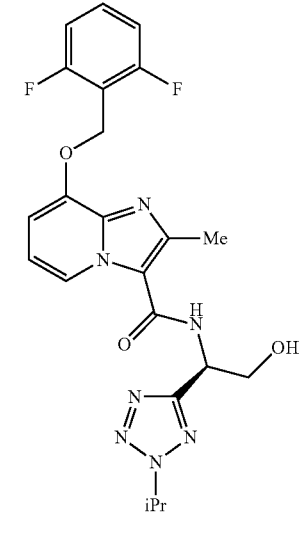 [SMILES: Cc1nc2c(OCc3c(F)cccc3F)cccn2c1C(=O)N[C@@H](CO)c1nnn(C(C)C)n1] |
| 111 | |
| 112 | |
| Ex | Str |
|---|---|
| 113 | 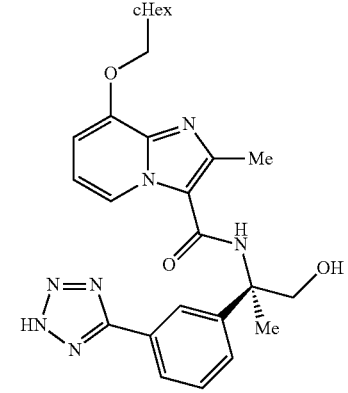 |
| 114 | 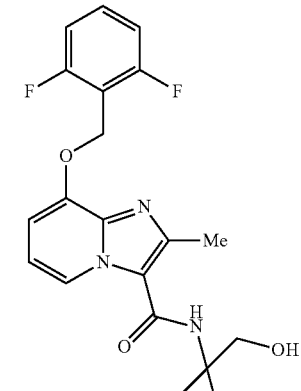 |

TABLE 73

| Ex | Str |
|---|---|
| 115 | 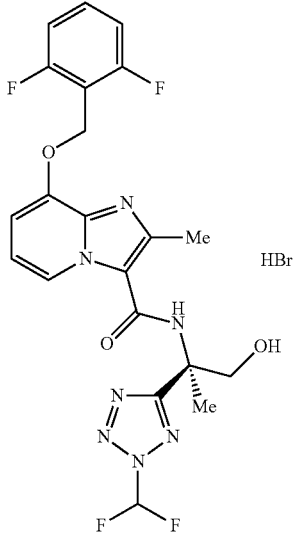 [SMILES: Cc1nc2c(OCc3c(F)cccc3F)cccn2c1C(=O)N[C@@](C)(CO)c1nnn(C(F)F)n1 ; Br] |
| 116 | 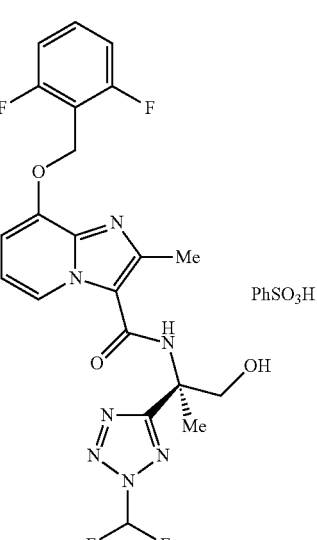 |
| 117 | 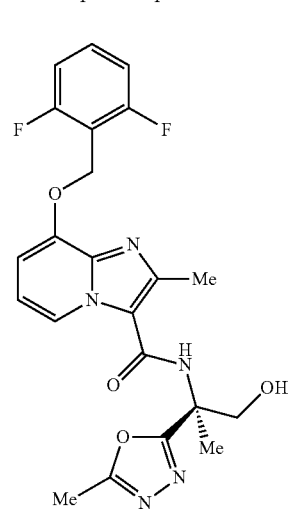 |

TABLE 73-continued

| Ex | Str |
|---|---|
| 118 | 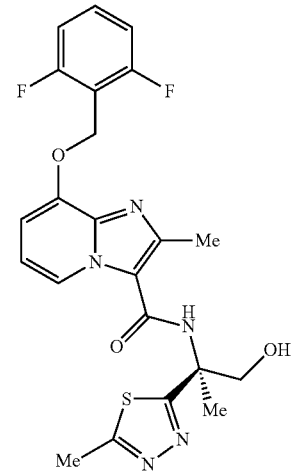 [SMILES: Cc1nnc([C@](C)(CO)NC(=O)c2c(C)nc3c(OCc4c(F)cccc4F)cccn23)s1] |

TABLE 74

| Ex | Syn | DATA |
|---|---|---|
| 1 | Ex 1 | ESI+: 472<br>NMR (DMSO-d6): 1.22 (3H, t, J = 7.5 Hz), 1.74 (3H, s), 2.56 (3H, s), 2.81 (2H, q, J = 7.6 Hz), 3.81 (1H, dd, J = 6.2, 10.9 Hz), 3.89 (1H, dd, J = 6.2, 10.8 Hz), 5.31 (2H, s), 5.37 (1H, t, J = 6.1 Hz), 6.92 (1H, dd, J = 7.0, 7.6 Hz), 7.01 (1H, dd, J = 0.7, 7.8 Hz), 7.19-7.27 (2H, m), 7.58 (1H, tt, J = 6.7, 8.5 Hz), 8.05 (1H, s), 8.45 (1H, dd, J = 0.8, 6.8 Hz) |
| 2 | Ex 2 | ESI+: 473<br>NMR (DMSO-d6): 1.77 (3H, s), 2.56 (3H, s), 2.57 (3H, s), 3.68 (1H, dd, J = 5.7, 10.6 Hz), 3.81 (1H, dd, J = 5.8, 10.6 Hz), 5.31 (2H, s), 5.40 (1H, t, J = 5.7 Hz), 6.92 (1H, dd, J = 6.9, 7.6 Hz), 7.00 (1H, dd, J = 0.8, 7.7 Hz), 7.19-7.26 (2H, m), 7.47 (1H, s), 7.58 (1H, tt, J = 6.7, 8.4 Hz), 7.77 (1H, s), 8.53 (1H, dd, J = 0.9, 6.9 Hz) |
| 3 | Ex 3 | ESI+: 466 |
| 4 | Ex 4 | ESI+: 482 |
| 5 | Ex 5 | ESI+: 468 |
| 6 | Ex 6 | ESI+: 494<br>NMR (DMSO-d6): 1.84 (3H, s), 2.60 (3H, s), 3.85 (1H, dd, J = 6.1, 10.8 Hz), 3.93 (1H, dd, J = 6.1, 10.8 Hz), 5.29-5.35 (3H, m), 6.90 (1H, dd, J = 7.0, 7.6 Hz), 7.01 (1H, dd, J = 0.8, 7.8 Hz), 7.19-7.26 (2H, m), 7.58 (1H, tt, J = 6.7, 8.5 Hz), 8.13 (1H, s), 8.41 (1H, dd, J = 0.8, 6.8 Hz), 8.57 (1H, t, J = 56.8 Hz) |
| 7a | Ex 7 | ESI+: 458<br>NMR (DMSO-d6): 1.79 (3H, s), 2.60 (3H, s), 3.78 (1H, dd, J = 6.1, 10.6 Hz), 3.92 (1H, dd, J = 6.0, 10.7 Hz), 4.33 (3H, s), 5.24 (1H, t, J = 6.0 Hz), 5.31 (2H, s), 6.90 (1H, dd, J = 7.0, 7.6 Hz), 7.00 (1H, dd, J = 0.8, 7.7 Hz), 7.19-7.26 (2H, m), 7.58 (1H, tt, J = 6.7, 8.5 Hz), 7.87 (1H, s), 8.49 (1H, dd, J = 0.9, 6.9 Hz) |

TABLE 75

| Ex | Syn | DATA |
|---|---|---|
| 7b | Ex 7 | ESI+: 458<br>NMR (DMSO-d6): 1.78 (3H, s), 2.62 (3H, s), 3.81 (1H, dd, J = 6.0, 11.2 Hz), 3.94 (1H, dd, J = 5.5, 11.1 Hz), 4.02 (3H, s), 5.31 (2H, s), 5.52 (1H, t, J = 5.8 Hz), 6.92 (1H, dd, J = 6.9, 7.6 Hz), 7.03 (1H, dd, J = 0.7, 7.8 Hz), 7.19-7.27 (2H, m), 7.59 (1H, tt, J = 6.8, 8.5 Hz), 8.16 (1H, s), 8.49 (1H, dd, J = 0.9, 6.9 Hz) |
| 8 | Ex 8 | ESI+: 472<br>NMR (DMSO-d6): 1.50 (3H, t, J = 7.3 Hz), 1.79 (3H, s), |

TABLE 75-continued

| Ex | Syn | DATA |
|---|---|---|
| | | 2.60 (3H, s), 3.80 (1H, dd, J = 5.5, 10.7 Hz), 3.92 (1H, dd, J = 5.4, 10.7 Hz), 4.65 (2H, q, J = 7.3 Hz), 5.23 (1H, t, J = 5.6 Hz), 5.31 (2H, s), 6.90 (1H, dd, J = 6.9, 7.6 Hz), 7.00 (1H, dd, J = 0.8, 7.7 Hz), 7.19-7.27 (2H, m), 7.58 (1H, tt, J = 6.7, 8.5 Hz), 7.89 (1H, s), 8.48 (1H, dd, J = 0.9, 6.9 Hz) |
| 9 | Ex 1 | ESI+: 452<br>NMR (DMSO-d6): 1.75 (3H, s), 2.64 (3H, s), 3.59 (1H, dd, J = 5.4, 10.6 Hz), 3.74 (1H, dd, J = 5.7, 10.6 Hz), 5.24 (1H, t, J = 5.6 Hz), 5.31 (2H, s), 6.89 (1H, dd, J = 7.0, 7.6 Hz), 7.00 (1H, dd, J = 0.8, 7.7 Hz), 7.18-7.27 (3H, m), 7.31 (2H, t, J = 7.7 Hz), 7.39-7.43 (2H, m), 7.59 (1H, tt, J = 6.8, 8.5 Hz), 7.62 (1H, s), 8.56 (1H, dd, J = 0.8, 6.9 Hz) |
| 10 | Ex 1 | ESI+: 452 |
| 11 | Ex 1 | ESI+: 453 |
| 12 | Ex 1 | ESI+: 495 |
| 13 | Ex 1 | ESI+: 465 |
| 14 | Ex 1 | ESI+: 454 |
| 15 | Ex 1 | ESI+: 464 |

TABLE 76

| Ex | Syn | DATA |
|---|---|---|
| 16 | Ex 1 | ESI+: 459<br>NMR (DMSO-d6): 2.40 (3H, d, J = 1.1 Hz), 2.60 (3H, s), 3.81-3.89 (1H, m), 3.89-3.97 (1H, m), 5.11-5.18 (1H, m), 5.29-5.36 (1H, m), 5.32 (2H, s), 6.96 (1H, dd, J = 7.0, 7.6 Hz), 7.04 (1H, dd, J = 0.8, 7.8 Hz), 7.19-7.27 (2H, m), 7.43 (1H, q, J = 1.1 Hz), 7.59 (1H, tt, J = 6.7, 8.5 Hz), 8.29-8.34 (1H, m), 8.60 (1H, dd, J = 0.9, 6.8 Hz)<br>[α]$_D$ = −7.81 (c 0.52, 26.3° C., MeOH) |
| 17 | Ex 1 | ESI+: 459<br>[α]$_D$ = +7.92 (c 0.52, 26.4° C., MeOH) |
| 18 | Ex 1 | ESI+: 470 |
| 19 | Ex 1 | ESI+: 489<br>NMR (DMSO-d6): 1.78 (3H, s), 2.62 (3H, s), 3.78 (1H, dd, J = 5.8, 10.7 Hz), 3.94 (1H, dd, J = 6.0, 10.7 Hz), 4.62 (2H, dd, J = 0.7, 5.7 Hz), 5.29-5.35 (3H, m), 5.46 (1H, t, J = 5.7 Hz), 6.93 (1H, t, J = 7.3 Hz), 7.02 (1H, d, J = 7.2 Hz), 7.19-7.27 (2H, m), 7.50 (1H, s), 7.59 (1H, tt, J = 6.8, 8.4 Hz), 7.97 (1H, s), 8.57 (1H, dd, J = 0.7, 6.9 Hz)<br>[α]$_D$ = −7.47 (c 0.43, 25.8° C., MeOH) |
| 20 | Ex 1 | ESI+: 489<br>[α]$_D$ = +4.42 (c 0.33, 25.6° C., MeOH) |
| 21 | Ex 1 | ESI+: 489 |
| 22 | Ex 1 | ESI+: 489 |
| 23 | Ex 1 | ESI+: 453 |
| 24 | Ex 1 | ESI+: 459 |
| 25 | Ex 1 | ESI+: 444 |
| 26 | Ex 1 | ESI+: 444<br>NMR (DMSO-d6): 2.56 (3H, s), 3.85-3.97 (2H, m), 4.35 (3H, s), 5.12 (1H, t, J = 5.7 Hz), 5.31 (2H, s), 5.41-5.47 (1H, m), 6.94 (1H, dd, J = 6.9, 7.6 Hz), 7.02 (1H, dd, J = 0.9, 7.7 Hz), 7.19-7.27 (2H, m), 7.59 (1H, tt, J = 6.7, 8.5 Hz), 8.25 (1H, d, J = 8.2 Hz), 8.57 (1H, dd, J = 0.9, 6.8 Hz) |
| 27 | Ex 1 | ESI+: 494 |

TABLE 77

| Ex | Syn | DATA |
|---|---|---|
| 28 | Ex 1 | ESI+: 494 |
| 29 | Ex 1 | ESI+: 414 |
| 30 | Ex 1 | ESI+: 482 |
| 31 | Ex 1 | ESI+: 482<br>NMR (DMSO-d6): 0.93 (3H, d, J = 6.3 Hz), 2.53 (3H, s), 3.78-3.88 (1H, m), 4.56 (1H, dd, J = 5.5, 15.2 Hz), 4.69-4.76 (3H, m), 5.21 (1H, d, J = 4.1 Hz), 5.31 (2H, s), 6.94 (1H, dd, J = 6.9, 7.6 Hz), 7.02 (1H, dd, J = 0.9, 7.7 Hz), 7.19-7.27 (4H, m), 7.32-7.37 (1H, m), 7.39-7.45 (1H, m), 7.58 (1H, tt, J = 6.7, 8.4 Hz), 8.21 (1H, t, J = 5.8 Hz), 8.69 (1H, dd, J = 0.9, 6.9 Hz) |
| 32 | Ex 1 | ESI+: 482 |
| 33 | Ex 1 | ESI+: 482 |
| 34 | Ex 1 | ESI+: 414 |
| 35 | Ex 1 | ESI+: 458<br>NMR (DMSO-d6): 1.74 (3H, s), 2.45 (3H, s), 2.57 (3H, s), 3.81 (1H, dd, J = 6.2, 10.9 Hz), 3.88 (1H, dd, J = 6.1, 10.8 Hz), 5.31 (2H, s), 5.37 (1H, t, J = 6.1 Hz), 6.92 (1H, t, J = 7.3 Hz), 7.02 (1H, d, J = 7.4 Hz), 7.19-7.27 (2H, m), 7.58 (1H, tt, J = 6.8, 8.4 Hz), 8.01 (1H, s), 8.47 (1H, d, J = 6.3 Hz) |
| 36 | Ex 1 | ESI+: 456 |
| 37 | Ex 1 | ESI+: 474 |
| 38 | Ex 1 | ESI+: 457 |
| 39 | Ex 1 | ESI+: 458 |
| 40 | Ex 1 | ESI+: 473 |
| 41 | Ex 1 | ESI+: 458 |
| 42 | Ex 1 | ESI+: 444 |
| 43 | Ex 1 | ESI+: 414 |
| 44 | Ex 1 | ESI+: 458 |
| 45 | Ex 1 | ESI+: 428 |
| 46 | Ex 1 | ESI+: 470 |

TABLE 78

| Ex | Syn | DATA |
|---|---|---|
| 47 | Ex 1 | ESI+: 440 |
| 48 | Ex 2 | ESI+: 454 |
| 49 | Ex 2 | ESI+: 442 |
| 50 | Ex 2 | ESI+: 456 |
| 51 | Ex 4 | ESI+: 464 |
| 52 | Ex 4 | ESI+: 500 |
| 53 | Ex 5 | ESI+: 498 |
| 54 | Ex 5 | ESI+: 486<br>NMR (DMSO-d6): 2.64 (3H, s), 3.90-4.00 (4H, m), 5.06 (2H, t, J = 5.6 Hz), 5.32 (2H, s), 6.91 (1H, dd, J = 6.9, 7.6 Hz), 7.01 (1H, dd, J = 0.8, 7.8 Hz), 7.08-7.15 (2H, m), 7.19-7.27 (2H, m), 7.42-7.48 (3H, m), 7.59 (1H, tt, J = 6.7, 8.4 Hz), 8.61 (1H, dd, J = 0.9, 6.9 Hz) |
| 55 | Ex 5 | ESI+: 486 |
| 56 | Ex 5 | ESI+: 483 |
| 57 | Ex 5 | ESI+: 487 |
| 58 | Ex 5 | ESI+: 499 |
| 59 | Ex 5 | ESI+: 482 |
| 60 | Ex 5 | ESI+: 473 |
| 61 | Ex 5 | ESI+: 486 |
| 62 | Ex 5 | ESI+: 483 |
| 63 | Ex 5 | ESI+: 474 |
| 64 | Ex 5 | ESI+: 474 |
| 65 | Ex 5 | ESI+: 444 |
| 66 | Ex 5 | ESI+: 444 |

TABLE 79

| Ex | Syn | DATA |
|---|---|---|
| 67 | Ex 5 | ESI+: 495<br>NMR (DMSO-d6): 2.28 (2H, dd, J = 5.9, 14.1 Hz), 2.52-2.58 (2H, m), 2.61 (3H, s), 4.13-4.21 (2H, m), 4.79 (2H, d, J = 6.0 Hz), 5.32 (2H, s), 6.90 (1H, dd, J = 6.9, 7.6 Hz), 6.99 (1H, dd, J = 0.8, 7.8 Hz), 7.19-7.27 (3H, m), 7.52-7.56 (1H, m), 7.59 (1H, tt, J = 6.7, 8.5 Hz), 7.78 (1H, ddd, J = 1.8, 7.5, 8.0 Hz), 8.41-8.46 (2H, m), 8.52 (1H, d, J = 0.9, 1.8, 4.8 Hz) |
| 68 | Ex 5 | ESI+: 465 |
| 69 | Ex 5 | APCI/ESI+: 515 |
| 70 | Ex 5 | ESI+: 503, 505 |
| 71 | Ex 5 | ESI+: 472 |
| 72 | Ex 5 | ESI+: 489<br>NMR (DMSO-d6): 2.39 (3H, d, J = 1.3 Hz), 2.63 (3H, s), 3.98-4.10 (4H, m), 5.11 (2H, t, J = 4.9 Hz), 5.32 (2 6.94 (1H, dd, J = 6.9, 7.6 Hz), 7.03 (1H, dd, J = 0.8, 7.8 Hz), 7.19-7.27 (2H, m), 7.37 (1H, q, J = 1.2 Hz), 7.59 |

TABLE 79-continued

| Ex | Syn | DATA |
| --- | --- | --- |
| | | (1H, tt, J = 6.7, 8.5 Hz), 7.66 (1H, s), 8.63 (1H, dd, J = 0.9, 6.9 Hz) |
| 73a | Ex 7 | ESI+: 428 |
| 73b | Ex 7 | ESI+: 428 |
| 74 | Ex 7 | ESI+: 502 |
| 75 | Ex 8 | ESI+: 488 |
| 76 | Ex 8 | ESI+: 484 |
| 77 | Ex 1, Ex 8 | ESI+: 473<br>NMR (DMSO-d6): 1.76 (3H, s), 2.39 (3H, d, J = 1.0 Hz), 2.61 (3H, s), 3.76 (1H, dd, J = 5.8, 10.7 Hz), 3.92 (1H, dd, J = 5.9, 10.7 Hz), 5.28-5.34 (3H, m), 6.93 (1H, t, J = 7.3 Hz), 7.02 (1H, d, J = 7.3 Hz), 7.19-7.27 (2H, m), 7.35-7.37 (1H, m), 7.59 (1H, tt, J = 6.8, 8.4 Hz), 7.93 (1H, s), 8.57 (1H, d, J = 6.3 Hz) |
| 78 | PEx 16, Ex 5 | ESI+: 489 |

TABLE 80

| Ex | Syn | DATA |
| --- | --- | --- |
| 79 | PEx 8, Ex 1 | ESI+: 459 |
| 80 | Ex 1 | ESI+: 479 |
| 81 | Ex 1 | APCI/ESI+: 458<br>NMR (DMSO-d6): 1.51 (3H, t, J = 7.3 Hz), 2.56 (3H, s), 3.85-3.97 (2H, m), 4.68 (2H, q, J = 7.3 Hz), 5.12 (1H, t, J = 5.7 Hz), 5.31 (2H, s), 5.42-5.49 (1H, m), 6.94 (1H, dd, J = 6.9, 7.6 Hz), 7.02 (1H, dd, J = 0.7, 7.8 Hz), 7.19-7.27 (2H, m), 7.59 (1H, tt, J = 6.8, 8.5 Hz), 8.27 (1H, d, J = 8.2 Hz), 8.57 (1H, d, J = 0.8, 6.7 Hz) |
| 82 | Ex 1 | ESI+: 458 |
| 83 | Ex 1 | ESI+: 480 |
| 84 | Ex 1 | ESI+: 428 |
| 85 | Ex 1 | ESI+: 447 |
| 86 | Ex 1 | ESI+: 442 |
| 87 | Ex 1 | ESI+: 484 |
| 88 | Ex 1 | ESI+: 454 |
| 89 | Ex 1 | ESI+: 483 |
| 90 | Ex 1 | ESI+: 483 |
| 91 | Ex 1 | ESI+: 512<br>NMR (DMSO-d6): 1.81 (3H, s), 2.56 (3H, s), 3.85-3.95 (2H, m), 5.31 (2H, s), 5.45 (1H, t, J = 6.5 Hz), 6.93 (1H, dd, J = 6.9, 7.7 Hz), 7.03 (1H, dd, J = 0.8, 7.8 Hz), 7.19-7.27 (2H, m), 7.58 (1H, tt, J = 6.7, 8.4 Hz), 8.36-8.40 (2H, m) |
| 92 | Ex 1 | ESI+: 482 |
| 93 | Ex 2 | ESI+: 470 |
| 94 | Ex 2 | ESI+: 470 |
| 95 | Ex 5 | ESI+: 472 |

TABLE 81

| Ex | Syn | DATA |
| --- | --- | --- |
| 96 | Ex 5 | ESI+: 510<br>NMR (DMSO-d6): 2.59 (3H, s), 4.03 (2H, dd, J = 6.1, 10.7 Hz), 4.18 (2H, dd, J = 6.0, 10.7 Hz), 5.11 (2H, t, J = 6.0 Hz) 5.31 (2H, s), 6.90 (1H, dd, J = 7.0, 7.6 Hz), 7.00 (1H, dd, J = 0.8, 7.7 Hz), 7.18-7.27 (2H, m), 7.58 (1H, tt, J = 6.7, 8.5 Hz), 7.94 (1H, s), 8.40 (1H, dd, J = 0.9, 6.9 Hz), 8.57 (1H, t, J = 56.6 Hz) |
| 97 | Ex 5 | ESI+: 480 |
| 98 | Ex 5 | ESI+: 444 |
| 99 | Ex 5 | ESI+: 458 |
| 100 | Ex 5 | ESI+: 470 |
| 101 | Ex 7 | ESI+: 486 |
| 102 | Ex 7 | ESI+: 504 |
| 103 | Ex 8 | ESI+: 498 |
| 104 | Ex 8 | ESI+: 458 |
| 105 | Ex 105 | ESI+: 516 |
| 106 | Ex 105 | ESI+: 502 |
| 107a | Ex 107 | ESI+: 482<br>(AC-A) Rt = 7.64 min |

TABLE 81-continued

| Ex | Syn | DATA |
| --- | --- | --- |
| 107b | Ex 107 | ESI+: 482<br>(AC-A) Rt = 5.18 min |
| 108a | Ex 108 | ESI+: 458<br>(AC-B) Rt = 5.19 min |
| 108b | Ex 108 | ESI+: 458<br>(AC-B) Rt = 4.00 min |
| 109 | Ex 1, Ex 5 | ESI+: 486 |
| 110 | PEx 11, Ex 1 | APCI/ESI+: 472 |
| 111 | PEx 47 | ESI+: 490<br>NMR (DMSO-d6): 1.00-1.35 (5H, m), 1.63-1.90 (6H, m), 1.82 (3H, s), 2.70 (3H, s), 3.67 (1H, dd, J = 4.6, 10.6 Hz), 3.77 (1H, dd, J = 5.0, 10.6 Hz), 3.96 (2H, d, J = 6.2 Hz), 5.33 (1H, t, J = 5.2 Hz), 6.76-6.84 (2H, m), 7.52 (1H, t, J = 7.7 Hz), 7.58-7.62 (1H, m), 7.73 (1H, s), 7.88 (1H, dt, Jd = 7.6 Hz, Jt = 1.4 Hz), 8.12 (1H, t, J = 1.6 Hz), 8.48 (1H, dd, J = 1.2, 6.6 Hz) |

TABLE 82

| Ex | Syn | DATA |
| --- | --- | --- |
| 112 | Ex 112 | ESI+: 510 |
| 113 | Ex 113 | ESI+: 510<br>NMR (DMSO-d6): 2.65 (3H, s), 4.02 (2H, d, J = 10.8 Hz), 4.20 (2H, d, J = 10.7 Hz), 5.45 (2H, s), 7.21-7.29 (2H, m), 7.31-7.42 (1H, m), 7.50-7.77 (1H, m), 7.61 (1H, tt, J = 6.8, 8.5 Hz), 8.48 (1H, d, J = 6.8 Hz), 8.58 (1H, t, J = 56.5 Hz), 8.54-8.69 (1H, brs) |
| 114 | Ex 114 | ESI+: 494<br>NMR (DMSO-d6): 1.84 (3H, s), 2.60 (3H, s), 3.85 (1H, dd, J = 4.7, 10.7 Hz), 3.93 (1H, dd, J = 4.7, 10.7 Hz), 5.28-5.36 (3H, m), 6.90 (1H, dd, J = 6.9, 7.6 Hz), 7.01 (1H, dd, J = 0.8, 7.8 Hz), 7.19-7.27 (2H, m), 7.58 (1H, tt, J = 6.7, 8.5 Hz), 8.13 (1H, s), 8.41 (1H, dd, J = 0.9, 6.9 Hz), 8.57 (1H, t, J = 56.6 Hz) |
| 115 | Ex 115 | ESI+: 494<br>NMR (DMSO-d6):1.84 (3H, s), 2.65 (3H, s), 3.86 (1H, d, J = 10.9 Hz), 3.99 (1H, d, J = 10.8 Hz), 5.44 (2H, s), 7.20-7.29 (2H, m), 7.30-7.40 (1H, m), 7.50-7.66 (2H, m), 8.50 (1H, d, J = 6.9 Hz), 8.58 (1H, t, J = 56.6 Hz), 8.73-8.83 (1H, brs) |
| 116 | Ex 116 | ESI+: 494<br>NMR (DMSO-d6): 1.84 (3H, s), 2.65 (3H, s), 3.87 (1H, d, J = 10.8 Hz), 4.00 (1H, d, J = 10.8 Hz), 5.45 (2H, s), 7.22-7.33 (5H, m), 7.38 (1H, t, J = 7.1 Hz), 7.55-7.66 (4H, m), 8.50 (1H, d, J = 6.8 Hz), 8.58 (1H, t, J = 56.6 Hz), 8.76-8.90 (1H, brs) |
| 117 | Ex 117 | APCI/ESI+: 458<br>NMR (DMSO-d6): 1.73 (3H, s), 2.45 (3H, s), 2.57 (3H, s), 3.81 (1H, dd, J = 6.2, 10.9 Hz), 3.88 (1H, dd, J = 6.2, 10.8 Hz), 5.31 (2H, s), 5.37 (1H, t, J = 6.1 Hz), 6.92 (1H, t, J = 7.3 Hz), 7.02 (1H, d, J = 7.8 Hz), 7.19-7.27 (2H, m), 7.58 (1H, tt, J = 7.0, 8.0 Hz), 8.01 (1H, s), 8.47 (1H, d, J = 6.7 Hz) |

TABLE 83

| Ex | Syn | DATA |
| --- | --- | --- |
| 118 | Ex 118 | ESI+: 474<br>NMR (DMSO-d6): 1.80 (3H, s), 2.59 (3H, s), 2.67 (3H, s), 3.84 (1H, dd, J = 5.8, 10.8 Hz), 3.91 (1H, dd, J = 5.8, 10.8 Hz), 5.31 (2H, s), 5.44 (1H, t, J = 5.4 Hz), 6.93 (1H, t, J = 6.9, 7.6 Hz), 7.02 (1H, dd, J = 0.8, 7.7 Hz), 7.19-7.28 (2H, m), 7.59 (1H, tt, J = 6.7, 8.4 Hz), 8.11 (1H, s), 8.51 (1H, dd, J = 0.9, 6.9 Hz) |

Furthermore, the structures of the other compounds of the formula (I) are shown in Tables 84 to 90. These can be easily prepared by using the methods described in Preparation Examples or Examples above, methods known to a person skilled in the art, or modified methods thereof.

TABLE 84
| No. | Str |
|---|---|
| 1 | 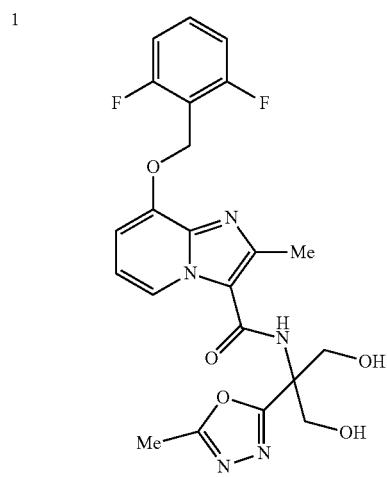 |
| 2 | 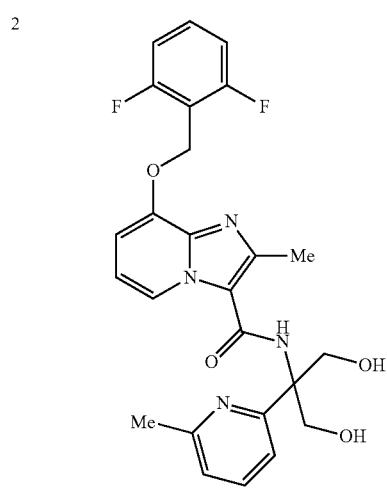 |
| 3 | 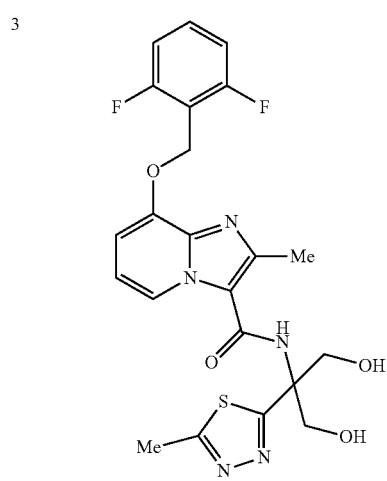 |
TABLE 84-continued
| No. | Str |
|---|---|
| 4 | 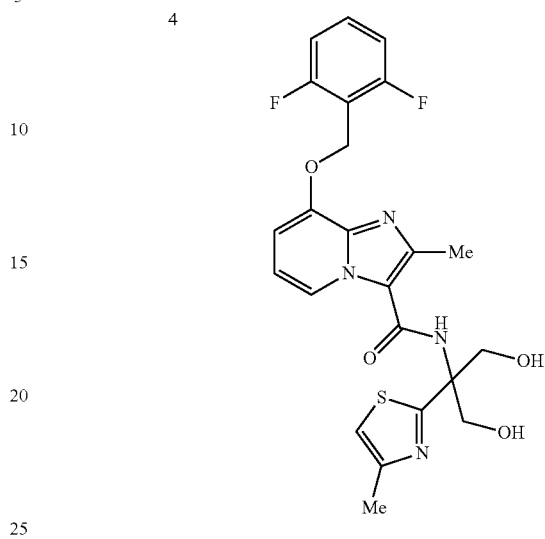 |
| 5 | 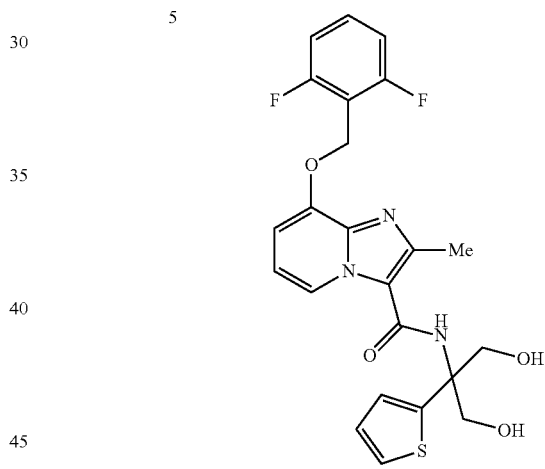 |
| 6 | 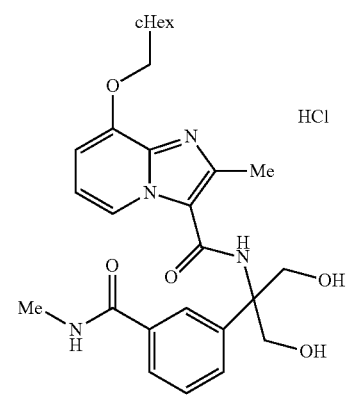 |

TABLE 85
| No. | Str |
|---|---|
| 7 | 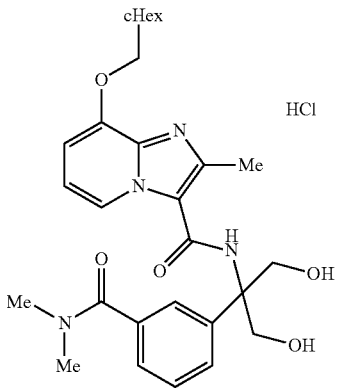 |
| 8 | 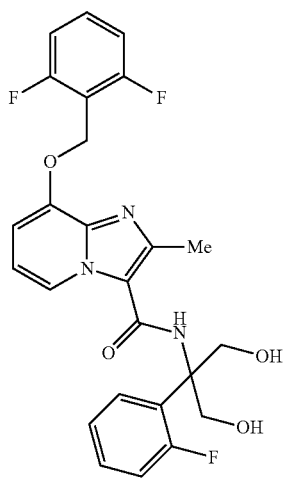 [SMILES: Cc1nc2c(OCc3c(F)cccc3F)cccn2c1C(=O)NC(CO)(CO)c1ccccc1F] |
| 9 | 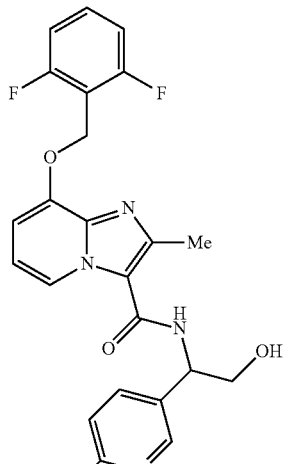 |
TABLE 85-continued
| No. | Str |
|---|---|
| 10 | 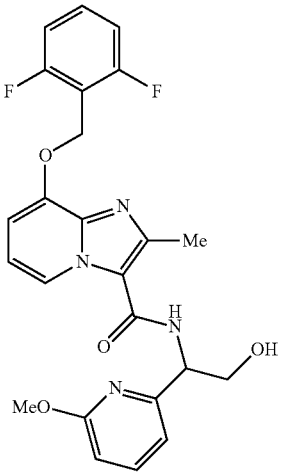 [SMILES: COc1cccc(C(CO)NC(=O)c2c(C)nc3c(OCc4c(F)cccc4F)cccn23)n1] |
| 11 | 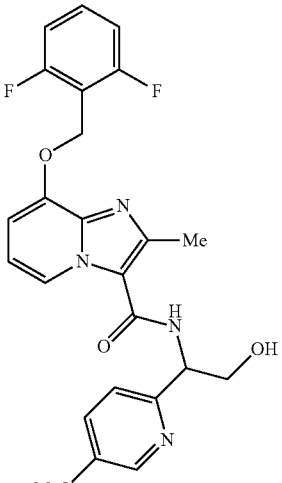 |
| 12 | 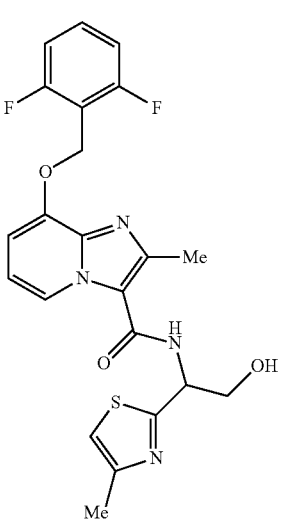 [SMILES: Cc1csc(C(CO)NC(=O)c2c(C)nc3c(OCc4c(F)cccc4F)cccn23)n1] |

TABLE 86
| No. | Str |
|---|---|
| 13 | 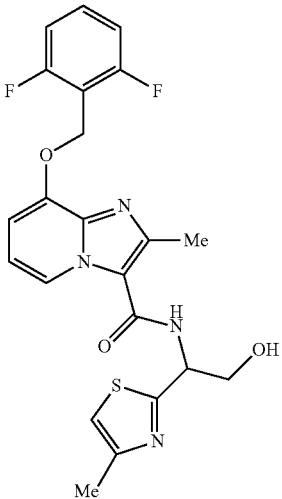 [SMILES: Cc1csc(C(CO)NC(=O)c2c(C)nc3c(OCc4c(F)cccc4F)cccn23)n1] |
| 14 | 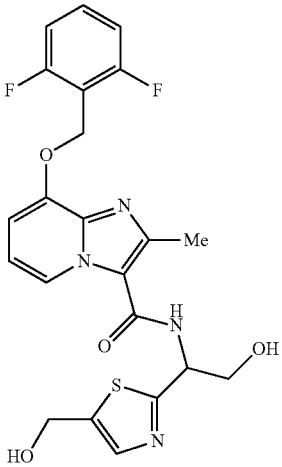 [SMILES: Cc1nc2c(OCc3c(F)cccc3F)cccn2c1C(=O)NC(CO)c1ncc(CO)s1] |
| 15 | 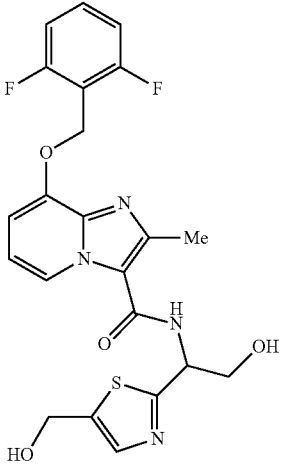 [SMILES: Cc1nc2c(OCc3c(F)cccc3F)cccn2c1C(=O)NC(CO)c1ncc(CO)s1] |
TABLE 86-continued
| No. | Str |
|---|---|
| 16 | 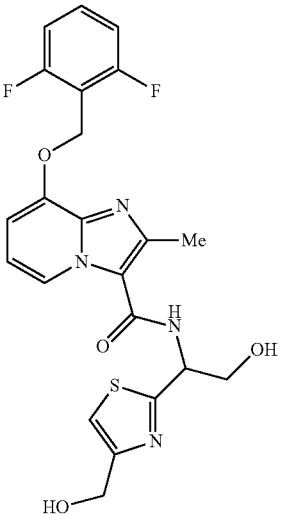 [SMILES: Cc1nc2c(OCc3c(F)cccc3F)cccn2c1C(=O)NC(CO)c1nc(CO)cs1] |
| 17 | 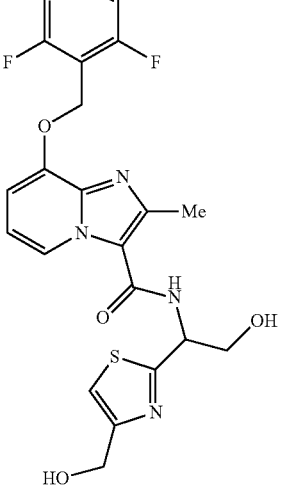 |
| 18 | 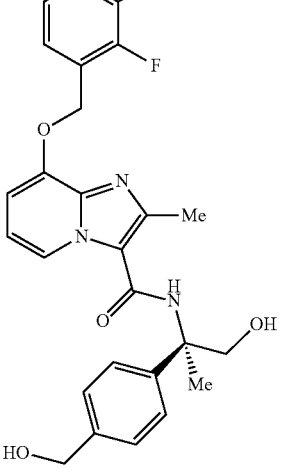 |

TABLE 87
| No. | Str |
|---|---|
| 19 | 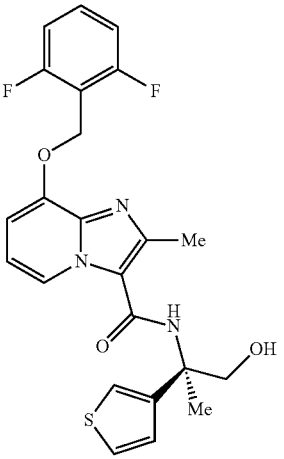 [SMILES: Cc1nc2c(OCc3c(F)cccc3F)cccn2c1C(=O)N[C@@](C)(CO)c1ccsc1] |
| 20 | 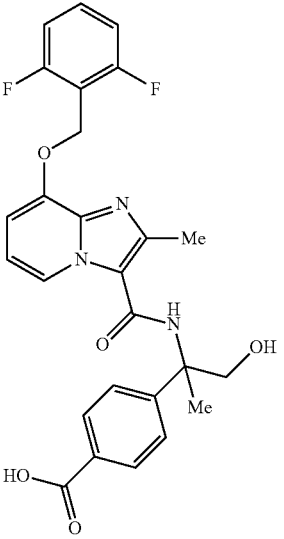 [SMILES: Cc1nc2c(OCc3c(F)cccc3F)cccn2c1C(=O)NC(C)(CO)c1ccc(C(=O)O)cc1] |
| 21 | 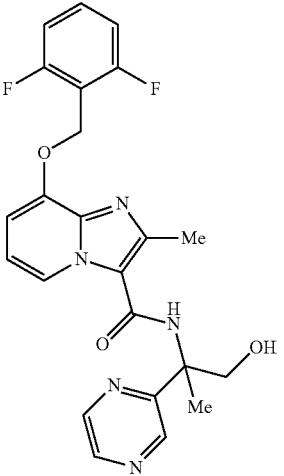 [SMILES: Cc1nc2c(OCc3c(F)cccc3F)cccn2c1C(=O)NC(C)(CO)c1cnccn1] |
TABLE 87-continued
| No. | Str |
|---|---|
| 22 | 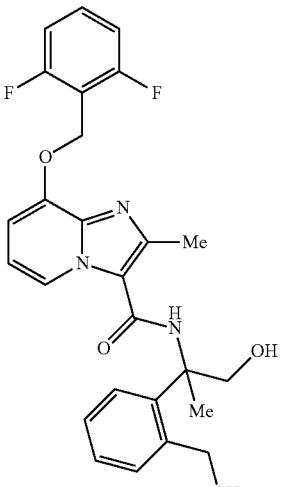 |
| 23 | 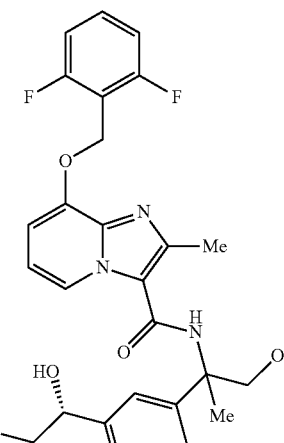 |
| 24 | 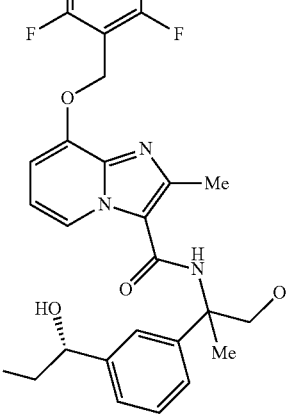 |

TABLE 88
| No. | Str |
|---|---|
| 25 | 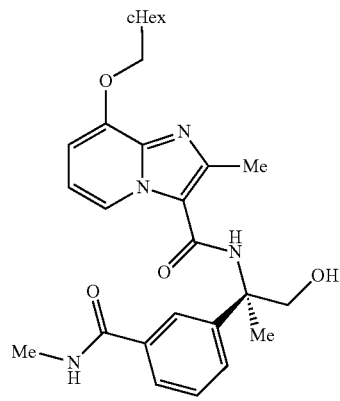 |
| 26 | 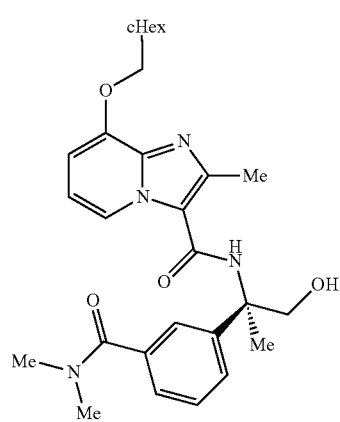 |
| 27 | 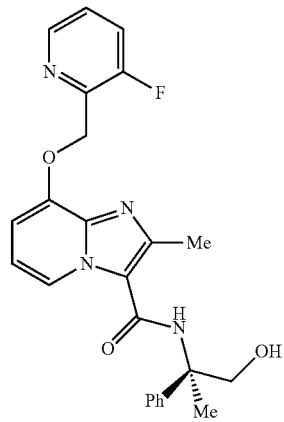 |
TABLE 88-continued
| No. | Str |
|---|---|
| 28 | 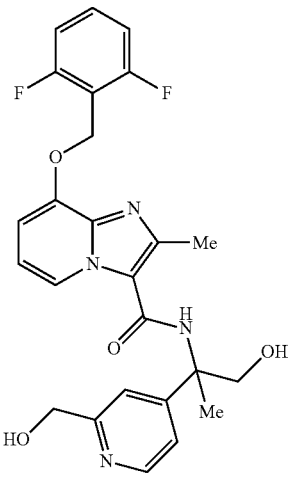 [SMILES: Cc1nc2c(OCc3c(F)cccc3F)cccn2c1C(=O)NC(C)(CO)c1ccnc(CO)c1] |
| 29 | 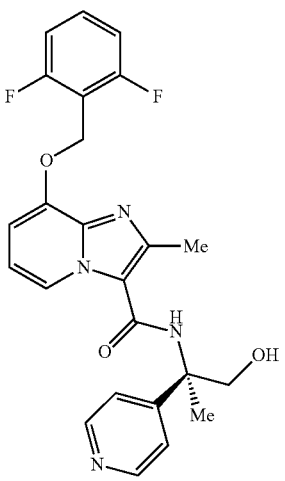 [SMILES: Cc1nc2c(OCc3c(F)cccc3F)cccn2c1C(=O)N[C@@](C)(CO)c1ccncc1] |
| 30 | 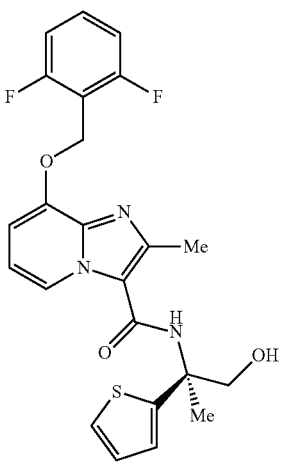 [SMILES: Cc1nc2c(OCc3c(F)cccc3F)cccn2c1C(=O)N[C@@](C)(CO)c1cccs1] |

TABLE 89
| No. | Str |
|---|---|
| 31 | 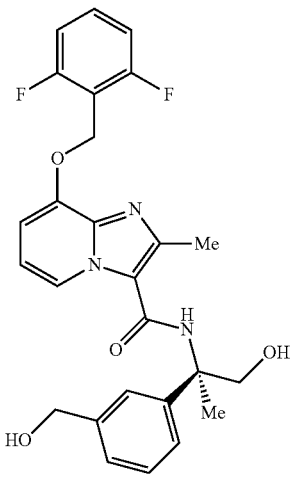 [SMILES: Cc1nc2c(OCc3c(F)cccc3F)cccn2c1C(=O)N[C@@](C)(CO)c1cccc(CO)c1] |
| 32 | 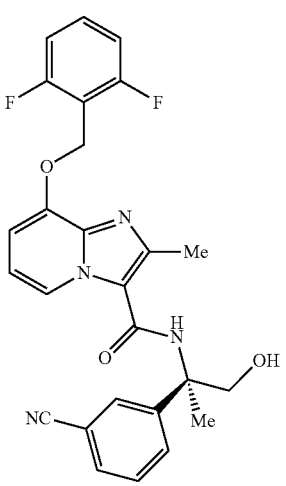 [SMILES: Cc1nc2c(OCc3c(F)cccc3F)cccn2c1C(=O)N[C@@](C)(CO)c1cccc(C#N)c1] |
| 33 | 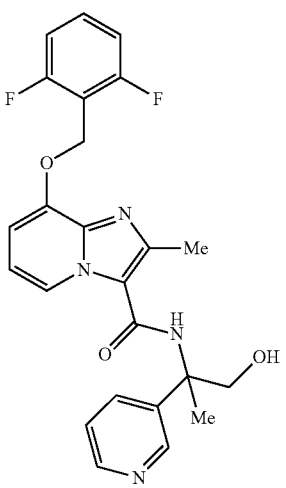 [SMILES: Cc1nc2c(OCc3c(F)cccc3F)cccn2c1C(=O)NC(C)(CO)c1cccnc1] |
TABLE 89-continued
| No. | Str |
|---|---|
| 34 | 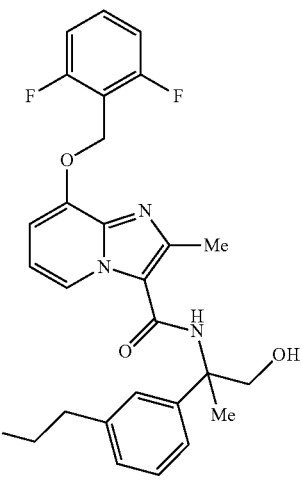 |
| 35 | |
| 36 | 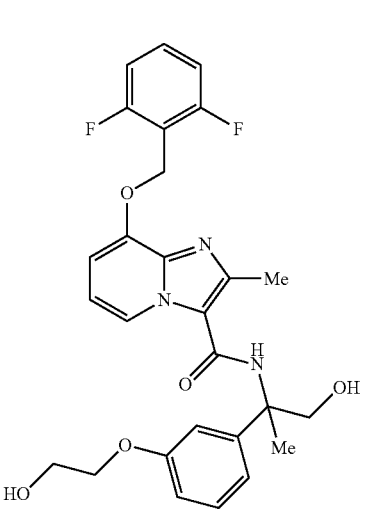 [SMILES: Cc1nc2c(OCc3c(F)cccc3F)cccn2c1C(=O)NC(C)(CO)c1cccc(OCCO)c1] |

TABLE 90

| No. | Str |
|---|---|
| 37 | 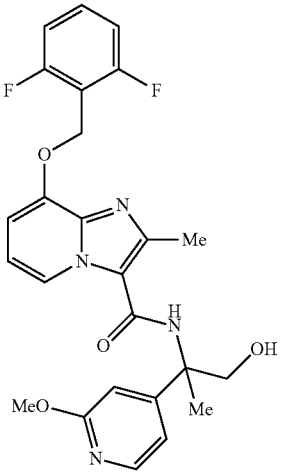 [SMILES: COc1cc(C(C)(CO)NC(=O)c2c(C)nc3c(OCc4c(F)cccc4F)cccn23)ccn1] |
| 38 | 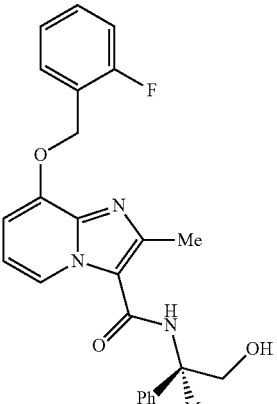 |
| 39 | |

TABLE 90-continued

| No. | Str |
|---|---|
| 40 | |
| 41 | |

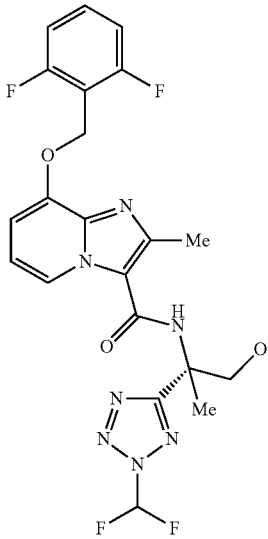

INDUSTRIAL APPLICABILITY

Compound of formula (I) or a salt thereof has an sGC activation and can be used as active ingredients of pharmaceutical compositions for preventing or treating sGC-related cardiovascular diseases, for example, hypertension, atherosclerosis, lumbar spinal canal stenosis, peripheral arterial diseases, intermittent claudication and critical limb ischemia which are accompanied by peripheral arterial diseases, stable or unstable angina pectoris, heart failure, thrombosis, stroke, sexual dysfunction, or pulmonary hypertension.

The invention claimed is:
1. 8-[(2,6-difluorobenzyl)oxy]-N-{2-[2-(difluoromethyl)-2H-tetrazol-5-yl]-1-hydroxypropan-2-yl}-2-methylimidazo[1,2-a]pyridine-3-carboxamide or a salt thereof.
2. 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide or a salt thereof.
3. The compound of claim 2, which is 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide hydrobromide.

4. The compound of claim 2, which is 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide benzenesulfonate.

5. The compound of claim 3, which is a crystal having peaks at around 2θ (°) 5.6, 9.9, 10.2, 11.2, 12.2, 12.4, 13.1, 14.7, 14.9, and 15.6 with powder X-ray diffraction.

6. The compound of claim 4, which is a crystal having peaks at around 2θ (°) 5.7, 9.6, 10.2, 11.0, 12.4, 14.2, 16.3, 17.2, 18.8, and 19.1 with powder X-ray diffraction.

7. 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide or a salt thereof.

8. The compound of claim 7, which is 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide hydrobromide.

9. The compound of claim 8, which is a crystal having peaks at around 2θ (°) 7.9, 8.8, 10.2, 11.1, 13.1, 13.5, 13.7, 14.4, 14.7, and 15.8 with powder X-ray diffraction.

10. A pharmaceutical composition, comprising:
the compound or salt thereof of claim 1, and
a pharmaceutically acceptable excipient.

11. A pharmaceutical composition, comprising:
the compound or salt thereof of claim 2, and
a pharmaceutically acceptable excipient.

12. A method for treating occlusive thrombotic vasculitis, peripheral arterial occlusive disease, intermittent claudication, critical limb ischemia, Raynaud's disease, Raynaud's syndrome, hypertension, or pulmonary hypertension, the method comprising:
administering, to a subject in need thereof, an effective amount of the compound or salt thereof of claim 1.

13. A method for treating occlusive thrombotic vasculitis, peripheral arterial occlusive disease, intermittent claudication, critical limb ischemia, Raynaud's disease, Raynaud's syndrome, hypertension, or pulmonary hypertension, the method comprising:
administering, to a subject in need thereof, an effective amount of the compound or salt thereof of claim 2.

14. A pharmaceutical composition, comprising:
the compound or salt thereof of claim 7, and
a pharmaceutically acceptable excipient.

15. A method for treating occlusive thrombotic vasculitis, peripheral arterial occlusive disease, intermittent claudication, critical limb ischemia, Raynaud's disease, Raynaud's syndrome, hypertension, or pulmonary hypertension, the method comprising:
administering, to a subject in need thereof, an effective amount of the compound or salt thereof of claim 7.

16. A method of activating guanylate cyclase, the method comprising:
administering an effective amount of a compound to a subject in need thereof,
wherein the compound comprises 8-[(2,6-difluorobenzyl)oxy]-N-{2-[2-(difluoromethyl)-2H-tetrazol-5-yl]-1-hydroxypropan-2-yl}-2-methylimidazo[1,2-a]pyridine-3-carboxamide or a salt thereof.

17. A method of activating guanylate cyclase, the method comprising:
administering an effective amount of a compound to a subject in need thereof,
wherein the compound comprises 8-[(2,6-difluorobenzyl)oxy]-N-{(2R)-2-[2-(difluoromethyl)-2H-tetrazol-5-yl]-1-hydroxypropan-2-yl}-2-methylimidazo[1,2-a]pyridine-3-carboxamide or a salt thereof.

18. A method of activating guanylate cyclase, the method comprising:
administering an effective amount of a compound to a subject in need thereof,
wherein the compound comprises 8-[(2,6-difluorobenzyl)oxy]-N-{2-[2-(difluoromethyl)-2H-tetrazol-5-yl]-1,3-dihydroxypropan-2-yl}-2-methylimidazo[1,2-a]pyridine-3-carboxamide or a salt thereof.

\* \* \* \* \*